United States Patent

Akashi et al.

Patent Number: 4,465,630
Date of Patent: Aug. 14, 1984

[54] TETRAAZAANNULENE COBALT COMPLEX COMPOUNDS AND METHOD FOR PREPARATION THEREFOR

[75] Inventors: Kageyasu Akashi; Nobuhiko Suga, both of Fuji, Japan

[73] Assignee: Asahi Kasei Kogyo Kabushiki Kaisha, Osaka, Japan

[21] Appl. No.: 409,919

[22] Filed: Aug. 20, 1982

[30] Foreign Application Priority Data

| Aug. 24, 1981 | [JP] | Japan | 56/132438 |
| Aug. 31, 1981 | [JP] | Japan | 56/136312 |
| Aug. 31, 1981 | [JP] | Japan | 56/136313 |
| Aug. 31, 1981 | [JP] | Japan | 56/136314 |
| Aug. 31, 1981 | [JP] | Japan | 56/136315 |
| Jun. 15, 1982 | [JP] | Japan | 57/102543 |
| Jun. 16, 1982 | [JP] | Japan | 57/103509 |
| Jun. 19, 1982 | [JP] | Japan | 57/105678 |
| Jun. 19, 1982 | [JP] | Japan | 57/195679 |

[51] Int. Cl.³ ............... C07F 15/00; B01J 23/62
[52] U.S. Cl. .................. 260/239 BC; 502/167
[58] Field of Search ........................ 260/239 BC

[56] References Cited

FOREIGN PATENT DOCUMENTS 2046354  3/1972  Fed. Rep. of Germany.

OTHER PUBLICATIONS

Reichardt, Chemical Abstract, vol. 90, 1979, p. 625, 204064s.
J. Coord. Chem., vol. 9, pp. 161–166 (1979).
Bulletin of the Chem. Society of Japan, vol. 50(9), pp. 2485–2486 (1977).
Z. Naturforsch, vol. 28a, pp. 1009–1021 (1973).

Primary Examiner—Donald G. Daus
Assistant Examiner—Cecilia Shen
Attorney, Agent, or Firm—Finnegan, Henderson, Farabow, Garrett & Dunner

[57] ABSTRACT

A tetraazaannulene cobalt complex compound having the general formula (I);

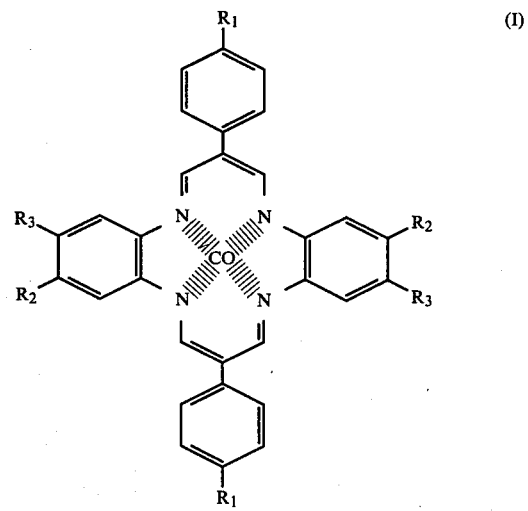

wherein $R_1$, $R_2$ and $R_3$ each independently is a hydrogen atom, a $C_{1-8}$ alkoxy group or a $C_{1-8}$ alkyl group but in case of one of $R_1$, $R_2$ and $R_3$ being a hydrogen atom the other two groups are not hydrogen atoms at the same time, and when $R_1$ is a methyl group $R_2$ and $R_3$ are not hydrogen atoms at the same time.

22 Claims, No Drawings

TETRAAZAANNULENE COBALT COMPLEX COMPOUNDS AND METHOD FOR PREPARATION THEREFOR

BACKGROUND OF THE INVENTION

1. Field of the Invention

This invention relates to a tetraazaannulene cobalt complex compound (hereinafter referred to Co-TAA) useful as an oxygen reduction catalyst and a method for the preparation of the Co-TAA.

2. Description of the Prior Art

Various kinds of oxygen reduction catalysts have been known. Especially, platinum has been well known as an oxygen reduction catalyst because of the superior catalytic properties. However, it is difficult to practically employ platinium as a catalyst in a fuel battery because platinum is expensive and a rare metal. Therefore, the development of new catalysts having a low oxygen reduction voltage and a high catalytic activity have been desired and made. However, the catalysts which can take the place of platinum have not been found.

The Co-TAA having the formula (VII);

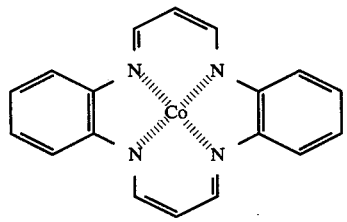

(VII)

is reported as an oxygen reduction catalyst having a high activity in F. Beck et al, Z. Naturforsch. 28a, 1009–1021(1973), and DE-OS No. 20 46 354. However, the catalyst life of the Co-TAA of the formula (VII) is short and, in addition, the catalyst activity is not satisfactory.

Further, the Co-TAA having the formula (VIII);

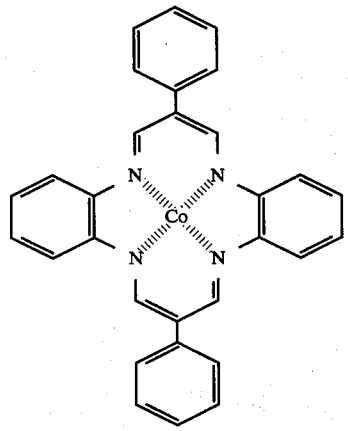

(VIII)

is reported in Y. Nishida et al, Bulletin of the Chemical Society of Japan, Vol. 50(9), 2485–2486 (1977). There is no description relating to the oxygen reduction catalyst properties of the Co-TAA of the formula (VIII) in the report. The inventors of this invention have produced the Co-TAA of the formula (VIII) to measure the catalytic properties, and found that the catalyst activity is insufficient though the catalyst life is long.

A method for the preparation of the Co-TAA is described in Y. Nishida et al, Journal of Coordination Chemistry, Vol. 9, 161–166 (1979). This method, however, has a defect that the reaction procedures and the aftertreatments are difficult due to the use of sulfur and acetyl hydroperoxide in the production of the starting material, that is, dithiolium hydrogensulfate. Further, this method has such defects that the yields of the tetraazaannulene and the Co-TAA are low, that the purity of the Co-TAA is also low and that the purification of the Co-TAA is difficult.

SUMMARY OF THE INVENTION

An object of this invention is to provide a novel Co-TAA.

Another object of this invention is to provide a novel method for preparing the Co-TAA including conventional Co-TAA, and a tetraazaannulene derivative which is an intermediate of the Co-TAA.

Accordingly, this invention provides a novel Co-TAA having the general formula (I);

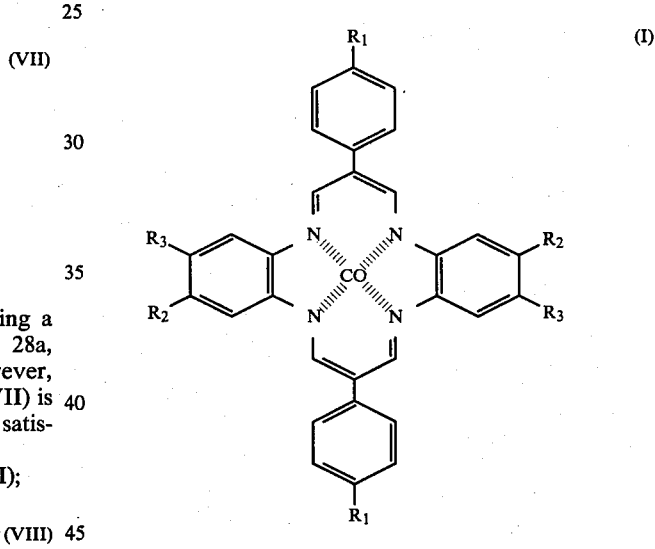

(I)

wherein $R_1$, $R_2$ and $R_3$ each independently is a hydrogen atom, a $C_{1-8}$ alkoxy group or a $C_{1-8}$ alkyl group but in case of one of $R_1$, $R_2$ and $R_3$ being a hydrogen atom the other two groups are not hydrogen atoms at the same time, and when $R_1$ is a methyl group $R_2$ and $R_3$ are not hydrogen atoms at the same time.

DETAILED DESCRIPTION OF THE INVENTION

Suitable examples Co-TAA of this invention of the formula (I) include;

(1) $R_1$ is a $C_{1-8}$ alkoxy group,
(2) $R_1$ and $R_2$ each independently is a $C_{1-8}$ alkoxy group,
(3) $R_1$ and $R_2$ each independently is a $C_{1-8}$ alkoxy group and $R_3$ is a hydrogen atom,
(4) each of $R_1$, $R_2$ and $R_3$ independently is a $C_{1-8}$ alkoxy group,
(5) $R_1$ is a $C_{1-8}$ alkoxy group and $R_2$ and $R_3$ are the same and $C_{1-8}$ alkoxy groups,
(6) $R_1$ is a $C_{1-8}$ alkoxy group and $R_2$ and $R_3$ are both hydrogen atoms, (7) $R_1$ is a $C_{1-8}$ alkoxy group and $R_2$ and $R_3$ each independently is a $C_{1-8}$ alkyl group,
(8) $R_1$ is a $C_{1-8}$ alkoxy group and $R_2$ and $R_3$ are the same and $C_{1-8}$ alkyl groups,
(9) $R_1$ is a $C_{1-8}$ alkyl group,
(10) $R_1$ is a $C_{1-8}$ alkyl group and $R_2$ and $R_3$ each independently is a $C_{1-8}$ alkoxy group,
(11) $R_1$ is a $C_{1-8}$ alkyl group and $R_2$ and $R_3$ are the same and $C_{1-8}$ alkoxy groups,
(12) each of $R_1$, $R_2$ and $R_3$ independently is a $C_{1-8}$ alkyl group,
(13) $R_1$ is a $C_{1-8}$ alkyl group and $R_2$ and $R_3$ are the same and $C_{1-8}$ alkyl groups,
(14) $R_1$ is a $C_{2-8}$ alkyl group and $R_2$ and $R_3$ are both hydrogen atoms,
(15) $R_1$ is a hydrogen atom,
(16) $R_1$ is a hydrogen atom and $R_2$ is a $C_{1-8}$ alkoxy group,
(17) $R_1$ is a hydrogen atom and $R_2$ and $R_3$ each independently is a $C_{1-8}$ alkoxy group,
(18) $R_1$ is a hydrogen atom and $R_2$ and $R_3$ are the same and $C_{1-8}$ alkoxy groups,
(19) $R_1$ and $R_3$ are both hydrogen atoms and $R_2$ is a $C_{1-8}$ alkoxy group,
(20) $R_1$ is a hydrogen atom and $R_2$ is a $C_{1-8}$ alkyl group,
(21) $R_1$ is a hydrogen atom and $R_2$ and $R_3$ each independently is a $C_{1-8}$ alkyl group,
(22) $R_1$ is a hydrogen atom and $R_2$ and $R_3$ are the same and $C_{1-8}$ alkyl groups, and
(23) $R_1$ and $R_3$ are both hydrogen atoms and $R_2$ is a $C_{1-8}$ alkyl group.

Preferred $R_1$, $R_2$ and $R_3$ include a hydrogen atom, a methoxy group, an ethoxy group, a n-propoxy group, an isopropoxy group, a n-butoxy group, an iso-butoxy group, a n-pentyloxy group, a n-hexyloxy group, a n-heptyloxy group, a n-octyloxy group, a methyl group, an ethyl group, a n-propyl group, an iso-propyl group, a n-butyl group, an iso-butyl group, a n-pentyl group, a n-hexyl group, a n-heptyl group and a n-octyl group.

Preferred Co-TAA of this invention is the compound of the formula (I) where one or two of $R_1$, $R_2$ and $R_3$ are methoxy groups, for example, one or two of $R_1$, $R_2$ and $R_3$ are methoxy groups and the other group or groups are hydrogen atoms, $R_1$ is a methoxy group and $R_2$ and $R_3$ are the same and $C_{4-8}$ alkoxy groups, $R_1$ is a methoxy group and $R_2$ and $R_3$ are the same and $C_{1-4}$ alkyl groups, $R_1$ is a $C_{4-8}$ alkoxy group and $R_2$ and $R_3$ are both methoxy groups, $R_1$ is a $C_{1-4}$ alkyl group and $R_2$ and $R_3$ are both methoxy groups, and all of $R_1$, $R_2$ and $R_3$ are methoxy groups; the compound of the formula (I) where one or two of $R_1$, $R_2$ and $R_3$ are methyl groups and the other group or groups are $C_{1-4}$ alkyl groups or $C_{4-8}$ alkoxy groups, for example, $R_1$ is a methyl group and $R_2$ and $R_3$ are the same and $C_{1-4}$ alkyl groups or $C_{4-8}$ alkoxy group, and $R_2$ and $R_3$ are both methyl groups and $R_1$ is a $C_{1-4}$ alkyl group or a $C_{4-8}$ alkoxy group; the compound of the formula (I) where $R_1$, $R_2$ and $R_3$ are all methyl groups; the compound of the formula (I) where $R_1$ and $R_2$ are the same and $C_{4-8}$ alkoxy groups and $R_3$ is a hydrogen atom; the compound of the formula (I) where $R_1$ is a $C_{1-4}$ alkoxy group and $R_2$ and $R_3$ are the same and $C_{1-4}$ alkyl groups; or the compound of the formula (I) where $R_1$, $R_2$ and $R_3$ are all n-butoxy groups.

More specifically, preferred examples of the Co-TAA having a higher catalyst activity and a longer catalyst life include

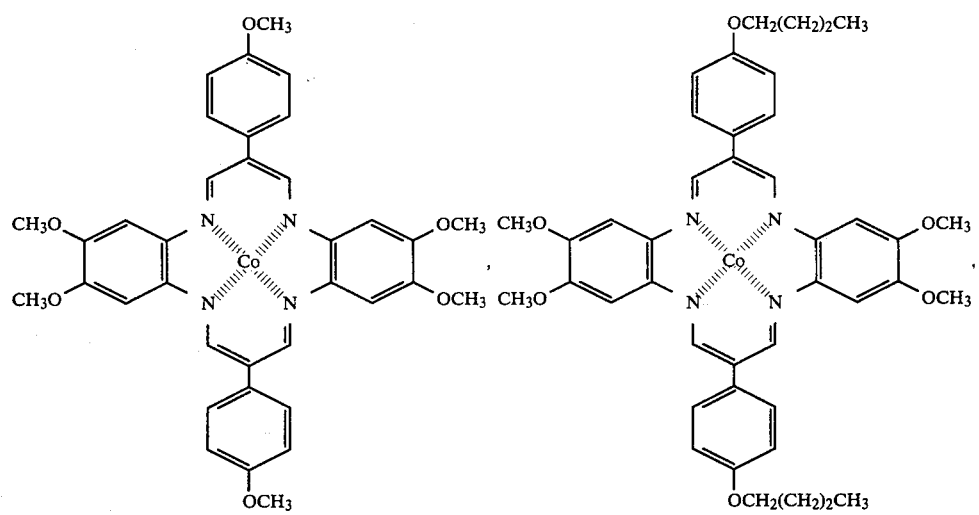

-continued
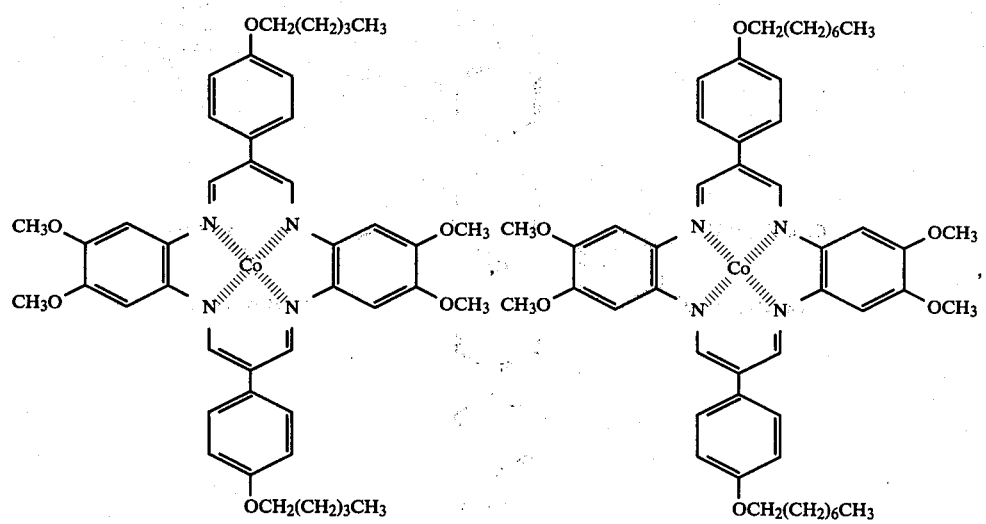
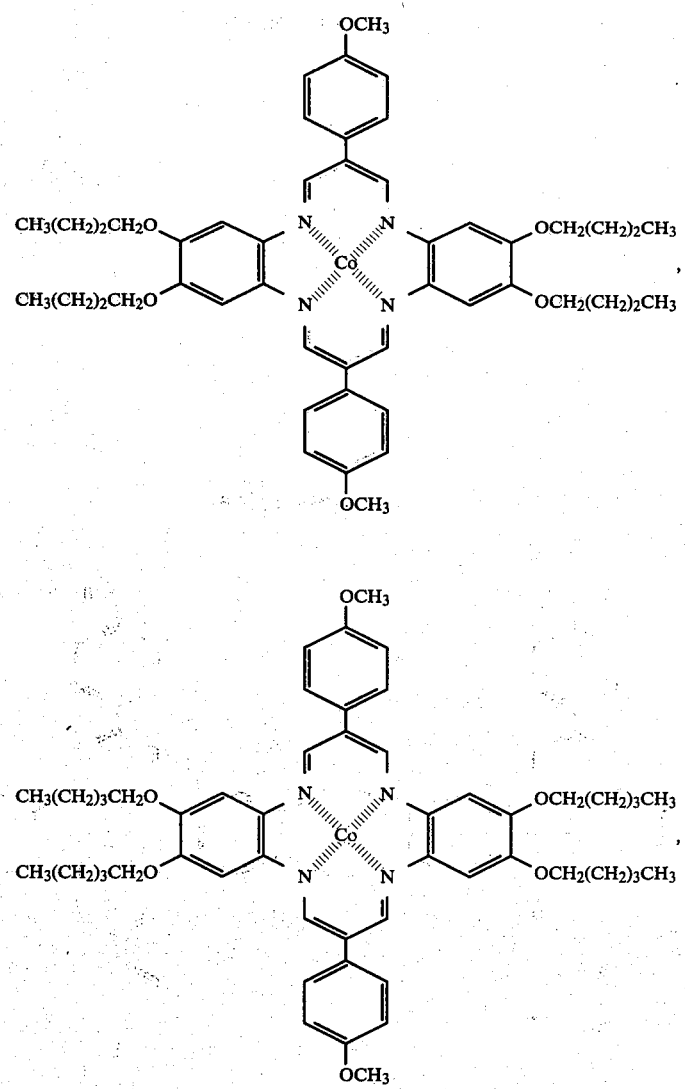

-continued
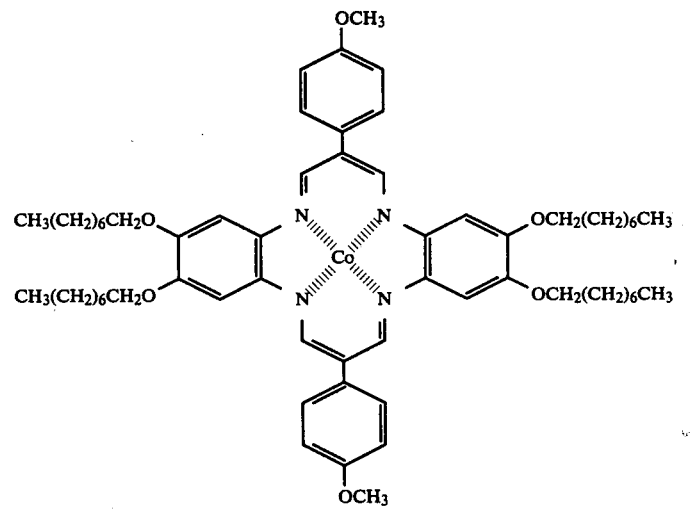
,
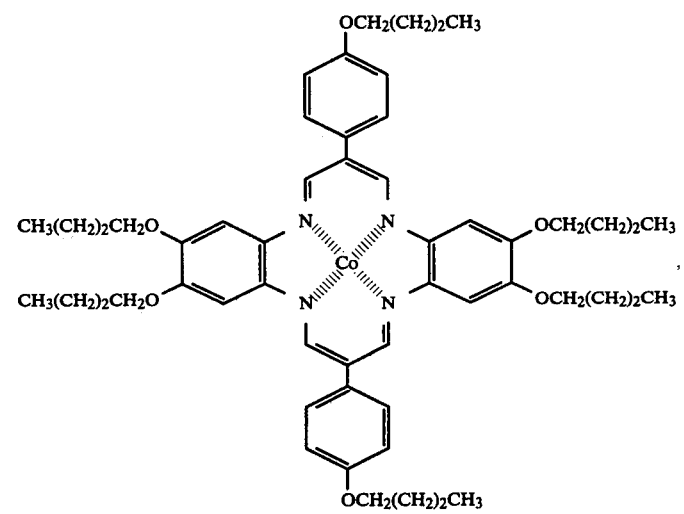
,
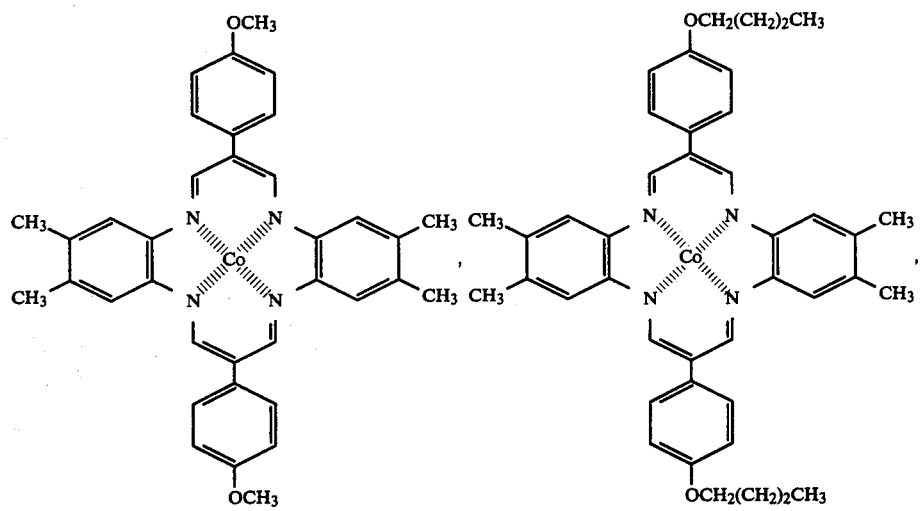
,

-continued
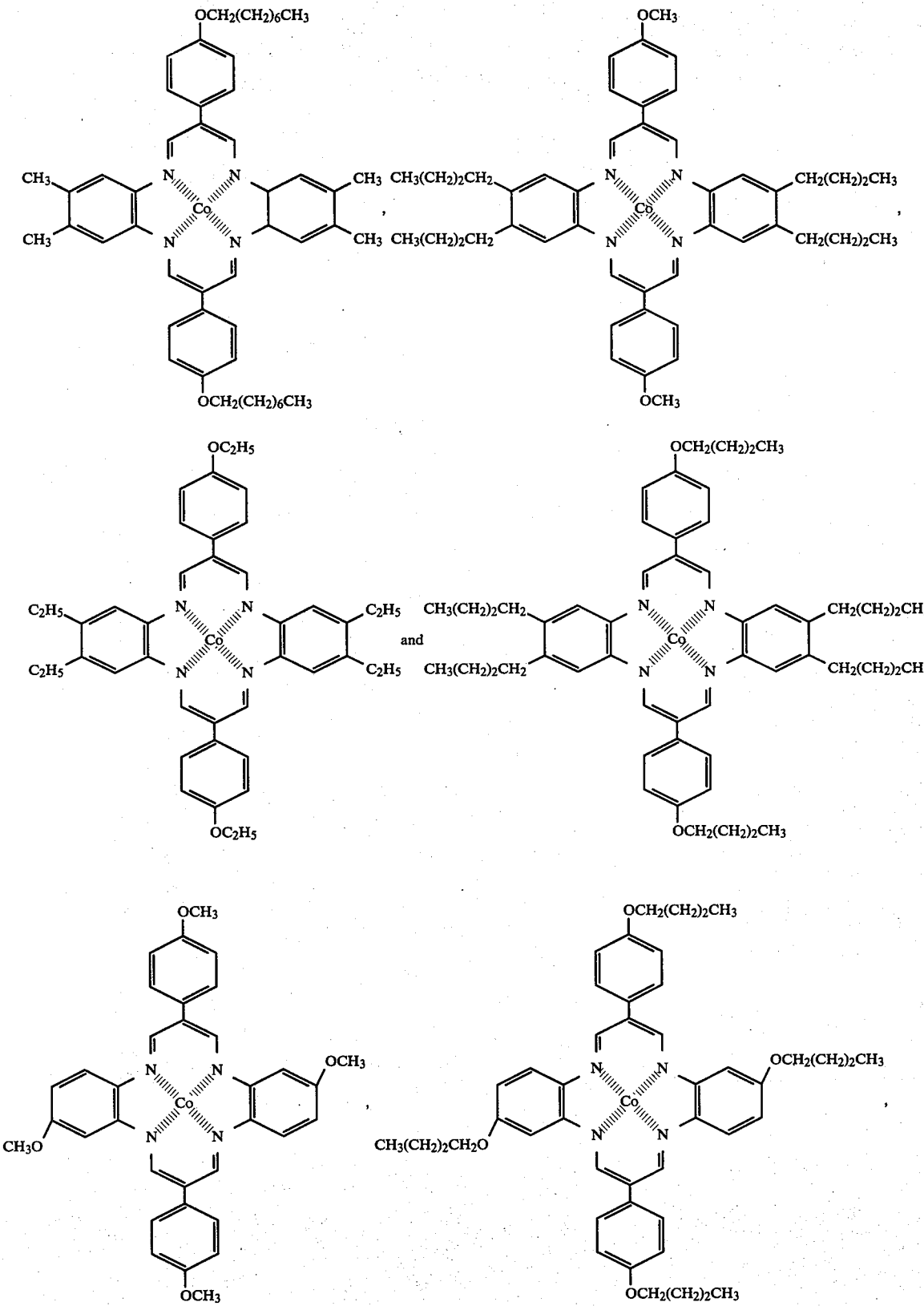

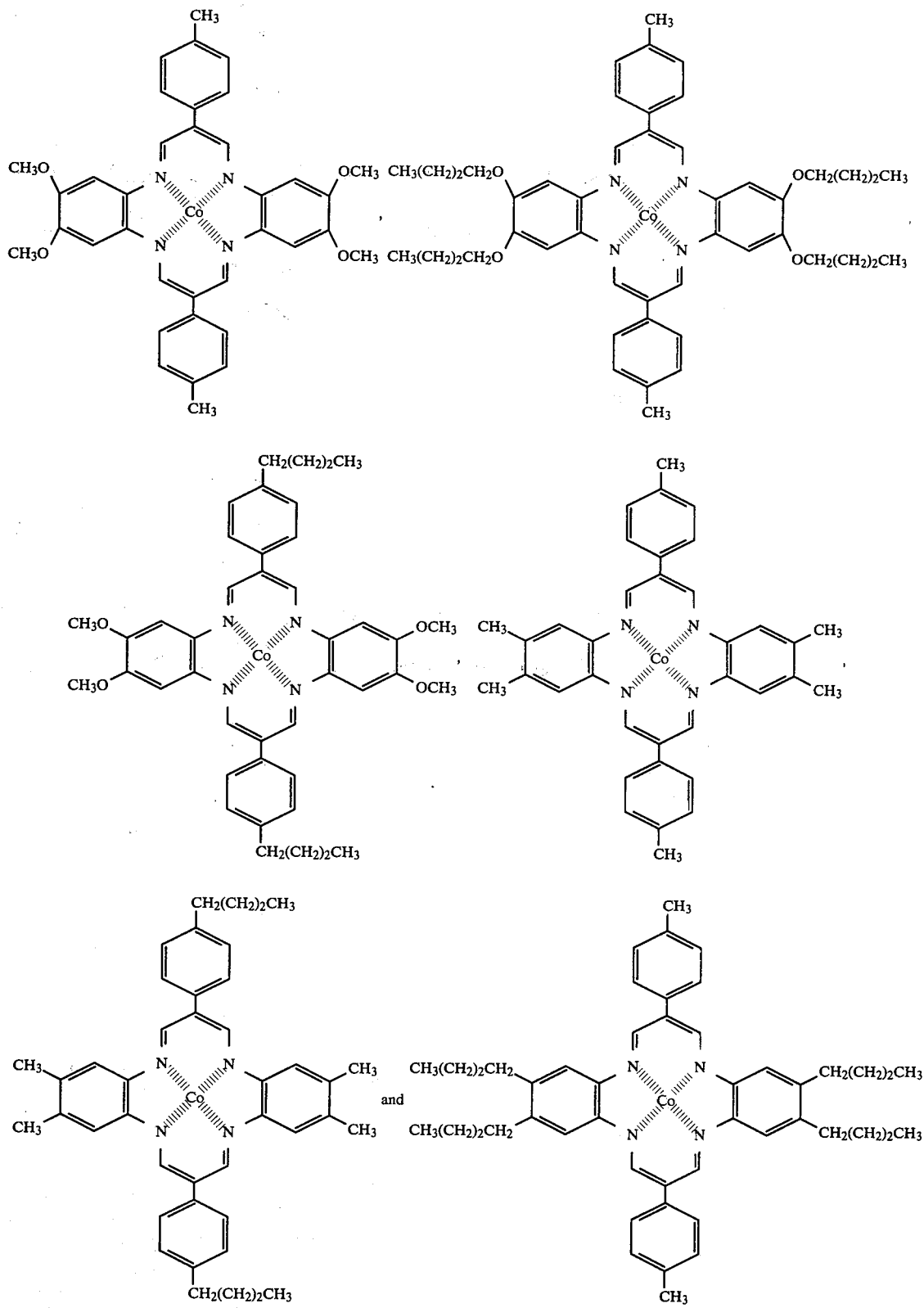
and
The Co-TAA including the novel Co-TAA of this invention, which can be represented by the general formula (II);

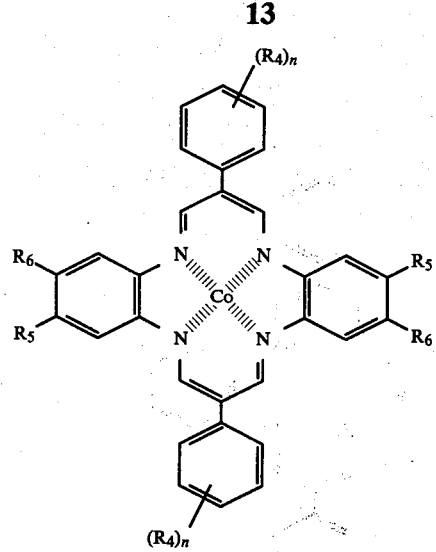

(II)

wherein

R$_4$ is a hydrogen atom, a C$_{1-8}$ alkoxy group, a C$_{1-8}$ alkyl group, a halogen atom, a nitro group, a cyano group, a C$_{1-8}$ acyloxyl group, a hydroxyl group, a carboxyl group, a C$_{1-8}$ alkoxycarbonyl group, a carbamoyl group, a N,N-di C$_{1-6}$ alkylamino group, a C$_{1-8}$ acylamino group, a C$_{1-8}$ alkoxycarbonyl C$_{1-3}$ alkyl group, a N,N-di C$_{1-6}$ alkylamino C$_{1-3}$ alkyl group, or an amino group;

n is integer of 1 to 5; and

R$_5$ and R$_6$ each independently is a hydrogen atom, a C$_{1-8}$ alkoxy group, a C$_{1-8}$ alkyl group, a halogen atom, a nitro group, a cyano group, a C$_{1-8}$ acyloxyl group, a hydroxyl group, a carboxyl group, a C$_{1-8}$ alkoxycarbonyl group, a carbamoyl group, a N,N-di C$_{1-6}$ alkylamino group, a C$_{1-8}$ alkoxycarbonyl C$_{1-3}$ alkyl group, or a C$_{1-8}$ acylamino group;

can be obtained by the following four methods.

Method 1

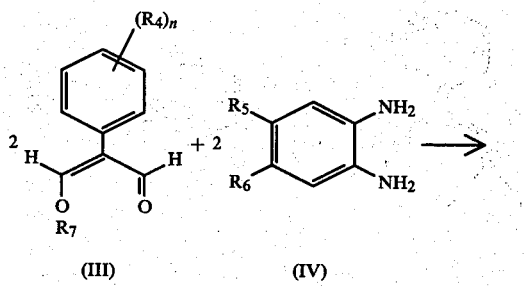

(III)  (IV)

-continued

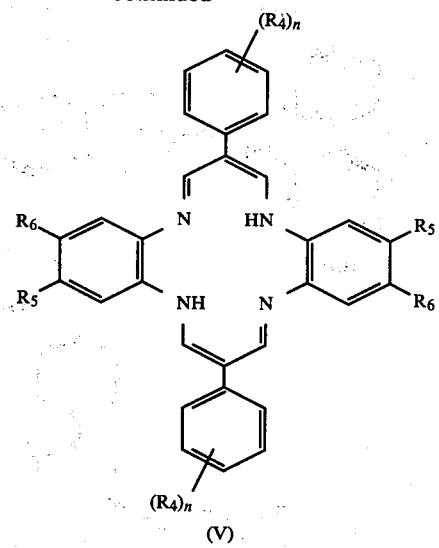

(V)

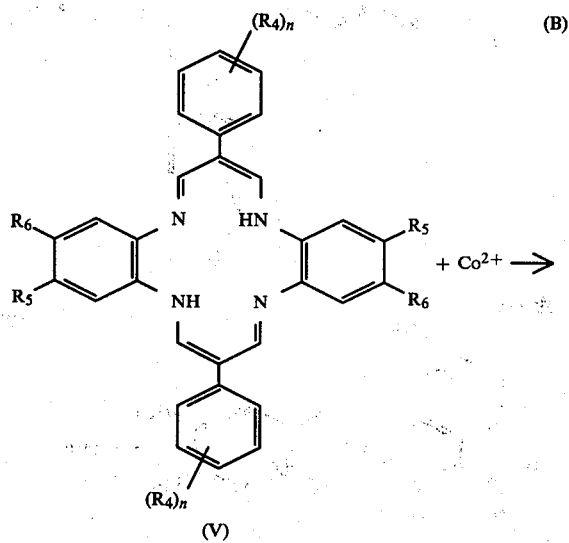

(V)  + Co$^{2+}$ →

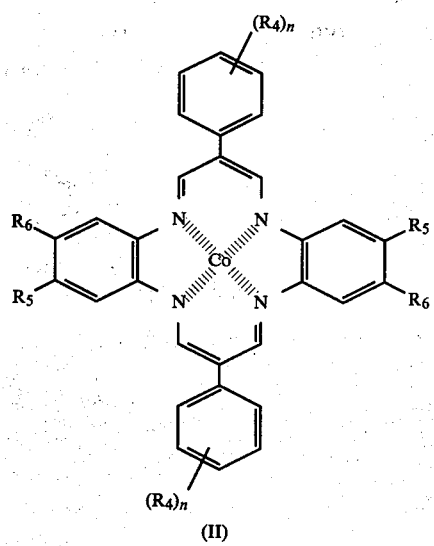

(II)

Method 2

-continued
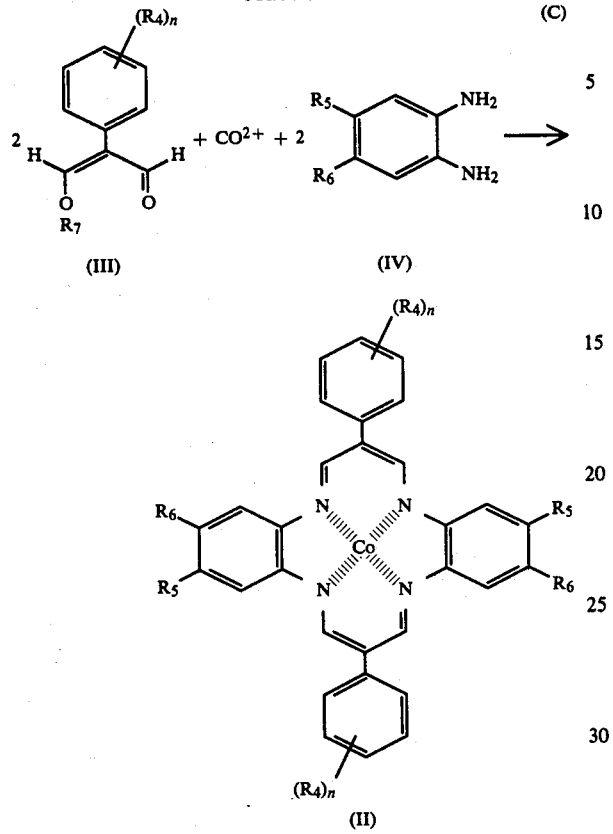
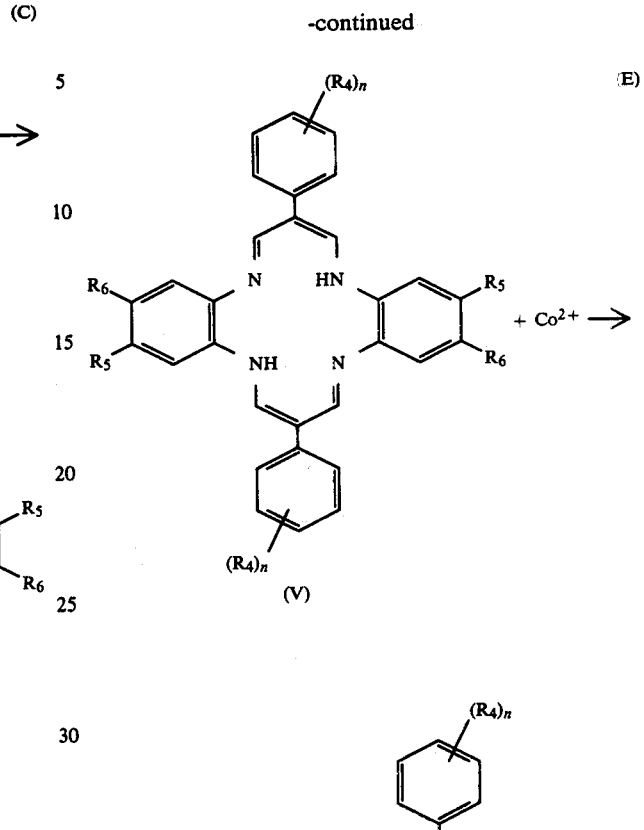

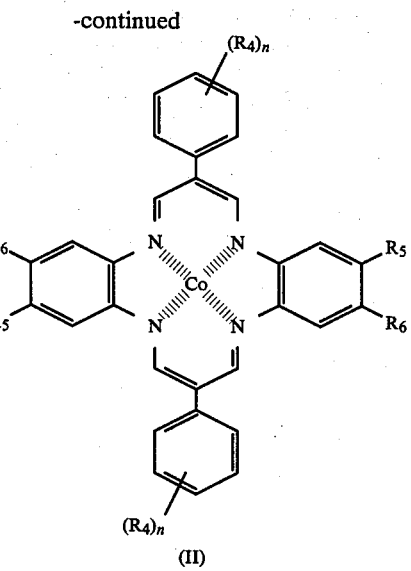

(II)

In the above described formulae (III), (IV), (V) and (VI), $R_4$, $R_5$, $R_6$ and n are the same as defined in the formula (II); $R_7$ is a $C_{1-6}$ alkyl group; and $R_8$ and $R_9$ each independently is a $C_{1-6}$ alkyl group.

According to Method 1, the Co-TAA of the formula (II) can be obtained by reacting a β-alkoxy-α-arylacrolein of the general formula (III) with an o-phenylenediamine derivative of the general formula (IV) to prepare a tetraazaannulene derivative of the formula (V), and then reacting the tetraazaannulene derivative (V) with a cobalt compound.

The reaction (A) between the β-alkoxy-α-arylacrolein (III) and the o-phenylenediamine derivative (IV) can be carried out at 50° C.–250° C. either in the absence of a solvent or in the presence of a solvent. Preferably, the reaction (A) is carried out in the presence of a solvent at around the boiling point of the solvent employed.

Preferred n in the formula (III) of the β-alkoxy-α-arylacroleins which can be employed in the reaction (A) is one.

Preferred $R_4$ in the formula (III) of the β-alkoxy-α-arylacroleins which can be employed in the reaction (A) is in the para position.

Exemplary β-alkoxy-α-arylacroleins (III) which can be employed in the reaction (A) include β-ethoxy-α-phenylacrolein, β-ethoxy-α-(p-nitrophenyl)acrolein, β-ethoxy-α-(p-methoxyphenyl)acrolein, β-ethoxy-α-(p-tolyl)acrolein, β-ethoxy-α-[p-(n-butyl)phenyl]acrolein, β-ethoxy-α-(p-cyanophenyl)acrolein, β-ethoxy-α-(p-chlorophenyl)acrolein, β-ethoxy-α-(p-bromophenyl)acrolein, β-ethoxy-α-[p-(ethoxycarbonyl)phenyl]acrolein, β-ethoxy-α-(p-carboxyphenyl)acrolein, β-ethoxy-α-(p-carbamoylphenyl)acrolein, β-ethoxy-α-(p-hydroxyphenyl)acrolein, β-ethoxy-α-[p-(N,N-dimethylaminomethyl)phenyl]acrolein, β-ethoxy-α-[p-(N,N-dimethylamino)phenyl]acrolein, β-ethoxy-α-[p-(ethoxycarbonylmethyl)phenyl]acrolein and the similar acroleins as described above, whose β-position of the acroleins is a methoxy group, a n-propoxy group, an isopropoxy group, a n-butoxy group, a n-pentyloxy group, a hexyloxy group or a cycrohexyloxy group.

Preferred $R_4$ in the formula (III) of the β-alkoxy-α-arylacroleins which can be employed in the reaction (A) is a hydrogen atom, a methoxy group, a methyl group, a halogen atom, a nitro group, a cyano group or a carboxyl group. Accordingly, preferred β-alkoxy-α-arylacroleins (III) include β-ethoxy-α-phenylacrolein, β-ethoxy-α-(p-nitrophenyl)acrolein, β-ethoxy-α-(p-methoxyphenyl)acrolein, β-ethoxy-α-(p-tolyl)acrolein, β-ethoxy-α-(p-cyanophenyl)acrolein, β-ethoxy-α-(p-chlorophenyl)acrolein, β-ethoxy-α-(p-bromophenyl)acrolein and β-ethoxy-α-(p-carboxyphenyl)acrolein.

The β-alkoxy-α-arylacroleins of the general formula (III) can be obtained by hydrolyzing the β-N,N-dialkylamino-α-arylacrolein of the general formula (VI) and reacting the compound obtained with a $C_{1-6}$ alkyl halide. The methods for preparing the β-alkoxy-α-arylacroleins (III) are easier than those for preparing dithiolium hydrogensulfate which is the starting material of known methods. Therefore, there is a good possibility that the method of this invention will be able to provide various kinds of the Co-TAA.

Exemplary o-phenylenediamine derivatives (IV) which can be employed in the reaction (A) include o-phenylenediamine, 4-($C_{1-8}$ alkoxy)-o-phenylenediamines, 4-($C_{1-8}$ alkyl)-o-phenylenediamines, 4,5-di $C_{1-8}$ alkyl-o-phenylenediamine, 4,5-dichloro-o-phenylenediamine, 4-nitro-o-phenylenediamine, 4-chloro-o-phenylenediamine, 4-carbamoyl-o-phenylenediamine, 4-carboxy-o-phenylenediamine, 4-cyano-o-phenylenediamine, 4-dimethylamino-o-phenylenediamine, 4,5-di $C_{1-8}$ alkoxy-o-phenylenediamine, 4-ethoxycarbonylmethyl-o-phenylenediamine, 4-carboxy-5-methyl-o-phenylenediamine and 4-ethoxycarbonyl-o-phenylenediamine.

Preferred $R_5$ and $R_6$ in the o-phenylenediamine derivatives (IV) which can be employed in the reaction (A) include a hydrogen atom, a methoxy group, a methyl group, a halogen atom, a nitro group and a carboxyl group. Accordingly, preferred o-phenylenediamine derivatives (IV) include o-phenylenediamine, 4-methyl-o-phenylenediamine, 4-chloro-o-phenylenediamine, 4,5-dimethyl-o-phenylenediamine, 4,5-dichloro-o-phenylenediamine, 4-nitro-o-phenylenediamine, 4-methoxy-o-phenylenediamine and 4-carboxy-5-methyl-o-phenylenediamine.

The solvents which can be employed in the reaction (A) include alcohols, phenols, cyclic ethers and non-proton polar organic solvents such as N,N-dimethylformamide, dimethyl sulfoxide, hexamethylphosphorictriamide and N-methylpyrrolidone. The reaction (A) can be preferably carried out in the presence of the non-proton polar organic solvent at around the boiling point of the solvent employed because the desired compounds of the formula (V) can be obtained as pure crystals in a higher yield when the reaction solution is cooled.

The reaction (B) between the tetraazaannulene derivative of the formula (V) as obtained in the reaction (A) and a cobalt compound can be carried out in the presence of a solvent at 50° C.–250° C. Preferably, the reaction (B) is carried out at around the boiling point of the solvent employed.

Exemplary cobalt compounds which can be employed in the reaction (B) include cobalt salts of organic acids such as cobalt (II) carbonate, cobalt (II) acetate, cobalt (II) lactate, cobalt (II) oxalate, cobalt (II) citrate, cobalt (II) tartarate and cobalt (II) gluconate; cobalt salts of inorganic acids such as cobalt (II) chloride, cobalt (II) bromide and cobalt (II) iodide; and cobalt complex salts such as cobalt (II) acetylacetonato.

The solvents which can be employed in the reaction (B) include alcohols, phenols, cyclic ethers and non-proton polar organic solvents such as N,N-dimethylformamide, dimethyl sulfoxide, hexamethylphosphorictriamide and N-methylpyrrolidone. The reaction (B) can be preferably carried out in the presence of the non-proton polar organic solvent at around the boiling point of the solvent employed because the products of the formula (II) can be obtained in the pure form in a higher yield.

According to Method 2, the Co-TAA of the formula (II) can be obtained by reacting a $\beta$-alkoxy-$\alpha$-arylacrolein of the general formula (III) with an o-phenylenediamine derivative of the general formula (IV) in the presence of a cobalt compound.

The reaction (C) among the $\beta$-alkoxy-$\alpha$-arylacrolein (III), the o-phenylenediamine derivative (IV) and the cobalt compound can be carried out at 50° C.–250° C. either in the absence of a solvent or in the presence of a solvent. Preferably, the reaction (C) is carried out in the presence of a solvent at around the boiling point of the solvent employed.

The mol ratio of the $\beta$-alkoxy-$\alpha$-arylacrolein (III): the o-phenylenediamine derivative (IV): the cobalt compound which can be employed in the reaction (C) is 2:2:1.

Preferred n in the $\beta$-alkoxy-$\alpha$-arylacroleins of the formula (III) which can be employed in the reaction (C) is one.

Preferred $R_4$ in the $\beta$-alkoxy-$\alpha$-arylacroleins of the formula (III) which can be employed in the reaction (C) is in the para position.

Exemplary $\beta$-alkoxy-$\alpha$-arylacroleins (III) which can be employed in the reaction (C) include the same acroleins as those employed in the reaction (A) of Method 1.

Preferred $R_4$ in the $\beta$-alkoxy-$\alpha$-arylacroleins of the formula (III) which can be employed in the reaction (C) includes a hydrogen atom, a methoxy group, a methyl group, a halogen atom, a nitro group and a cyano group. Accordingly, preferred $\beta$-alkoxy-$\alpha$-arylacroleins (III) which can be employed in the reaction (C) include $\beta$-ethoxy-$\alpha$-phenylacrolein, $\beta$-ethoxy-$\alpha$-(p-nitrophenyl)acrolein, $\beta$-ethoxy-$\alpha$-(p-methoxyphenyl)acrolein, $\beta$-ethoxy-$\alpha$-(p-tolyl)acrolein, $\beta$-ethoxy-$\alpha$-(p-cyanophenyl)acrolein, $\beta$-ethoxy-$\alpha$-(p-chlorophenyl)acrolein and $\beta$-ethoxy-$\alpha$-(p-bromophenyl)acrolein.

Exemplary o-phenylenediamine derivatives (IV) which can be employed in the reaction (C) include the same o-phenylenediamines as those employed in the reaction (A) of Method 1.

Preferred $R_5$ and $R_6$ in the o-phenylenediamine derivative (IV) which can be employed in the reaction (C) include a hydrogen atom, a methoxy group, a methyl group and a halogen atom. Accordingly, preferred o-phenylenediamine derivatives (IV) include o-phenylenediamine, 4-methyl-o-phenylenediamine, 4-chloro-o-phenylenediamine, 4,5-dimethyl-o-phenylenediamine, 4,5-dichloro-o-phenylenediamine and 4-methoxy-o-phenylenediamine.

Exemplary cobalt compounds and the solvents which can be employed in the reaction (C) include the same as those employed in the reaction (B) of Method 1.

The reaction (C) can be preferably carried out in the presence of the non-proton polar organic solvent at around the boiling point of the solvent employed because the products of the formula (II) can be obtained in the pure form in a higher yield. Further, the yield of the products obtained in Method 2 is higher than that of Method 1.

According to Method 3, the Co-TAA of the formula (II) can be obtained by reacting a $\beta$-N,N-dialkylamino-$\alpha$-arylacrolein of the general formula (VI) with an o-phenylenediamine derivative of the general formula (IV) to prepare a tetraazaannulene derivative of the formula (V), and reacting the tetraazaannulene derivative with a cobalt compound.

The reaction (D) between the $\beta$-N,N-dialkylamino-$\alpha$-arylacrolein (VI) and the o-phenylenediamine derivative (IV) can be carried out at 50° C.–250° C. either in the absence of or in the presence of a solvent. Preferably, the reaction (D) is carried out in the presence of a solvent at around the boiling point of the solvent employed.

Preferred n in the $\beta$-N,N-dialkylamino-$\alpha$-arylacrolein of the formula (VI) which can be employed in the reaction (D) is one.

Preferred $R_4$ in the $\beta$-N,N-dialkylamino-$\alpha$-arylacrolein of the formula (VI) which can be employed in the reaction (D) is in the para position.

Exemplary $\beta$-N,N-dialkylamino-$\alpha$-arylacroleins (VI) which can be employed in the reaction (D) include $\beta$-dimethylamino-$\alpha$-phenylacrolein, $\beta$-dimethylamino-$\alpha$-[p-($C_{1-8}$ alkoxy)phenyl]acroleins, $\beta$-dimethylamino-$\alpha$-[p-($C_{1-8}$ alkyl)phenyl]acroleins, $\beta$-dimethylamino-$\alpha$-(p-nitrophenyl)acrolein, $\beta$-dimethylamino-$\alpha$-[p-(dimethylamino)phenyl]acrolein, $\beta$-dimethylamino-$\alpha$-(p-cyanophenyl)acrolein, $\beta$-dimethylamino-$\alpha$-(p-chlorophenyl)acrolein, $\beta$-dimethylamino-$\alpha$-[p-(ethoxycarbonylmethyl)phenyl]acrolein, $\beta$-dimethylamino-$\alpha$-(p-carboxyphenyl)acrolein, $\beta$-dimethylamino-$\alpha$-(p-carbamoylphenyl)acrolein, $\beta$-dimethylamino-$\alpha$-(p-hydroxyphenyl)acrolein, $\beta$-dimethylamino-$\alpha$-[p-(ethoxycarbonyl)phenyl]acrolein and the similar acroleins as described above, whose $\beta$-position of the acroleins is a diethylamino group, a dipropylamino group, a dibutylamino group, a (N-methyl,N-ethyl)amino group or a (N-methyl,N-butyl)amino group.

Preferred $R_4$ in the $\beta$-N,N-dialkylamino-$\alpha$-arylacroleins (VI) which can be employed in the reaction (D) is a hydrogen atom, a $C_{1-8}$ alkoxy group, a $C_{1-8}$ alkyl group, a nitro group or an ethoxycarbonyl group.

Preferred $R_8$ and $R_9$ in the $\beta$-N,N-dialkylamino-$\alpha$-arylacroleins (VI) which can be employed in the reaction (D) include a methyl group, an ethyl group, a n-propyl group and a n-butyl group.

The $\beta$-N,N-dialkylamino-$\alpha$-arylacroleins of the general formula (VI) can be produced by referring to the methods described in Z. Arnold, Collection of Czechoslov. Chem. Commun. Vol. 26, 3051(1961).

Exemplary o-phenylenediamine derivatives (IV) which can be employed in the reaction (D) include the same o-phenylenediamines as those employed in the reaction (A) of Method 1.

Preferred $R_5$ and $R_6$ in the o-phenylenediamine derivatives (IV) which can be employed in the reaction (D) include a hydrogen atom, a $C_{1-8}$ alkoxy group, a halogen atom and a $C_{1-8}$ alkyl group.

The solvents which can be employed in the reaction (D) include the same solvents as those employed in the reaction (A) of Method 1. The reaction (D) can be preferably carried out in the presence of the non-proton polar organic solvent at around the boiling point of the solvent employed because the compounds of the formula (V) can be obtained in the pure form in a higher yield.

The reaction (E) between the tetraazaannulene derivative of the formula (V) as obtained in the reaction (D) and a cobalt compound can be carried out in the presence of a solvent at 50° C.–250° C. Preferably, the reaction (E) is carried out at around the boiling point of the solvent employed.

The cobalt compounds and the solvents which can be employed in the reaction (E) include the same as those employed in the reaction (B) of Method 1.

The reaction (E) can be preferably carried out in the presence of the non-proton polar organic solvent at around the boiling point of the solvent employed because the products of the formula (II) can be obtained in the pure form in a higher yield.

According to Method 4, the Co-TAA of the formula (II) can be obtained by reacting a β-N,N-dialkylamino-α-arylacrolein of the general formula (VI) with an o-phenylenediamine derivative of the formula (IV) in the presence of a cabalt compound.

The reaction (F) among the β-N,N-dialkylamino-α-arylacrolein (VI), the o-phenylenediamine derivative (IV) and the cobalt compound can be carried out at 50° C.–250° C. either in the absence of or in the presence of a solvent. Preferably, the reaction (F) is carried out in the presence of a solvent at around the boiling point of the solvent employed.

The mol ratio of the β-N,N-dialkylamino-α-arylacrolein (VI): the o-phenylenediamine derivative (IV): the cobalt compound which can be employed in the reaction (F) is 2:2:1.

Preferred n in the β-N,N-dialkylamino-α-arylacroleins (VI) which can be employed in the reaction (F) is one.

Preferred $R_4$ in the β-N,N-dialkylamino-α-arylacroleins (VI) which can be employed in the reaction (F) is in the para position.

Exemplary β-N,N-dialkylamino-α-arylacroleins (VI) which can be employed in the reaction (F) include the same acroleins as those employed in the reaction (D) of Method 3.

Preferred $R_4$ in the β-N,N-dialkylamino-α-arylacroleins of the formula (VI) which can be employed in the reaction (F) is a hydrogen atom, a $C_{1-8}$ alkoxy group, a $C_{1-8}$ alkyl group, a halogen atom, a nitro group, a cyano group or an ethoxycarbonyl group.

Preferred $R_8$ and $R_9$ in the β-N,N-dialkylamino-α-arylacroleins (VI) which can be employed in the reaction (F) include a methyl group, an ethyl group, a n-propyl group and a n-butyl group.

Exemplary o-phenylenediamine derivative (IV) which can be employed in the reaction (F) include the same o-phenylenediamines as those employed in the reaction (D) of Method 3.

Preferred $R_5$ and $R_6$ in the o-phenylenediamine derivatives (IV) which can be employed in the reaction (F) include a hydrogen atom, a $C_{1-8}$ alkoxy group, a $C_{1-8}$ alkyl group and a halogen atom.

Exemplary cobalt compounds and the solvents which can be employed in the reaction (F) include the same as those employed in the reaction (E) of Method 3.

The reaction (F) can be preferably carried out in the presence of the non-proton polar organic solvent at around the boiling point of the solvent employed because the products of the formula (II) can be obtained in the pure form in a higher yield. Further, the yield of the products obtained in Method 4 is higher than that of Method 3.

The novel compound (I) of this invention can be prepared by reacting the β-$C_{1-8}$ alkoxy-α-(p-hydroxyphenyl)acrolein with an o-phenylenediamine derivative (IV) where $R_5$ and $R_6$ each independently is a hydrogen atom, a $C_{1-8}$ alkoxy group or a $C_{1-8}$ alkyl group in the presence of a cobalt compound, and reacting the compound obtained with a $C_{1-8}$ alkyl halide. (Method 5) The reaction (G) among the β-$C_{1-8}$ alkoxy-α-(p-hydroxyphenyl)acrolein, the o-phenylenediamine derivative (IV) and the cobalt compound can be carried out under the same reaction conditions as those of the reaction (F). The reaction between the compound as obtained in the reaction (G) and the $C_{1-8}$ alkyl halide can be carried out in the presence of a solvent for the compound at 25° C.–100° C.

In each of Method 1–5, the products are confirmed as the Co-TAA of the formula (I) or the formula (II), or the tetraazaannulene derivatives of the formula (V) by the value of physical properties such as elementary analysis, Mass spectra and visible spectra of the products obtained.

The Co-TAA of the formulae (I) and (II) are useful as an oxygen reduction catalyst and the tetraazaannulene derivatives of the formula (V) are useful as the intermediate of the Co-TAA.

The following examples illustrate the present invention in more detail, but they are given for illustrative purposes only and are not to be construed as limiting the invention.

EXAMPLE 1

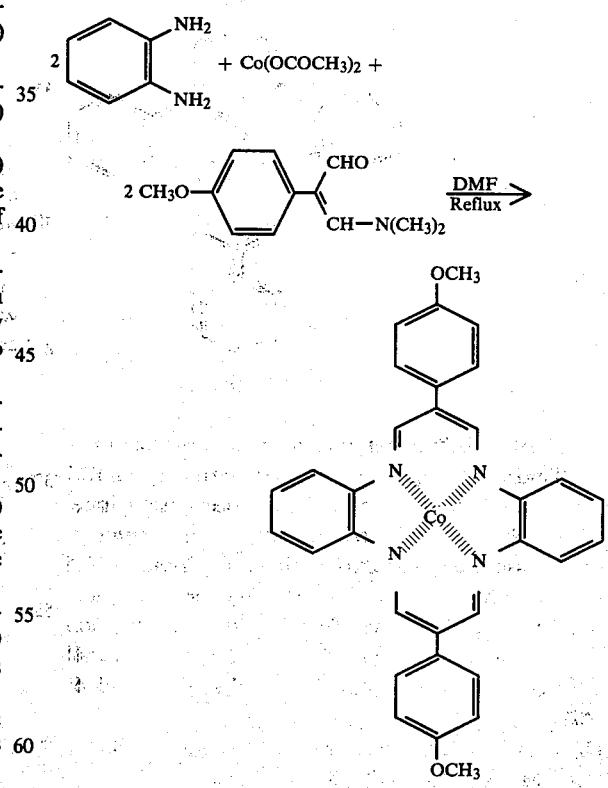

In 20 ml of N,N-dimethylformamide were dissolved 5 millimol (540 mg) of o-phenylenediamine and 2.5 millimol (623 mg) of cobalt (II) acetate tetrahydrate, and the solution was heated at 120° C. for 30 minutes. The solution was added with 5 millimol (1025 mg) of β-dimethylamino-α-(p-methoxyphenyl)acrolein and refluxed under heating for 3 hours. The reaction solution was cooled, filtered, washed with methanol and dried to give dark purple crystals in a yield of 60.0%.

The crystals have the following physical values.
Mass Spectrum: Calcd.: 557.5. Found: 557.
Elementary Analysis: Calcd.: C:H:N=68.94:4.70:10.05. Found: C:H:N=68.83:4.76:10.25.
Visible Spectrum (nm) [in DMF]: 380(s)*, 397, 429(s) and 522
*: (s) means a shoulder of a peak.

EXAMPLE 2

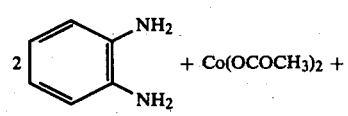

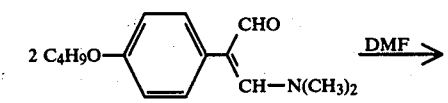

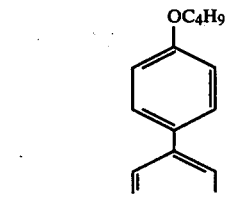

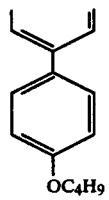

In 10 ml of N,N-dimethylformamide were dissolved 2.5 millimol (270 mg) of o-phenylenediamine and 1.25 millimol (312 mg) of cobalt (II) acetate tetrahydrate, and the solution was heated at 120° C. for 30 minutes. Then, the solution was added with 2.5 millimol (612.5 mg) of β-dimethylamino-α-(p-n-butoxyphenyl)acrolein and refluxed under heating for 3 hours. The reaction solution was cooled, filtered, washed with methanol and dried to give dark purple crystals in a yield of 45.4%.

The crystals have the following physical values.
Mass Spectrum: Calcd.: 641.7. Found: 641.
Elementary Analysis: Calcd.: C:H:N=71.13:5.97:8.73. Found: C:H:N=70.95:6.01:8.77.
Visible Spectrum (nm) [in DMF]: 380(s)*, 397, 429(s) and 522.
*: (s) means a shoulder of a peak.

EXAMPLE 3

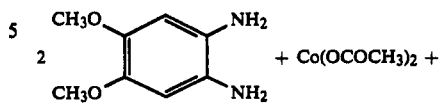

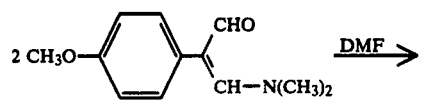

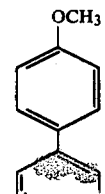

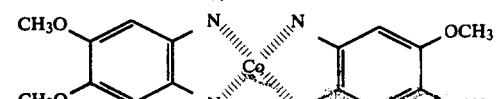

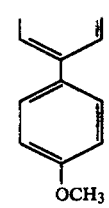

In 10 ml of N,N-dimethylformamide were dissolved 2.5 millimol (420 mg) of 4,5-dimethoxy-o-phenylenediamine, 1.25 millimol (312 mg) of cobalt (II) acetate tetrahydrate and 2.5 millimol (513 mg) of β-dimethylamino-α-(p-methoxyphenyl)acrolein, and the solution was refluxed under heating in an argon gas atmosphere for 5 hours. The reaction solution was cooled, filtered, washed with methanol and dried to give dark purple crystals in a yield of 17.0%.

The crystals have the following physical values.
Mass Spectrum: Calcd.: 667.6. Found: 667.
Elementary Analysis: Calcd.: C:H:N=63.81:5.06:8.27. Found: C:H:N=63.77:4.88:8.40.
Visible Spectrum (nm) [in DMF]: 384, 395(s)*, 430, 457 and 525.
*: (s) means a shoulder of a peak.

EXAMPLE 4

Step 1

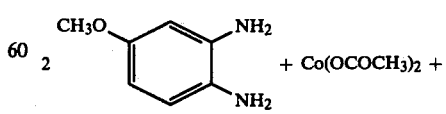

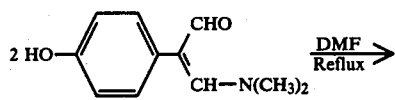

Step 1

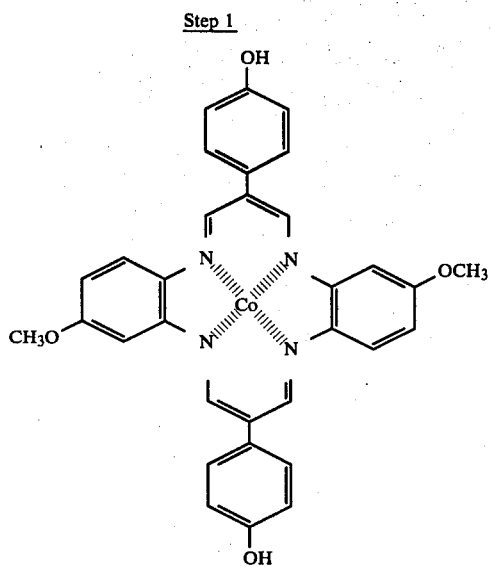

In 20 ml of N,N-dimethylformamide were dissolved 5 millimol (690 mg) of 4-methoxy-o-phenylenediamine and 2.5 millimol (625 mg) of cobalt (II) acetate tetrahydrate, and the solution was heated at 120° C. for 30 minutes. Then, the solution was added with 5 millimol (955 mg) of β-dimethylamino-α-(p-hydroxyphenyl)acrolein, and refluxed under heating in an argon gas atmosphere for 5 hours. The reaction solution was cooled and added with methanol to precipitated crystals. The crystals were separated by filtration, washed with methanol and dried. The yield was 7.5%.

Step 2

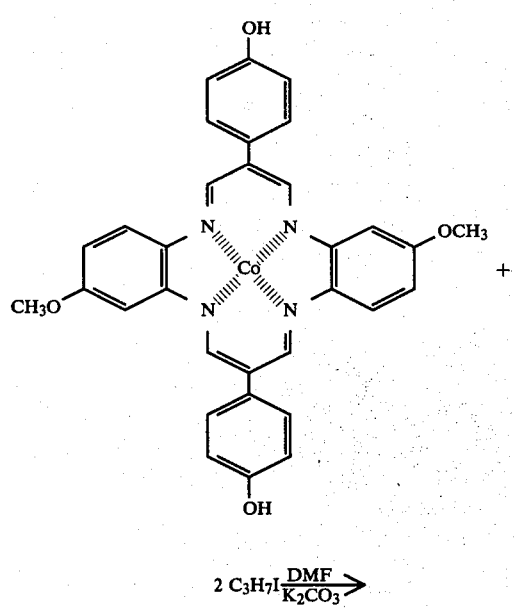

Step 2

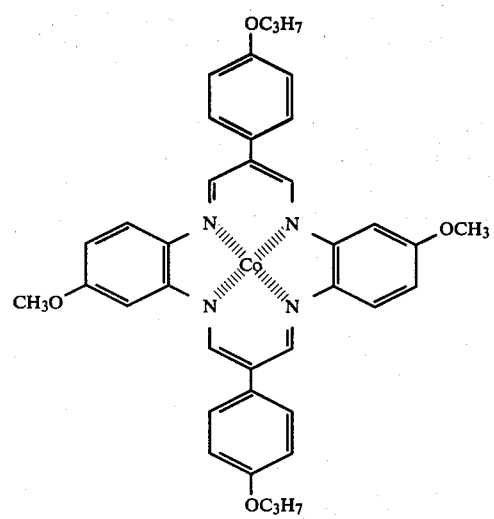

In 10 ml of N,N-dimethylformamide was dissolved the crystals obtained in Step 1. To the solution obtained were added 6 times amount of propyl iodide based on the millimol of the crystals and 6 times amount of potassium carbonate based on the millimol of the crystals. Then, the mixture was stirred at 25° C. for 12 hours. To the reaction mixture was added excess of water to precipitated crystals. The crystals were obtained by filtration, washed with methanol and dried to give dark purple crystals in a yield of 50%.

The crystals have the following physical values.

Mass Spectrum: Calcd.: 673.7. Found: 673.

Elementary Analysis: Calcd.: C:H:N=67.75:5.69:8.32. Found: C:H:N=68.01:5.55:8.25.

Visible Spectrum (nm) [in DMF]: 399, 420(s)*, 443(s), 388(s) and 520

*: (s) means a shoulder of a peak.

EXAMPLE 5

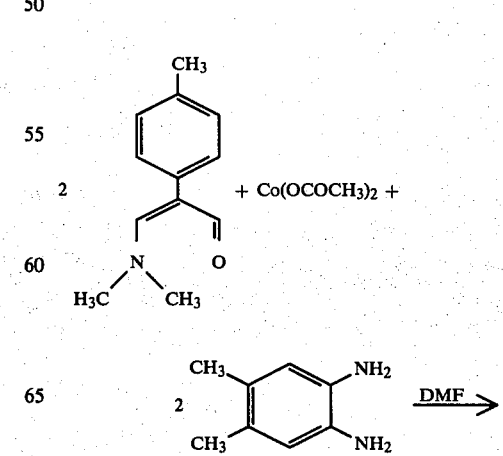

-continued

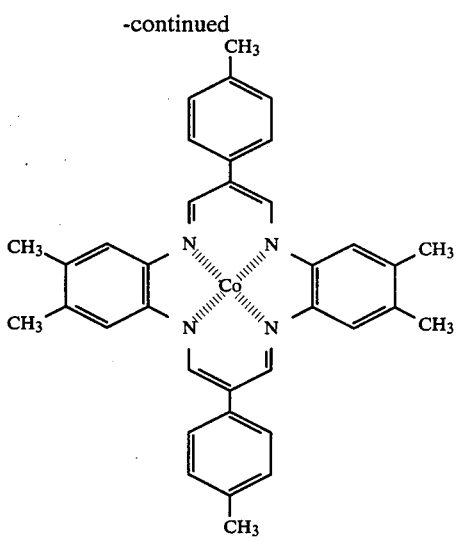

In 10 ml of N,N-dimethylformamide were dissolved 2.5 millimol (473 mg) of β-dimethylamino-α-(p-methylphenyl)acrolein, 1.25 millimol (312 mg) of cobalt (II) acetate tetrahydrate and 2.5 millimol (340 mg) of 4,5-dimethyl-o-phenylenediamine, and the solution was refluxed under heating for 5 hours. The reaction solution was cooled, filtered, washed with methanol and dried to give brown crystals in a yield of 68.8%.

The crystals have the following physical values.
Mass Spectrum: Calcd.: 581.6. Found: 581.
Elementary Analysis: Calcd.: C:H:N=74.34:5.89:9.63. Found: C:H:N=74.43:5.87:9.61.
Visible Spectrum (nm) [in DMF]: 384, 398, 423, 440(s)* and 524
*: (s) means a shoulder of a peak.

EXAMPLES 6~209

Co-TAA of this invention was prepared by the methods as shown in Table 1. The results are also shown in Table 1.

TABLE 1-1

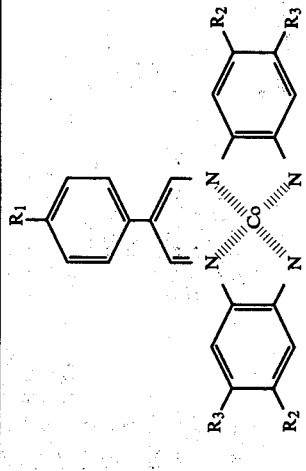

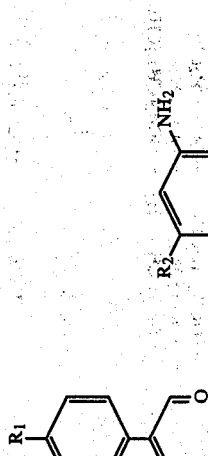

| Example No. | H₃C R₁ (R₁) | R₂ | R₃ | Diamine R₂ | Diamine R₃ | Example No. of Reaction Conditions | Yield (%) | Crystal Color | Product R₁ | Product R₂ | Product R₃ |
|---|---|---|---|---|---|---|---|---|---|---|---|
| 6 | —OC₂H₅ | —H | —H | —H | —H | 2 | 43.6 | Dark Purple | —OC₂H₅ | —H | —H |
| 7 | —OCH₂CH₂CH₃ | —H | —H | —OCH₃ | —H | 2 | 42.2 | " | —OCH₂CH₂CH₃ | —H | —OCH₃ |
| 8 | —H | —OCH₃ | —H | —OCH₃ | —H | 1 | 8.9 | " | —H | —OCH₃ | —H |
| 9 | —H | —OC₂H₅ | —H | —OC₂H₅ | —H | 3 | 7.7 | " | —H | —OC₂H₅ | —H |
| 10 | —OCH(CH₃)₂ | —H | —H | —H | —H | 2 | 40.7 | " | —OCH(CH₃)₂ | —H | —H |
| 11 | —OCH(CH₃)CH₂CH₃ | —H | —H | —H | —H | 2 | 44.1 | " | —OCH(CH₃)CH₂CH₃ | —H | —H |
| 12 | —OCH₂CH(CH₃)₂ | —H | —H | —H | —H | 2 | 46.3 | Reddish Purple | —OCH₂CH(CH₃)₂ | —H | —H |
| 13 | —H | —OCH₃ | —OCH₃ | —OCH₃ | —H | 3 | 0.52 | Dark Purple | —H | —OCH₃ | —OCH₃ |
| 14 | —H | —OCH₂CH₃ | —OCH₂CH₃ | —OCH₃ | —H | 3 | 6.2 | " | —H | —OCH₂CH₃ | —H |
| 15 | —H | —OCH₂(CH₂)₂CH₃ | —OCH₂(CH₂)₂CH₃ | —OCH₃ | —H | 3 | 9.8 | Reddish Purple | —H | —OCH₂(CH₂)₂CH₃ | —H |
| 16 | —H | —OC₂H₅ | —OC₂H₅ | —OC₂H₅ | —H | 3 | 0.95 | " | —H | —OC₂H₅ | —OC₂H₅ |
| 17 | —H | —OCH₂CH₃ | —OCH₂CH₃ | —OCH₂CH₃ | —OCH₂CH₃ | 3 | 1.4 | Dark Purple | —H | —OCH₂CH₃ | —OCH₂CH₃ |
| 18 | —H | —OCH₂(CH₂)₂CH₃ | —OCH₂(CH₂)₂CH₃ | —OCH₂(CH₂)₂CH₃ | —H | 3 | 1.0 | Reddish Purple | —H | —OCH₂(CH₂)₂CH₃ | —H |
| 19 | —OCH₃ | —OCH₃ | —H | —OCH₃ | —H | 1 | 15.0 | " | —OCH₃ | —OCH₃ | —H |
| 20 | —OCH₃ | —OC₂H₅ | —H | —OC₂H₅ | —H | 3 | 13.2 | " | —OCH₃ | —OC₂H₅ | —H |
| 21 | —OCH₃ | —OCH₂CH₂CH₃ | —H | —OCH₂CH₂CH₃ | —H | 3 | 12.6 | " | —OCH₃ | —OCH₂CH₂CH₃ | —H |
| 22 | —OCH₃ | —OCH(CH₃)₂ | —H | —OCH(CH₃)₂ | —H | 3 | 11.5 | " | —OCH₃ | —OCH(CH₃)₂ | —H |
| 23 | —OCH₃ | —OCH₂(CH₂)₂CH₃ | —H | —OCH₂(CH₂)₂CH₃ | —H | 3 | 18.8 | " | —OCH₃ | —OCH₂(CH₂)₂CH₃ | —H |
| 24 | —OCH₃ | —OCH(CH₃)CH₂CH₃ | —H | —H | —H | 3 | 15.3 | " | —OCH₃ | —OCH(CH₃)CH₂CH₃ | —H |

TABLE 1-1-continued

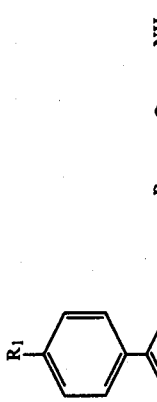

| Example No. | H₃C R₁ (aldehyde) | R₂ | R₃ | Example No. of Reaction Conditions | Yield (%) | Crystal Color | R₁ | R₂ | R₃ |
|---|---|---|---|---|---|---|---|---|---|
| 25 | —OCH₃ | —OCH₂CH(CH₃)₂ | —H | 3 | 17.7 | " | —OCH₃ | —OCH₂CH(CH₃)₂ | —H |
| 26 | —OCH₃ | —OC(CH₃)₃ | —H | 3 | 10.6 | " | —OCH₃ | —OC(CH₃)₃ | —H |
| 27 | —OCH₃ | —OC₂H₅ | —OC₂H₅ | 3 | 3.0 | Dark Purple | —OCH₃ | —OC₂H₅ | —OC₂H₅ |
| 28 | —OCH₃ | —OCH₂CH₂CH₃ | —OCH₂CH₂CH₃ | 3 | 14.4 | " | —OCH₃ | —OCH₂CH₂CH₃ | —OCH₂CH₂CH₃ |
| 29 | —OCH₃ | —OCH(CH₃)₂ | —OCH(CH₃)₂ | 3 | 9.6 | " | —OCH₃ | —OCH(CH₃)₂ | —OCH(CH₃)₂ |
| 30 | —OCH₃ | —OCH₂(CH₂)₂CH₃ | —OCH₂(CH₂)₂CH₃ | 3 | 7.5 | Dark Brown | —OCH₃ | —OCH₂(CH₂)₂CH₃ | —OCH₂(CH₂)₂CH₃ |
| 31 | —OCH₃ | CH₃—OCHCH₂CH₃ | —OCHCH₂CH₃ / CH₃ | 3 | 6.3 | " | —OCH₃ | CH₃—OCHCH₂CH₃ | —OCHCH₂CH₃ / CH₃ |
| 32 | —OCH₃ | —OCH₂CH(CH₃)₂ | —OCH₂CH(CH₃)₂ | 3 | 7.9 | " | —OCH₃ | —OCH₂CH(CH₃)₂ | —OCH₂CH(CH₃)₂ |
| 33 | —OC₂H₅ | —OCH₃ | —H | 3 | 6.6 | Reddish Purple | —OC₂H₅ | —OCH₃ | —H |
| 34 | —OC₂H₅ | —OC₂H₅ | —H | 3 | 14.2 | " | —OC₂H₅ | —OC₂H₅ | —H |
| 35 | —OC₂H₅ | —OCH₂CH₂CH₃ | —H | 3 | 5.9 | " | —OC₂H₅ | —OCH₂CH₂CH₃ | —H |
| 36 | —OC₂H₅ | —OCH(CH₃)₂ | —H | 3 | 4.8 | " | —OC₂H₅ | —OCH(CH₃)₂ | —H |
| 37 | —OC₂H₅ | —OCH₂(CH₂)₂CH₃ | —H | 3 | 7.3 | Dark Purple | —OC₂H₅ | —OCH₂(CH₂)₂CH₃ | —H |
| 38 | —OC₂H₅ | —OCH₃ | —OCH₃ | 3 | 15.2 | Dark Purple | —OC₂H₅ | —OCH₃ | —OCH₃ |
| 39 | —OC₂H₅ | —OC₂H₅ | —OC₂H₅ | 3 | 10.5 | " | —OC₂H₅ | —OC₂H₅ | —OC₂H₅ |
| 40 | —OC₂H₅ | —OCH₂CH₂CH₃ | —OCH₂CH₂CH₃ | 3 | 7.5 | Dark Brown | —OC₂H₅ | —OCH₂CH₂CH₃ | —OCH₂CH₂CH₃ |
| 41 | —OC₂H₅ | —OCH₂(CH₂)₂CH₃ | —OCH₂(CH₂)₂CH₃ | 3 | 4.8 | " | —OC₂H₅ | —OCH₂(CH₂)₂CH₃ | —OCH₂(CH₂)₂CH₃ |
| 42 | —OCH₂CH₂CH₃ | —OC₂H₅ | —H | 3 | 5.2 | Reddish Purple | —OCH₂CH₂CH₃ | —OC₂H₅ | —H |
| 43 | —OCH₂CH₂CH₃ | —OCH₂(CH₂)₂CH₃ | —H | 3 | 16.8 | " | —OCH₂CH₂CH₃ | —OCH₂(CH₂)₂CH₃ | —H |
| 44 | —OCH₂CH₂CH₃ | —OCH₂(CH₂)₂CH₃ | —H | 3 | 6.5 | Dark Purple | —OCH₂CH₂CH₃ | —OCH₂(CH₂)₂CH₃ | —H |
| 45 | —OCH₂CH₂CH₃ | —OCH₃ | —OCH₃ | 3 | 9.8 | " | —OCH₂CH₂CH₃ | —OCH₃ | —OCH₃ |
| 46 | —OCH₂CH₂CH₃ | —OC₂H₅ | —OC₂H₅ | 3 | 2.3 | Dark Purple | —OCH₂CH₂CH₃ | —OC₂H₅ | —OC₂H₅ |
| 47 | —OCH₂CH₂CH₃ | —OCH₂CH₂CH₃ | —OCH₂CH₂CH₃ | 3 | 8.1 | Dark Brown | —OCH₂CH₂CH₃ | —OCH₂CH₂CH₃ | —OCH₂CH₂CH₃ |

TABLE 1-1-continued

| Example No. | R$_1$ (aldehyde) | R$_2$ (aldehyde) | R$_3$ (diamine) | Example No. of Reaction Conditions | Yield (%) | Crystal Color | R$_1$ | R$_2$ | R$_3$ |
|---|---|---|---|---|---|---|---|---|---|
| 48 | —OCH$_2$CH$_2$CH$_3$ | —OCH$_2$(CH$_2$)$_2$CH$_3$ | —OCH$_2$(CH$_2$)$_2$CH$_3$ | 3 | 3.2 | " | —OCH$_2$(CH$_2$)$_2$CH$_3$ | —OCH$_2$(CH$_2$)$_2$CH$_3$ | —OCH$_2$(CH$_2$)$_2$CH$_3$ |
| 49 | —OCH(CH$_3$)$_2$ | —OCH$_3$ | —H | 3 | 7.8 | Reddish Purple | —OCH(CH$_3$)$_2$ | —OCH$_3$ | —H |
| 50 | —OCH(CH$_3$)$_2$ | —OCH(CH$_3$)$_2$ | —H | 3 | 6.2 | " | —OCH(CH$_3$)$_2$ | —OCH(CH$_3$)$_2$ | —H |
| 51 | —OCH(CH$_3$)$_2$ | —OCH$_3$ | —OCH$_3$ | 3 | 8.7 | Dark Purple | —OCH(CH$_3$)$_2$ | —OCH$_3$ | —OCH$_3$ |
| 52 | —OCH$_2$(CH$_2$)$_2$CH$_3$ | —OCH$_3$ | —H | 3 | 47.0 | Reddish Purple | —OCH$_2$(CH$_2$)$_2$CH$_3$ | —OCH$_3$ | —H |
| 53 | —OCH$_2$(CH$_2$)$_2$CH$_3$ | —OC$_2$H$_5$ | —H | 3 | 10.1 | Dark Brown | —OCH$_2$(CH$_2$)$_2$CH$_3$ | —OC$_2$H$_5$ | —H |
| 54 | —OCH$_2$(CH$_2$)$_2$CH$_3$ | —OCH$_2$CH$_2$CH$_3$ | —H | 3 | 11.0 | Dark Brown | —OCH$_2$(CH$_2$)$_2$CH$_3$ | —OCH$_2$(CH$_2$)$_2$CH$_3$ | —H |
| 55 | —OCH$_2$(CH$_2$)$_2$CH$_3$ | —OCH$_2$(CH$_2$)$_2$CH$_3$ | —H | 3 | 13.3 | " | —OCH$_2$(CH$_2$)$_2$CH$_3$ | —OCH$_2$(CH$_2$)$_2$CH$_3$ | —H |
| 56 | —OCH$_2$(CH$_2$)$_2$CH$_3$ | —OCH$_3$ | —OCH$_3$ | 3 | 5.3 | " | —OCH$_2$(CH$_2$)$_2$CH$_3$ | —OCH$_3$ | —OCH$_3$ |
| 57 | —OCH$_2$(CH$_2$)$_2$CH$_3$ | —OC$_2$H$_5$ | —OC$_2$H$_5$ | 3 | 1.9 | " | —OCH$_2$(CH$_2$)$_2$CH$_3$ | —OC$_2$H$_5$ | —OC$_2$H$_5$ |
| 58 | —OCH$_2$(CH$_2$)$_2$CH$_3$ | —OCH$_2$CH$_2$CH$_3$ | —OCH$_2$CH$_2$CH$_3$ | 3 | 4.7 | " | —OCH$_2$(CH$_2$)$_2$CH$_3$ | —OCH$_2$CH$_2$CH$_3$ | —OCH$_2$CH$_2$CH$_3$ |
| 59 | —OCH$_2$(CH$_2$)$_2$CH$_3$ | —OCH$_2$(CH$_2$)$_2$CH$_3$ | —OCH$_2$(CH$_2$)$_2$CH$_3$ | 3 | 6.9 | " | —OCH$_2$(CH$_2$)$_2$CH$_3$ | —OCH$_2$(CH$_2$)$_2$CH$_3$ | —OCH$_2$(CH$_2$)$_2$CH$_3$ |
| 60 | CH$_3$—OCH$_2$CH$_3$ | —OCH$_3$ | —H | 3 | 37.8 | Reddish Purple | CH$_3$—OCH$_2$CH$_3$ | —OCH$_3$ | —H |
| 61 | CH$_3$—OCH$_2$CH$_3$ | CH$_3$—OCH$_2$CH$_3$ | —H | 3 | 8.1 | Dark Purple | CH$_3$—OCH$_2$CH$_3$ | CH$_3$—OCH$_2$CH$_3$ | —H |
| 62 | CH$_3$—OCH$_2$CH$_3$ | —OCH$_3$ | —OCH$_3$ | 3 | 7.2 | Dark Brown | CH$_3$—OCH$_2$CH$_3$ | —OCH$_3$ | —OCH$_3$ |
| 63 | —OCH$_2$CH(CH$_3$)$_2$ | —OCH$_3$ | —H | 3 | 42.7 | Reddish Purple | —OCH$_2$CH(CH$_3$)$_2$ | —OCH$_3$ | —H |
| 64 | —OCH$_2$CH(CH$_3$)$_2$ | —OCH$_2$CH(CH$_3$)$_2$ | —H | 3 | 12.4 | Dark Purple | —OCH$_2$CH(CH$_3$)$_2$ | —OCH$_2$CH(CH$_3$)$_2$ | —H |
| 65 | —OCH$_2$CH(CH$_3$)$_2$ | —OCH$_3$ | —OCH$_3$ | 3 | 10.3 | Dark Brown | —OCH$_2$CH(CH$_3$)$_2$ | —OCH$_3$ | —OCH$_3$ |

TABLE 1-1-continued

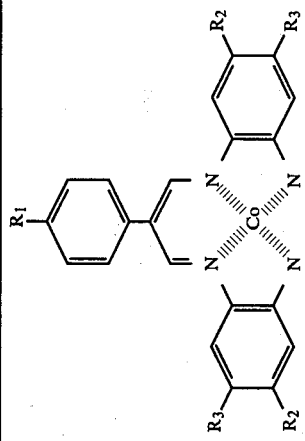

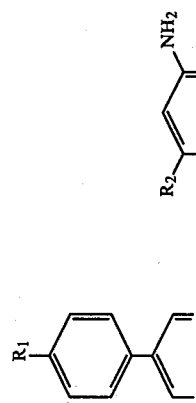

| Example No. | Aldehyde R1 | Aldehyde R2 | Diamine R2 | Diamine R3 | Example No. of Reaction Conditions | Yield (%) | Crystal Color | Product R1 | Product R2 | Product R3 |
|---|---|---|---|---|---|---|---|---|---|---|
| 66 | —OC(CH3)3 | —H | —H | —H | 2 | 33.2 | Dark Purple | —OC(CH3)3 | —H | —H |
| 67 | —OC(CH3)3 | —OCH3 | —OCH3 | —H | 3 | 27.3 | " | —OC(CH3)3 | —OCH3 | —H |
| 68 | —OC(CH3)3 | —OCH3 | —OCH3 | —OCH3 | 3 | 5.9 | Dark Brown | —OC(CH3)3 | —OCH3 | —OCH3 |
| 69 | —OCH2(CH2)3CH3 | —H | —H | —H | 3 | 46.2 | Dark Purple | —OCH2(CH2)3CH3 | —H | —H |
| 70 | —OCH2(CH2)6CH3 | —H | —H | —H | 3 | 38.9 | Dark Purple | —OCH2(CH2)6CH3 | —H | —H |
| 71 | —H | —OCH2(CH2)3CH3 | —OCH2(CH2)3CH3 | —H | 3 | 10.3 | " | —H | —OCH2(CH2)3CH3 | —H |
| 72 | —H | —OCH2(CH2)6CH3 | —OCH2(CH2)6CH3 | —H | 3 | 6.5 | Brown | —H | —OCH2(CH2)6CH3 | —H |
| 73 | —OCH2(CH2)3CH3 | —OCH3 | —OCH3 | —H | 3 | 28.1 | Dark Brown | —OCH2(CH2)3CH3 | —OCH3 | —H |
| 74 | —OCH2(CH2)6CH3 | —OCH3 | —OCH3 | —H | 3 | 23.6 | Reddish Brown | —OCH2(CH2)6CH3 | —OCH3 | —H |
| 75 | —OCH3 | —OCH2(CH2)3CH3 | —OCH2(CH2)3CH3 | —H | 3 | 31.8 | Brown | —OCH3 | —OCH2(CH2)3CH3 | —H |
| 76 | —OCH3 | —OCH2(CH2)6CH3 | —OCH2(CH2)6CH3 | —H | 3 | 25.5 | Dark Brown | —OCH3 | —OCH2(CH2)6CH3 | —H |
| 77 | —OCH(CH3)2 | —OCH(CH3)2 | —OCH(CH3)2 | —H | 3 | 13.7 | Dark Brown | —OCH(CH3)2 | —OCH(CH3)2 | —H |
| 78 | —OCH(CH3)2 | —OCH2(CH2)3CH3 | —OCH2(CH2)3CH3 | —H | 3 | 11.0 | Dark Brown | —OCH(CH3)2 | —OCH2(CH2)3CH3 | —H |
| 79 | —OCH(CH3)2 | —OCH2(CH2)6CH3 | —OCH2(CH2)6CH3 | —H | 3 | 18.9 | " | —OCH(CH3)2 | —OCH(CH3)2 | —H |
| 80 | —OCH(CH3)2 | —OCH2(CH2)6CH3 | —OCH2(CH2)6CH3 | —H | 3 | 15.3 | " | —OCH(CH3)2 | —OCH2(CH2)6CH3 | —H |
| 81 | —OCH(CH3)CH2CH3 | —OCH2(CH2)3CH3 | —OCH2(CH2)3CH3 | —H | 3 | 21.2 | " | —OCH(CH3)CH2CH3 | —OCH2(CH2)3CH3 | —H |
| 82 | —OCH(CH3)CH2CH3 | —OCH2(CH2)6CH3 | —OCH2(CH2)6CH3 | —H | 3 | 12.3 | " | —OCH(CH3)CH2CH3 | —OCH2(CH2)6CH3 | —H |
| 83 | —OCH2(CH2)3CH3 | —OCH(CH3)CH2CH3 | —OCH(CH3)CH2CH3 | —H | 3 | 14.3 | " | —OCH2(CH2)3CH3 | —OCH(CH3)CH2CH3 | —H |

TABLE 1-1-continued

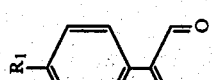

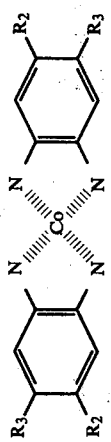

| Example No. | $R_1$ | $R_2$ | $R_3$ | Example No. of Reaction Conditions | Yield (%) | Crystal Color | $R_1$ | $R_2$ | $R_3$ |
|---|---|---|---|---|---|---|---|---|---|
| 84 | —OCH$_2$(CH$_2$)$_6$CH$_3$ | CH$_3$<br>—OCH$_2$CH$_3$ | —H | 3 | 10.6 | " | —OCH$_2$(CH$_2$)$_6$CH$_3$ | CH$_3$<br>—OCHCH$_2$CH$_3$ | —H |
| 85 | —OCH$_2$CH(CH$_3$)$_2$ | —OCH$_2$(CH$_2$)$_3$CH$_3$ | —H | 3 | 18.7 | " | —OCH$_2$CH(CH$_3$)$_2$ | —OCH$_2$(CH$_2$)$_3$CH$_3$ | —H |
| 86 | —OCH$_2$CH(CH$_3$)$_2$ | —OCH$_2$(CH$_2$)$_6$CH$_3$ | —H | 3 | 14.5 | Dark Brown | —OCH$_2$CH(CH$_3$)$_2$ | —OCH$_2$(CH$_2$)$_6$CH$_3$ | —H |
| 87 | —OCH$_2$(CH$_2$)$_3$CH$_3$ | —OCH$_2$CH(CH$_3$)$_2$ | —H | 3 | 19.6 | " | —OCH$_2$(CH$_2$)$_3$CH$_3$ | —OCH$_2$CH(CH$_3$)$_2$ | —H |
| 88 | —OCH$_2$(CH$_2$)$_6$CH$_3$ | —OCH$_2$CH(CH$_3$)$_2$ | —H | 3 | 12.8 | " | —OCH$_2$(CH$_2$)$_6$CH$_3$ | —OCH$_2$CH(CH$_3$)$_2$ | —H |
| 89 | —OC(CH$_3$)$_3$ | —OCH$_2$(CH$_2$)$_3$CH$_3$ | —H | 3 | 19.3 | " | —OC(CH$_3$)$_3$ | —OCH$_2$(CH$_2$)$_3$CH$_3$ | —H |
| 90 | —OC(CH$_3$)$_3$ | —OCH$_2$(CH$_2$)$_6$CH$_3$ | —H | 3 | 15.5 | " | —OC(CH$_3$)$_3$ | —OCH$_2$(CH$_2$)$_6$CH$_3$ | —H |
| 91 | —OCH$_2$(CH$_2$)$_3$CH$_3$ | —OC(CH$_3$)$_3$ | —H | 3 | 18.2 | " | —OCH$_2$(CH$_2$)$_3$CH$_3$ | —OC(CH$_3$)$_3$ | —H |
| 92 | —OCH$_2$(CH$_2$)$_6$CH$_3$ | —OC(CH$_3$)$_3$ | —H | 3 | 11.1 | " | —OCH$_2$(CH$_2$)$_6$CH$_3$ | —OC(CH$_3$)$_3$ | —H |
| 93 | —OCH$_2$(CH$_2$)$_3$CH$_3$ | —OCH$_2$(CH$_2$)$_3$CH$_3$ | —H | 3 | 14.7 | " | —OCH$_2$(CH$_2$)$_3$CH$_3$ | —OCH$_2$(CH$_2$)$_3$CH$_3$ | —H |
| 94 | —OCH$_2$(CH$_2$)$_4$CH$_3$ | —OCH$_2$(CH$_2$)$_4$CH$_3$ | —H | 3 | 9.3 | Dark Brown | —OCH$_2$(CH$_2$)$_4$CH$_3$ | —OCH$_2$(CH$_2$)$_4$CH$_3$ | —H |
| 95 | —OCH$_2$(CH$_2$)$_5$CH$_3$ | —OCH$_2$(CH$_2$)$_5$CH$_3$ | —H | 3 | 7.6 | " | —OCH$_2$(CH$_2$)$_5$CH$_3$ | —OCH$_2$(CH$_2$)$_5$CH$_3$ | —H |
| 96 | —OCH$_2$(CH$_2$)$_6$CH$_3$ | —OCH$_2$(CH$_2$)$_6$CH$_3$ | —H | 3 | 6.3 | " | —OCH$_2$(CH$_2$)$_6$CH$_3$ | —OCH$_2$(CH$_2$)$_6$CH$_3$ | —H |
| 97 | —OCH$_3$ | —OCH$_3$ | —OCH$_3$ | 3 | 11.6 | " | —OCH$_3$ | —OCH$_3$ | —OCH$_3$ |
| 98 | —OCH$_3$ | —OCH$_3$ | —OCH$_3$ | 3 | 8.7 | " | —OCH$_3$ | —OCH$_3$ | —OCH$_3$ |
| 99 | —OCH$_3$ | —OCH$_3$ | —OCH$_3$ | 3 | 7.9 | " | —OCH$_3$ | —OCH$_3$ | —OCH$_3$ |
| 100 | —OCH$_3$ | —OCH$_3$ | —OCH$_3$ | 3 | 15.7 | Dark Brown | —OCH$_3$ | —OCH$_3$ | —OCH$_3$ |
| 101 | —OCH$_3$ | —OCH$_3$ | —OCH$_2$(CH$_2$)$_3$CH$_3$ | 3 | 19.2 | " | —OCH$_3$ | —OCH$_3$ | —OCH$_2$(CH$_2$)$_3$CH$_3$ |
| 102 | —OCH$_3$ | —OCH$_3$ | —OCH$_2$(CH$_2$)$_4$CH$_3$ | 3 | 16.3 | " | —OCH$_3$ | —OCH$_3$ | —OCH$_2$(CH$_2$)$_4$CH$_3$ |
| 103 | —OCH$_3$ | —OCH$_3$ | —OCH$_2$(CH$_2$)$_5$CH$_3$ | 3 | 13.3 | " | —OCH$_3$ | —OCH$_3$ | —OCH$_2$(CH$_2$)$_5$CH$_3$ |
| 104 | —OCH$_3$ | —OCH$_3$ | —OCH$_2$(CH$_2$)$_6$CH$_3$ | 3 | 7.5 | " | —OCH$_3$ | —OCH$_3$ | —OCH$_2$(CH$_2$)$_6$CH$_3$ |
| 105 | —OCH(CH$_3$)$_2$ | —OCH(CH$_3$)$_2$ | —OCH$_2$(CH$_2$)$_3$CH$_3$ | 3 | 12.6 | " | —OCH(CH$_3$)$_2$ | —OCH(CH$_3$)$_2$ | —OCH$_2$(CH$_2$)$_3$CH$_3$ |
| 106 | —OCH(CH$_3$)$_2$ | —OCH(CH$_3$)$_2$ | —OCH$_2$(CH$_2$)$_6$CH$_3$ | 3 | 8.7 | " | —OCH(CH$_3$)$_2$ | —OCH(CH$_3$)$_2$ | —OCH$_2$(CH$_2$)$_6$CH$_3$ |
| 107 | —OCH$_2$(CH$_2$)$_3$CH$_3$ | —OCH(CH$_3$)$_2$ | —OCH(CH$_3$)$_2$ | 3 | 10.8 | " | —OCH$_2$(CH$_2$)$_3$CH$_3$ | —OCH(CH$_3$)$_2$ | —OCH(CH$_3$)$_2$ |
| 108 | —OCH$_2$(CH$_2$)$_6$CH$_3$ | —OCH(CH$_3$)$_2$ | —OCH(CH$_3$)$_2$ | 3 | 7.1 | " | —OCH$_2$(CH$_2$)$_6$CH$_3$ | —OCH(CH$_3$)$_2$ | —OCH(CH$_3$)$_2$ |

TABLE 1-1-continued

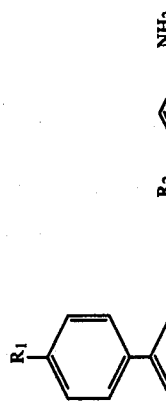

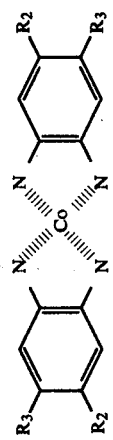

| Example No. | R₁ | R₂ | R₃ | Example No. of Reaction Conditions | Yield (%) | Crystal Color | R₁ | R₂ | R₃ |
|---|---|---|---|---|---|---|---|---|---|
| 109 | $-OCHCH_2CH_3$ $\|$ $CH_3$ | $-OCH_2(CH_2)_3CH_3$ | $-OCH_2(CH_2)_3CH_3$ | 3 | 10.8 | " | $-OCHCH_2CH_3$ $\|$ $CH_3$ | $-OCH_2(CH_2)_3CH_3$ | $-OCH_2(CH_2)_3CH_3$ |
| 110 | $-OCHCH_2CH_3$ $\|$ $CH_3$ | $-OCH_2(CH_2)_6CH_3$ | $-OCH_2(CH_2)_6CH_3$ | 3 | 9.4 | Dark Brown | $-OCHCH_2CH_3$ $\|$ $CH_3$ | $-OCH_2(CH_2)_6CH_3$ | $-OCH_2(CH_2)_6CH_3$ |
| 111 | $-OCH_2(CH_2)_3CH_3$ | $-OCHCH_2CH_3$ $\|$ $CH_3$ | $-OCHCH_2CH_3$ $\|$ $CH_3$ | 3 | 4.7 | " | $-OCH_2(CH_2)_3CH_3$ | $-OCHCH_2CH_3$ $\|$ $CH_3$ | $-OCHCH_2CH_3$ $\|$ $CH_3$ |
| 112 | $-OCH_2(CH_2)_6CH_3$ | $-OCHCH_2CH_3$ $\|$ $CH_3$ | $-OCHCH_2CH_3$ $\|$ $CH_3$ | 3 | 3.2 | " | $-OCH_2(CH_2)_6CH_3$ | $-OCHCH_2CH_3$ $\|$ $CH_3$ | $-OCHCH_2CH_3$ $\|$ $CH_3$ |
| 113 | $-OCH_2CH(CH_3)_2$ | $-OCH_2(CH_2)_3CH_3$ | $-OCH_2CH(CH_3)_2$ | 3 | 13.9 | " | $-OCH_2CH(CH_3)_2$ | $-OCH_2(CH_2)_3CH_3$ | $-OCH_2CH(CH_3)_2$ |
| 114 | $-OCH_2CH(CH_3)_2$ | $-OCH_2(CH_2)_6CH_3$ | $-OCH_2CH(CH_3)_2$ | 3 | 10.1 | " | $-OCH_2CH(CH_3)_2$ | $-OCH_2(CH_2)_6CH_3$ | $-OCH_2CH(CH_3)_2$ |
| 115 | $-OCH_2CH(CH_3)_2$ | $-OCH_2CH(CH_3)_2$ | $-OCH_2(CH_2)_3CH_3$ | 3 | 5.6 | " | $-OCH_2CH(CH_3)_2$ | $-OCH_2CH(CH_3)_2$ | $-OCH_2(CH_2)_3CH_3$ |
| 116 | $-OCH_2(CH_2)_6CH_3$ | $-OCH_2CH(CH_3)_2$ | $-OCH_2(CH_2)_6CH_3$ | 3 | 4.4 | " | $-OCH_2(CH_2)_6CH_3$ | $-OCH_2CH(CH_3)_2$ | $-OCH_2(CH_2)_6CH_3$ |
| 117 | $-OC(CH_3)_3$ | $-OCH_2(CH_2)_3CH_3$ | $-OCH_2(CH_2)_3CH_3$ | 3 | 12.4 | " | $-OC(CH_3)_3$ | $-OCH_2(CH_2)_3CH_3$ | $-OCH_2(CH_2)_3CH_3$ |
| 118 | $-OC(CH_3)_3$ | $-OCH_2(CH_2)_6CH_3$ | $-OCH_2(CH_2)_6CH_3$ | 3 | 10.6 | Dark Brown | $-OCH_2(CH_2)_3CH_3$ | $-OCH_2(CH_2)_6CH_3$ | $-OCH_2(CH_2)_6CH_3$ |
| 119 | $-OCH_2(CH_2)_3CH_3$ | $-OC(CH_3)_3$ | $-OC(CH_3)_3$ | 3 | 3.3 | " | $-OCH_2(CH_2)_3CH_3$ | $-OC(CH_3)_3$ | $-OC(CH_3)_3$ |
| 120 | $-OCH_2(CH_2)_6CH_3$ | $-OC(CH_3)_3$ | $-OC(CH_3)_3$ | 3 | 2.1 | " | $-OCH_2(CH_2)_6CH_3$ | $-OC(CH_3)_3$ | $-OC(CH_3)_3$ |
| 121 | $-OCH_2(CH_2)_3CH_3$ | $-OCH_2(CH_2)_3CH_3$ | $-OCH_2(CH_2)_3CH_3$ | 3 | 9.8 | " | $-OCH_2(CH_2)_3CH_3$ | $-OCH_2(CH_2)_3CH_3$ | $-OCH_2(CH_2)_3CH_3$ |
| 122 | $-OCH_2(CH_2)_4CH_3$ | $-OCH_2(CH_2)_4CH_3$ | $-OCH_2(CH_2)_4CH_3$ | 3 | 8.6 | " | $-OCH_2(CH_2)_4CH_3$ | $-OCH_2(CH_2)_6CH_3$ | $-OCH_2(CH_2)_4CH_3$ |

TABLE 1-1-continued

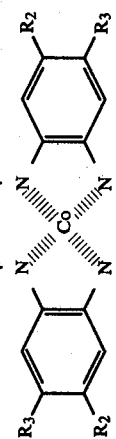
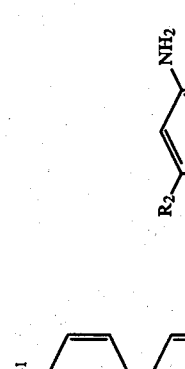

| Example No. | H$_3$C R$_1$ | R$_2$ | R$_3$ | Example No. of Reaction Conditions | Yield (%) | Crystal Color | R$_1$ | R$_2$ | R$_3$ |
|---|---|---|---|---|---|---|---|---|---|
| 123 | —OCH$_2$(CH$_2$)$_5$CH$_3$ | —OCH$_2$(CH$_2$)$_5$CH$_3$ | —OCH$_2$(CH$_2$)$_5$CH$_3$ | 3 | 4.7 | " | —OCH$_2$(CH$_2$)$_5$CH$_3$ | —OCH$_2$(CH$_2$)$_5$CH$_3$ | —OCH$_2$(CH$_2$)$_5$CH$_3$ |
| 124 | —OCH$_2$(CH$_2$)$_6$CH$_3$ | —OCH$_2$(CH$_2$)$_6$CH$_3$ | —OCH$_2$(CH$_2$)$_6$CH$_3$ | 3 | 5.2 | " | —OCH$_2$(CH$_2$)$_6$CH$_3$ | —OCH$_2$(CH$_2$)$_6$CH$_3$ | —OCH$_2$(CH$_2$)$_6$CH$_3$ |
| 125 | —H | —CH$_3$ | —CH$_3$ | 3 | 55.0 | Reddish Brown | —H | —CH$_3$ | —CH$_3$ |
| 126 | —OCH$_3$ | —CH$_3$ | —CH$_3$ | 3 | 37.3 | Reddish Brown | —OCH$_3$ | —CH$_3$ | —CH$_3$ |
| 127 | —OC$_2$H$_5$ | —CH$_3$ | —CH$_3$ | 3 | 35.7 | " | —OC$_2$H$_5$ | —CH$_3$ | —CH$_3$ |
| 128 | —OCH$_2$CH$_2$CH$_3$ | —CH$_3$ | —CH$_3$ | 3 | 32.2 | " | —OCH$_2$CH$_2$CH$_3$ | —CH$_3$ | —CH$_3$ |
| 129 | —OCH(CH$_3$)$_2$ | —CH$_3$ | —CH$_3$ | 3 | 29.3 | " | —OCH(CH$_3$)$_2$ | —CH$_3$ | —CH$_3$ |
| 130 | —OCH$_2$(CH$_2$)$_2$CH$_3$ | —CH$_3$ | —CH$_3$ | 3 | 40.5 | " | —OCH$_2$(CH$_2$)$_2$CH$_3$ | —CH$_3$ | —CH$_3$ |
| 131 | CH$_3$ —OCHCH$_2$CH$_3$ | —CH$_3$ | —CH$_3$ | 3 | 33.6 | " | CH$_3$ —OCHCH$_2$CH$_3$ | —CH$_3$ | —CH$_3$ |
| 132 | —OCH$_2$CH(CH$_3$)$_2$ | —CH$_3$ | —CH$_3$ | 3 | 31.6 | " | —OCH$_2$CH(CH$_3$)$_2$ | —CH$_3$ | —CH$_3$ |
| 133 | —OC(CH$_3$)$_3$ | —CH$_3$ | —CH$_3$ | 3 | 27.7 | " | —OC(CH$_3$)$_3$ | —CH$_3$ | —CH$_3$ |
| 134 | —OCH$_2$(CH$_2$)$_3$CH$_3$ | —CH$_3$ | —CH$_3$ | 3 | 38.5 | Brown | —OCH$_2$(CH$_2$)$_3$CH$_3$ | —CH$_3$ | —CH$_3$ |
| 135 | —OCH$_2$(CH$_2$)$_4$CH$_3$ | —CH$_3$ | —CH$_3$ | 3 | 35.4 | " | —OCH$_2$(CH$_2$)$_4$CH$_3$ | —CH$_3$ | —CH$_3$ |
| 136 | —OCH$_2$(CH$_2$)$_5$CH$_3$ | —CH$_3$ | —CH$_3$ | 3 | 31.7 | " | —OCH$_2$(CH$_2$)$_5$CH$_3$ | —CH$_3$ | —CH$_3$ |
| 137 | —OCH$_2$(CH$_2$)$_6$CH$_3$ | —CH$_3$ | —CH$_3$ | 3 | 28.1 | " | —OCH$_2$(CH$_2$)$_6$CH$_3$ | —CH$_3$ | —CH$_3$ |
| 138 | —OCH$_3$ | —C$_2$H$_5$ | —C$_2$H$_5$ | 3 | 39.9 | Reddish Brown | —OCH$_3$ | —C$_2$H$_5$ | —C$_2$H$_5$ |
| 139 | —OCH$_3$ | —CH$_2$CH$_2$CH$_3$ | —CH$_2$CH$_2$CH$_3$ | 3 | 17.6 | " | —OCH$_3$ | —CH$_2$CH$_2$CH$_3$ | —CH$_2$CH$_2$CH$_3$ |
| 140 | —OCH$_3$ | —CH$_2$(CH$_2$)$_2$CH$_3$ | —CH$_2$(CH$_2$)$_2$CH$_3$ | 3 | 30.1 | Brown | —OCH$_3$ | —CH$_2$(CH$_2$)$_2$CH$_3$ | —CH$_2$(CH$_2$)$_2$CH$_3$ |
| 141 | —OCH$_3$ | —CH$_2$(CH$_2$)$_3$CH$_3$ | —CH$_2$(CH$_2$)$_3$CH$_3$ | 3 | 26.3 | " | —OCH$_3$ | —CH$_2$(CH$_2$)$_3$CH$_3$ | —CH$_2$(CH$_2$)$_3$CH$_3$ |
| 142 | —OCH$_3$ | —CH$_2$(CH$_2$)$_4$CH$_3$ | —CH$_2$(CH$_2$)$_4$CH$_3$ | 3 | 23.7 | Brown | —OCH$_3$ | —CH$_2$(CH$_2$)$_4$CH$_3$ | —CH$_2$(CH$_2$)$_4$CH$_3$ |
| 143 | —OCH$_3$ | —CH$_2$(CH$_2$)$_5$CH$_3$ | —CH$_2$(CH$_2$)$_5$CH$_3$ | 3 | 18.8 | Dark Brown | —OCH$_3$ | —CH$_2$(CH$_2$)$_5$CH$_3$ | —CH$_2$(CH$_2$)$_5$CH$_3$ |
| 144 | —OCH$_3$ | —CH$_2$(CH$_2$)$_6$CH$_3$ | —CH$_2$(CH$_2$)$_6$CH$_3$ | 3 | 15.6 | " | —OCH$_3$ | —CH$_2$(CH$_2$)$_6$CH$_3$ | —CH$_2$(CH$_2$)$_6$CH$_3$ |
| 145 | —OC$_2$H$_5$ | —C$_2$H$_5$ | —C$_2$H$_5$ | 3 | 30.0 | Brown | —OC$_2$H$_5$ | —C$_2$H$_5$ | —C$_2$H$_5$ |
| 146 | —OCH$_2$CH$_2$CH$_3$ | —CH$_2$CH$_2$CH$_3$ | —CH$_2$CH$_2$CH$_3$ | 3 | 17.9 | " | —OCH$_2$CH$_2$CH$_3$ | —CH$_2$CH$_2$CH$_3$ | —CH$_2$CH$_2$CH$_3$ |

TABLE 1-1-continued

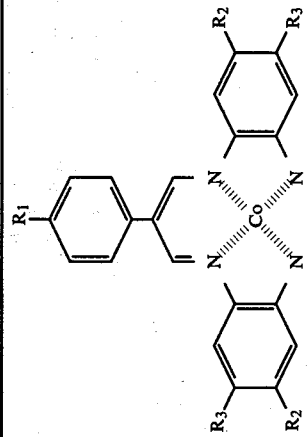
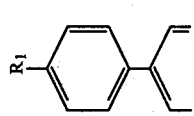

| Example No. | R₁ | R₂ | R₃ | R₂ | R₃ | Example No. of Reaction Conditions | Yield (%) | Crystal Color | R₁ | R₂ | R₃ |
|---|---|---|---|---|---|---|---|---|---|---|---|
| 147 | —OCH₂(CH₂)₂CH₃ | —OCH₃ | —CH₂(CH₂)₂CH₃ | —CH₂(CH₂)₂CH₃ | —OCH₃ | 3 | 24.9 | Dark Brown | —OCH₂(CH₂)₂CH₃ | —CH₂(CH₂)₂CH₃ | —CH₂(CH₂)₂CH₃ |
| 148 | —OCH₂(CH₂)₃CH₃ | —OCH₃ | —CH₂(CH₂)₃CH₃ | —CH₂(CH₂)₃CH₃ | —OCH₃ | 3 | 23.1 | " | —OCH₂(CH₂)₃CH₃ | —CH₂(CH₂)₃CH₃ | —CH₂(CH₂)₃CH₃ |
| 149 | —OCH₂(CH₂)₄CH₃ | —OCH₃ | —CH₂(CH₂)₄CH₃ | —CH₂(CH₂)₄CH₃ | —OCH₃ | 3 | 18.4 | " | —OCH₂(CH₂)₄CH₃ | —CH₂(CH₂)₄CH₃ | —CH₂(CH₂)₄CH₃ |
| 150 | —OCH₂(CH₂)₅CH₃ | —OCH₃ | —CH₂(CH₂)₅CH₃ | —CH₂(CH₂)₅CH₃ | —OCH₃ | 3 | 19.5 | Dark Brown | —OCH₂(CH₂)₅CH₃ | —CH₂(CH₂)₅CH₃ | —CH₂(CH₂)₅CH₃ |
| 151 | —OCH₂(CH₂)₆CH₃ | —OCH₃ | —CH₂(CH₂)₆CH₃ | —CH₂(CH₂)₆CH₃ | —OCH₃ | 3 | 11.8 | " | —OCH₂(CH₂)₆CH₃ | —CH₂(CH₂)₆CH₃ | —CH₂(CH₂)₆CH₃ |
| 152 | —H | —CH₃ | —H | —H | —CH₃ | 3 | 27.2 | Reddish Brown | —H | —H | —CH₃ |
| 153 | —CH₃ | —OCH₃ | —OCH₃ | —OCH₃ | —OCH₃ | 3 | 23.7 | Dark Brown | —CH₃ | —OCH₃ | —OCH₃ |
| 154 | —C₂H₅ | —OCH₃ | —OCH₃ | —OCH₃ | —OCH₃ | 3 | 25.8 | " | —C₂H₅ | —OCH₃ | —OCH₃ |
| 155 | —CH₂CH₂CH₃ | —OCH₃ | —OCH₃ | —OCH₃ | —OCH₃ | 3 | 20.6 | " | —CH₂CH₂CH₃ | —OCH₃ | —OCH₃ |
| 156 | —CH(CH₃)₂ | —OCH₃ | —OCH₃ | —OCH₃ | —OCH₃ | 3 | 17.5 | " | —CH(CH₃)₂ | —OCH₃ | —OCH₃ |
| 157 | —CH₂(CH₂)₂CH₃ | —OCH₃ | —OCH₃ | —OCH₃ | —OCH₃ | 3 | 22.7 | " | —CH₂(CH₂)₂CH₃ | —OCH₃ | —OCH₃ |
| 158 | —CHCH₂CH₃ CH₃ | —OCH₃ | —OCH₃ | —OCH₃ | —OCH₃ | 3 | 17.6 | Dark Brown | —CHCH₂CH₃ CH₃ | —OCH₃ | —OCH₃ |
| 159 | —CH₂CH(CH₃)₂ | —OCH₃ | —OCH₃ | —OCH₃ | —OCH₃ | 3 | 11.1 | " | —CH₂CH(CH₃)₂ | —OCH₃ | —OCH₃ |
| 160 | —C(CH₃)₃ | —OCH₃ | —OCH₃ | —OCH₃ | —OCH₃ | 3 | 8.9 | " | —C(CH₃)₃ | —OCH₃ | —OCH₃ |
| 161 | —CH₂(CH₂)₃CH₃ | —OCH₃ | —OCH₃ | —OCH₃ | —OCH₃ | 3 | 19.3 | " | —CH₂(CH₂)₃CH₃ | —OCH₃ | —OCH₃ |
| 162 | —CH₂(CH₂)₄CH₃ | —OCH₃ | —OCH₃ | —OCH₃ | —OCH₃ | 3 | 16.5 | " | —CH₂(CH₂)₄CH₃ | —OCH₃ | —OCH₃ |
| 163 | —CH₂(CH₂)₅CH₃ | —OCH₃ | —OCH₃ | —OCH₃ | —OCH₃ | 3 | 14.9 | " | —CH₂(CH₂)₅CH₃ | —OCH₃ | —OCH₃ |
| 164 | —CH₂(CH₂)₆CH₃ | —OCH₃ | —OCH₃ | —OCH₃ | —OCH₃ | 3 | 13.0 | " | —CH₂(CH₂)₆CH₃ | —OCH₃ | —OCH₃ |
| 165 | —CH₃ | —OC₂H₅ | —OC₂H₅ | —OC₂H₅ | —OC₂H₅ | 3 | 24.2 | " | —CH₃ | —OC₂H₅ | —OC₂H₅ |
| 166 | —CH₃ | —OCH₂CH₂CH₃ | —OCH₂CH₂CH₃ | —OCH₂CH₂CH₃ | —OCH₂CH₂CH₃ | 3 | 17.5 | Dark Brown | —CH₃ | —OCH₂CH₂CH₃ | —OCH₂CH₂CH₃ |
| 167 | —CH₃ | —OCH(CH₃)₂ | —OCH(CH₃)₂ | —OCH(CH₃)₂ | —OCH(CH₃)₂ | 3 | 14.4 | " | —CH₃ | —OCH(CH₃)₂ | —OCH(CH₃)₂ |
| 168 | —CH₃ | —OCH₂(CH₂)₂CH₃ | —OCH₂(CH₂)₂CH₃ | —OCH₂(CH₂)₂CH₃ | —OCH₂(CH₂)₂CH₃ | 3 | 20.8 | " | —CH₃ | —OCH₂(CH₂)₂CH₃ | —OCH₂(CH₂)₂CH₃ |

TABLE 1-1-continued

| Example No. | R₁ | R₂ | R₃ | Example No. of Reaction Conditions | Yield (%) | Crystal Color | R₁ | R₂ | R₃ |
|---|---|---|---|---|---|---|---|---|---|
| 169 | —CH₃ | —CH₃ —OCHCH₂CH₃ | —OCHCH₂CH₃ CH₃ | 3 | 15.3 |  | —CH₃ | CH₃ | —OCHCH₂CH₃ CH₃ |
| 170 | —CH₃ | —OC(CH₃)₃ | —OC(CH₃)₃ | 3 | 16.7 | " | —CH₃ | —OCH₂CH(CH₃)₂ | —OCH₂CH(CH₃)₂ |
| 171 | —CH₃ | —OCH₂(CH₂)₃CH₃ | —OCH₂(CH₂)₃CH₃ | 3 | 12.3 | " | —CH₃ | —OC(CH₃)₃ | —OC(CH₃)₃ |
| 172 | —CH₃ | —OCH₂(CH₂)₄CH₃ | —OCH₂(CH₂)₄CH₃ | 3 | 19.6 | " | —CH₃ | —OCH₂(CH₂)₃CH₃ | —OCH₂(CH₂)₃CH₃ |
| 173 | —CH₃ | —OCH₂(CH₂)₅CH₃ | —OCH₂(CH₂)₅CH₃ | 3 | 17.8 | " | —CH₃ | —OCH₂(CH₂)₄CH₃ | —OCH₂(CH₂)₄CH₃ |
| 174 | —CH₃ | —OCH₂(CH₂)₆CH₃ | —OCH₂(CH₂)₆CH₃ | 3 | 16.0 | Dark Brown | —CH₃ | —OCH₂(CH₂)₅CH₃ | —OCH₂(CH₂)₅CH₃ |
| 175 | —CH₃ | —OC₂H₅ | —OC₂H₅ | 3 | 13.1 | " | —CH₃ | —OCH₂(CH₂)₆CH₃ | —OCH₂(CH₂)₆CH₃ |
| 176 | —C₂H₅ | —OCH₂CH₃ | —OCH₂CH₃ | 3 | 24.6 | " | —C₂H₅ | —OC₂H₅ | —OC₂H₅ |
| 177 | —CH₂CH₂CH₃ | —OCH₂(CH₂)₂CH₃ | —OCH₂(CH₂)₂CH₃ | 3 | 21.7 | " | —CH₂CH₂CH₃ | —OCH₂CH₂CH₃ | —OCH₂CH₂CH₃ |
| 178 | —CH₂(CH₂)₂CH₃ | —OCH₂(CH₂)₃CH₃ | —OCH₂(CH₂)₃CH₃ | 3 | 18.7 | " | —CH₂(CH₂)₂CH₃ | —OCH₂(CH₂)₂CH₃ | —OCH₂(CH₂)₂CH₃ |
| 179 | —CH₂(CH₂)₃CH₃ | —OCH₂(CH₂)₄CH₃ | —OCH₂(CH₂)₄CH₃ | 3 | 16.2 | " | —CH₂(CH₂)₃CH₃ | —OCH₂(CH₂)₃CH₃ | —OCH₂(CH₂)₃CH₃ |
| 180 | —CH₂(CH₂)₄CH₃ | —OCH₂(CH₂)₅CH₃ | —OCH₂(CH₂)₅CH₃ | 3 | 16.6 | " | —CH₂(CH₂)₄CH₃ | —OCH₂(CH₂)₄CH₃ | —OCH₂(CH₂)₄CH₃ |
| 181 | —CH₂(CH₂)₅CH₃ | —OCH₂(CH₂)₆CH₃ | —OCH₂(CH₂)₆CH₃ | 3 | 15.5 | " | —CH₂(CH₂)₅CH₃ | —OCH₂(CH₂)₅CH₃ | —OCH₂(CH₂)₅CH₃ |
| 182 | —CH₂(CH₂)₆CH₃ | —H | —H | 3 | 11.7 | Dark Brown | —CH₂(CH₂)₆CH₃ | —OCH₂(CH₂)₆CH₃ | —OCH₂(CH₂)₆CH₃ |
| 183 | —C₂H₅ | —H | —H | 3 | 48.3 | " | —C₂H₅ | —H | —H |
| 184 | —CH₂(CH₂)₆CH₃ | —CH₃ | —CH₃ | 3 | 37.3 | Black | —CH₂(CH₂)₆CH₃ | —H | —H |
| 185 | —C₂H₅ | —CH₃ | —CH₃ | 5 | 65.3 | Brown | —C₂H₅ | —CH₃ | —CH₃ |
| 186 | —CH₂CH₂CH₃ | —CH₃ | —CH₃ | 5 | 59.2 | " | —CH₂CH₂CH₃ | —CH₃ | —CH₃ |
| 187 | —CH(CH₃)₂ | —CH₃ | —CH₃ | 5 | 43.2 | " | —CH(CH₃)₂ | —CH₃ | —CH₃ |
| 188 | —CH₂(CH₂)₂CH₃ | —CH₃ | —CH₃ | 5 | 54.4 | " | —CH₂(CH₂)₂CH₃ | —CH₃ | —CH₃ |
| 189 | —CHCH₂CH₃ | —CH₃ | —CH₃ | 5 | 37.0 | " | —CH₃ —CHCH₂CH₃ | —CH₃ | —CH₃ |
| 190 | —CH₂CH(CH₃)₂ | —CH₃ | —CH₃ | 5 | 40.3 | Brown | —CH₂CH(CH₃)₂ | —CH₃ | —CH₃ |

TABLE 1-1-continued

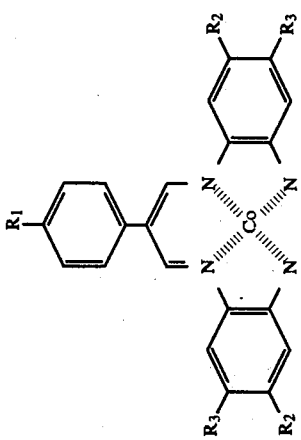

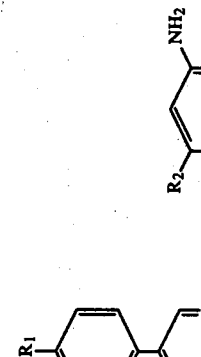

| Example No. | R₁ | R₂ | R₃ | R₃ | R₂ | Example No. of Reaction Conditions | Yield (%) | Crystal Color | R₁ | R₂ | R₃ |
|---|---|---|---|---|---|---|---|---|---|---|---|
| 191 | —C(CH₃)₃ | —CH₃ | —CH₃ | —CH₃ | —CH₃ | 5 | 28.7 | " | —C(CH₃)₃ | —CH₃ | —CH₃ |
| 192 | —CH₂(CH₂)₃CH₃ | —CH₃ | —CH₃ | —CH₃ | —CH₃ | 5 | 51.2 | " | —CH₂(CH₂)₃CH₃ | —CH₃ | —CH₃ |
| 193 | —CH₂(CH₂)₄CH₃ | —CH₃ | —CH₃ | —CH₃ | —CH₃ | 5 | 48.7 | " | —CH₂(CH₂)₄CH₃ | —CH₃ | —CH₃ |
| 194 | —CH₂(CH₂)₅CH₃ | —CH₃ | —CH₃ | —CH₃ | —CH₃ | 5 | 36.5 | " | —CH₂(CH₂)₅CH₃ | —CH₃ | —CH₃ |
| 195 | —CH₂(CH₂)₆CH₃ | —CH₃ | —CH₃ | —CH₃ | —CH₃ | 5 | 21.9 | " | —CH₂(CH₂)₆CH₃ | —CH₃ | —CH₃ |
| 196 | —CH₃ | —C₂H₅ | —C₂H₅ | —C₂H₅ | —C₂H₅ | 5 | 63.5 | " | —CH₃ | —C₂H₅ | —C₂H₅ |
| 197 | —CH₃ | —CH₂CH₂CH₃ | —CH₂CH₂CH₃ | —CH₂CH₂CH₃ | —CH₂CH₂CH₃ | 5 | 52.4 | " | —CH₃ | —CH₂CH₂CH₃ | —CH₂CH₂CH₃ |
| 198 | —CH₃ | —CH₂(CH₂)₂CH₃ | —CH₂(CH₂)₂CH₃ | —CH₂(CH₂)₂CH₃ | —CH₂(CH₂)₂CH₃ | 5 | 47.3 | Brown | —CH₃ | —CH₂(CH₂)₂CH₃ | —CH₂(CH₂)₂CH₃ |
| 199 | —CH₃ | —CH₂(CH₂)₃CH₃ | —CH₂(CH₂)₃CH₃ | —CH₂(CH₂)₃CH₃ | —CH₂(CH₂)₃CH₃ | 5 | 39.2 | " | —CH₃ | —CH₂(CH₂)₃CH₃ | —CH₂(CH₂)₃CH₃ |
| 200 | —CH₃ | —CH₂(CH₂)₄CH₃ | —CH₂(CH₂)₄CH₃ | —CH₂(CH₂)₄CH₃ | —CH₂(CH₂)₄CH₃ | 5 | 28.9 | " | —CH₃ | —CH₂(CH₂)₄CH₃ | —CH₂(CH₂)₄CH₃ |
| 201 | —CH₃ | —CH₂(CH₂)₅CH₃ | —CH₂(CH₂)₅CH₃ | —CH₂(CH₂)₅CH₃ | —CH₂(CH₂)₅CH₃ | 5 | 19.8 | " | —CH₃ | —CH₂(CH₂)₅CH₃ | —CH₂(CH₂)₅CH₃ |
| 202 | —CH₃ | —CH₂(CH₂)₆CH₃ | —CH₂(CH₂)₆CH₃ | —CH₂(CH₂)₆CH₃ | —CH₂(CH₂)₆CH₃ | 5 | 18.2 | " | —CH₃ | —CH₂(CH₂)₆CH₃ | —CH₂(CH₂)₆CH₃ |
| 203 | —C₂H₅ | —C₂H₅ | —C₂H₅ | —C₂H₅ | —C₂H₅ | 5 | 60.2 | " | —C₂H₅ | —C₂H₅ | —C₂H₅ |
| 204 | —CH₂CH₂CH₃ | —CH₂CH₂CH₃ | —CH₂CH₂CH₃ | —CH₂CH₂CH₃ | —CH₂CH₂CH₃ | 5 | 55.6 | " | —CH₂CH₂CH₃ | —CH₂CH₂CH₃ | —CH₂CH₂CH₃ |
| 205 | —CH₂(CH₂)₂CH₃ | —CH₂(CH₂)₂CH₃ | —CH₂(CH₂)₂CH₃ | —CH₂(CH₂)₂CH₃ | —CH₂(CH₂)₂CH₃ | 5 | 43.3 | " | —CH₂(CH₂)₂CH₃ | —CH₂(CH₂)₂CH₃ | —CH₂(CH₂)₂CH₃ |
| 206 | —CH₂(CH₂)₃CH₃ | —CH₂(CH₂)₃CH₃ | —CH₂(CH₂)₃CH₃ | —CH₂(CH₂)₃CH₃ | —CH₂(CH₂)₃CH₃ | 5 | 38.0 | Brown | —CH₂(CH₂)₃CH₃ | —CH₂(CH₂)₃CH₃ | —CH₂(CH₂)₃CH₃ |
| 207 | —CH₂(CH₂)₄CH₃ | —CH₂(CH₂)₄CH₃ | —CH₂(CH₂)₄CH₃ | —CH₂(CH₂)₄CH₃ | —CH₂(CH₂)₄CH₃ | 5 | 26.8 | " | —CH₂(CH₂)₄CH₃ | —CH₂(CH₂)₄CH₃ | —CH₂(CH₂)₄CH₃ |
| 208 | —CH₂(CH₂)₅CH₃ | —CH₂(CH₂)₅CH₃ | —CH₂(CH₂)₅CH₃ | —CH₂(CH₂)₅CH₃ | —CH₂(CH₂)₅CH₃ | 5 | 13.2 | " | —CH₂(CH₂)₅CH₃ | —CH₂(CH₂)₅CH₃ | —CH₂(CH₂)₅CH₃ |
| 209 | —CH₂(CH₂)₆CH₃ | —CH₂(CH₂)₆CH₃ | —CH₂(CH₂)₆CH₃ | —CH₂(CH₂)₆CH₃ | —CH₂(CH₂)₆CH₃ | 5 | 11.3 | " | —CH₂(CH₂)₆CH₃ | —CH₂(CH₂)₆CH₃ | —CH₂(CH₂)₆CH₃ |

TABLE 1-2

| Example No. | Mass Spectrum Calcd. | Found | Formula | Elementary Analysis C:H:N (%) Calcd. | Found | Visible Spectrum [DMF] (nm) |
|---|---|---|---|---|---|---|
| 6 | 585.6 | 585 | $C_{34}H_{30}N_4O_2 \cdot Co$ | 69.74:5.16:9.57 | 69.61:5.22:9.56 | 380(s)*[1], 397, 429(s), 522 |
| 7 | 613.6 | 613 | $C_{36}H_{34}N_4O_2 \cdot Co$ | 70.47:5.59:9.13 | 69.99:5.65:8.98 | 380(s), 397, 429(s), 522 |
| 8 | 557.5 | 557 | $C_{32}H_{26}N_4O_2 \cdot Co$ | 68.94:4.70:10.05 | 69.04:4.70:10.01 | 388, 419, 438, 522 |
| 9 | 585.6 | 585 | $C_{34}H_{30}N_4O_2 \cdot Co$ | 69.74:5.16:9.57 | 69.66:5.23:9.47 | 388, 419, 438, 522 |
| 10 | 613.6 | 613 | $C_{36}H_{34}N_4O_2 \cdot Co$ | 70.47:5.59:9.13 | 70.58:5.63:9.01 | 380(s), 397, 429(s), 522 |
| 11 | 641.7 | 641 | $C_{38}H_{38}N_4O_2 \cdot Co$ | 71.13:5.97:8.73 | 71.02:5.88:8.65 | 380(s), 397, 429(s), 522 |
| 12 | 641.7 | 641 | $C_{38}H_{38}N_4O_2 \cdot Co$ | 71.13:5.97:8.73 | 71.21:6.05:8.59 | 380(s), 397, 429(s), 522 |
| 13 | 617.6 | 617 | $C_{34}H_{30}N_4O_4 \cdot Co$ | 66.12:4.90:9.07 | 65.97:5.02:9.01 | 382, 426, 453, ~520*[2] |
| 14 | 613.6 | 613 | $C_{36}H_{34}N_4O_2 \cdot Co$ | 70.47:5.57:9.13 | 70.56:5.70:9.10 | 388 419, 438, 522 |
| 15 | 641.7 | 641 | $C_{38}H_{38}N_4O_2 \cdot Co$ | 71.13:5.97:8.73 | 71.11:6.04:8.82 | 388, 419, 437, 522 |
| 16 | 673.7 | 673 | $C_{38}H_{38}N_4O_4 \cdot Co$ | 67.75:5.69:8.32 | 67.97:5.52:8.30 | 382, 427, 454, ~520 |
| 17 | 729.7 | 729 | $C_{42}H_{46}N_4O_4 \cdot Co$ | 69.12:6.35:7.68 | 69.28:6.40:7.52 | 383, 429, 454, ~520 |
| 18 | 785.9 | 785 | $C_{46}H_{54}N_4O_4 \cdot Co$ | 70.30:6.93:7.13 | 70.51:7.02:7.00 | 383, 428, 454, ~520 |
| 19 | 617.6 | 617 | $C_{34}H_{30}N_4O_4 \cdot Co$ | 66.12:4.90:9.07 | 66.22:4.79:9.13 | 388(s), 399, 420(s), 444(s), 522 |
| 20 | 645.6 | 645 | $C_{36}H_{34}N_4O_4 \cdot Co$ | 66.78:5.31:8.68 | 67.07:5.41:8.62 | 388(s), 399, 420(s), 444(s), 522 |
| 21 | 673.7 | 673 | $C_{38}H_{38}N_4O_4 \cdot Co$ | 67.75:5.67:8.32 | 68.01:5.55:8.43 | 388(s), 399, 420(s), 443(s), 522 |
| 22 | 673.7 | 673 | $C_{38}H_{38}N_4O_4 \cdot Co$ | 67.75:5.67:8.32 | 68.01:5.55:8.43 | 388(s), 399, 420(s), 443(s), 521 |
| 23 | 701.7 | 701 | $C_{40}H_{42}N_4O_4 \cdot Co$ | 68.47:6.03:7.98 | 68.34:5.97:7.87 | 388(s), 399, 420(s), 443(s), 521 |
| 24 | 701.7 | 701 | $C_{40}H_{42}N_4O_4 \cdot Co$ | 68.47:6.03:7.98 | 68.62:5.95:7.90 | 388(s), 399, 420(s), 443(s), 521 |
| 25 | 701.7 | 701 | $C_{40}H_{42}N_4O_4 \cdot Co$ | 68.47:6.03:7.98 | 68.58:5.93:8.10 | 388(s), 399, 420(s), 443(s), 521 |
| 26 | 701.7 | 701 | $C_{40}H_{42}N_4O_4 \cdot Co$ | 68.47:6.03:7.98 | 68.35:6.11:8.03 | 388(s), 399, 420(s), 443(s), 521 |
| 27 | 733.7 | 733 | $C_{40}H_{42}N_4O_6 \cdot Co$ | 65.48:5.77:7.64 | 65.59:5.65:7.70 | 384, 395(s), 430, 457, ~525 |
| 28 | 789.8 | 789 | $C_{44}H_{50}N_4O_6 \cdot Co$ | 66.91:6.38:7.09 | 66.83:6.36:7.12 | 384, 395(s), 430, 457, ~524 |
| 29 | 789.8 | 789 | $C_{44}H_{50}N_4O_6 \cdot Co$ | 66.91:6.38:7.09 | 67.12:6.35:6.87 | 384, 395(s), 430, 457, ~524 |
| 30 | 845.9 | 845 | $C_{48}H_{58}N_4O_6 \cdot Co$ | 68.16:6.91:6.62 | 68.06:7.11:6.69 | 384, 395(s), 429, 458, ~525 |
| 31 | 845.9 | 845 | $C_{48}H_{58}N_4O_6 \cdot Co$ | 68.16:6.91:6.62 | 68.11:6.82:6.79 | 384, 395(s), 430, 457, ~525 |
| 32 | 845.9 | 845 | $C_{48}H_{58}N_4O_6 \cdot Co$ | 68.16:6.91:6.62 | 68.07:6.98:6.83 | 384, 395(s), 430, 458, ~525 |
| 33 | 645.6 | 645 | $C_{36}H_{34}N_4O_4 \cdot Co$ | 66.98:5.31:8.68 | 66.90:5.41:8.61 | 388(s), 399, 420(s), 444(s), 523 |
| 34 | 673.7 | 673 | $C_{38}H_{38}N_4O_4 \cdot Co$ | 67.75:5.69:8.32 | 67.51:5.67:8.19 | 388(s), 399, 420(s), 443(s), 522 |
| 35 | 701.7 | 701 | $C_{40}H_{42}N_4O_4 \cdot Co$ | 68.47:6.03:7.78 | 68.33:6.21:8.08 | 388(s), 399, 420(s), 443(s), 522 |
| 36 | 701.7 | 701 | $C_{40}H_{42}N_4O_4 \cdot Co$ | 68.47:6.03:7.78 | 68.63:5.92:7.84 | 388(s), 399, 420(s), 443(s), 522 |
| 37 | 729.8 | 729 | $C_{42}H_{46}N_4O_4 \cdot Co$ | 69.12:6.35:7.68 | 69.30:6.48:7.57 | 388(s), 399, 420(s), 443(s), 522 |
| 38 | 705.7 | 705 | $C_{38}H_{38}N_4O_6 \cdot Co$ | 64.68:5.43:7.94 | 64.61:5.53:7.86 | 384, 395(s), 430, 457, ~525 |
| 39 | 761.8 | 761 | $C_{42}H_{46}N_4O_6 \cdot Co$ | 66.22:6.09:7.35 | 66.19:6.20:7.44 | 384, 395(s), 431, 456, ~525 |
| 40 | 817.9 | 817 | $C_{46}H_{54}N_4O_6 \cdot Co$ | 67.55:6.66:6.85 | 67.63:6.85:6.91 | 384, 395(s), 430, 458, ~524 |
| 41 | 874.0 | 873 | $C_{50}H_{62}N_4O_6 \cdot Co$ | 68.71:7.15:6.41 | 68.55:7.08:6.32 | 384, 395(s), 429, 458, ~525 |
| 42 | 701.7 | 701 | $C_{40}H_{42}N_4O_4 \cdot Co$ | 68.47:6.03:7.98 | 68.53:6.00:7.91 | 388(s), 399, 420(s), 443(s), 522 |
| 43 | 729.8 | 729 | $C_{42}H_{46}N_4O_4 \cdot Co$ | 69.12:6.35:7.68 | 69.06:6.20:7.70 | 388(s), 399, 420(s), 442(s), 521 |
| 44 | 757.8 | 757 | $C_{44}H_{50}N_4O_4 \cdot Co$ | 69.74:6.65:7.39 | 69.87:6.54:7.45 | 388(s), 399, 420(s), 442(s), 521 |

TABLE 1-2-continued

| Example No. | Mass Spectrum Calcd. | Found | Formula | Elementary Analysis C:H:N (%) Calcd. | Found | Visible Spectrum [DMF] (nm) |
|---|---|---|---|---|---|---|
| 45 | 733.7 | 733 | $C_{40}H_{42}N_4O_6 \cdot Co$ | 65.48:5.77:7.64 | 65.32:5.91:7.60 | 384, 395(s), 430, 457, ~525 |
| 46 | 789.8 | 789 | $C_{44}H_{50}N_4O_6 \cdot Co$ | 66.91:6.38:7.09 | 67.09:6.20:7.13 | 384, 395(s), 431, 456, ~526 |
| 47 | 845.7 | 845 | $C_{48}H_{58}N_4O_6 \cdot Co$ | 68.16:6.91:6.62 | 67.97:7.01:6.77 | 384, 396(s), 431, 458, ~524 |
| 48 | 902.1 | 901 | $C_{52}H_{66}N_4O_6 \cdot Co$ | 69.24:7.37:6.21 | 69.11:7.53:6.15 | 384, 396(s), 429, 459, ~525 |
| 49 | 673.7 | 673 | $C_{38}H_{38}N_4O_4 \cdot Co$ | 67.75:5.67:8.32 | 67.88:5.55:8.40 | 388(s), 399, 420(s), 443(s), 522 |
| 50 | 729.8 | 729 | $C_{42}H_{46}N_4O_4 \cdot Co$ | 69.12:6.35:7.68 | 68.98:6.39:7.75 | 388(s), 399, 420(s), 443(s), 521 |
| 51 | 733.7 | 733 | $C_{40}H_{42}N_4O_6 \cdot Co$ | 65.48:5.77:7.64 | 65.61:5.67:7.55 | 384, 395(s), 430, 457, ~524 |
| 52 | 701.7 | 701 | $C_{40}H_{42}N_4O_4 \cdot Co$ | 68.47:6.03:7.98 | 68.58:6.15:7.83 | 388(s), 399, 420(s), 442(s), 521 |
| 53 | 729.8 | 729 | $C_{42}H_{46}N_4O_4 \cdot Co$ | 69.12:6.35:7.68 | 69.31:6.38:7.78 | 388(s), 399, 420(s), 442(s), 521 |
| 54 | 757.8 | 757 | $C_{44}H_{50}N_4O_4 \cdot Co$ | 69.74:6.65:7.39 | 69.97:6.60:7.33 | 388(s), 399, 420(s), 442(s), 521 |
| 55 | 785.9 | 785 | $C_{46}H_{54}N_4O_4 \cdot Co$ | 70.30:6.93:7.13 | 70.20:6.76:7.33 | 388(s), 399, 420(s), 442(s), 521 |
| 56 | 761.8 | 761 | $C_{42}H_{46}N_4O_6 \cdot Co$ | 66.22:6.09:7.35 | 66.19:6.01:7.55 | 383, 394(s), 430, 457, ~525 |
| 57 | 817.9 | 817 | $C_{46}H_{54}N_4O_6 \cdot Co$ | 67.55:6.66:6.85 | 67.85:6.55:6.73 | 384, 395(s), 930, 457, ~525 |
| 58 | 874.0 | 873 | $C_{50}H_{62}N_4O_6 \cdot Co$ | 68.71:7.15:6.41 | 68.82:7.01:6.33 | 384, 396(s), 431, 458, ~523 |
| 59 | 930.1 | 929 | $C_{54}H_{70}N_4O_6 \cdot Co$ | 69.73:7.59:6.02 | 69.78:7.53:6.21 | 385, 396(s), 429, 459, ~524 |
| 60 | 701.7 | 701 | $C_{40}H_{42}N_4O_4 \cdot Co$ | 68.47:6.03:7.98 | 68.29:6.15:8.06 | 388(s), 399, 420(s), 444(s), 522 |
| 61 | 785.9 | 785 | $C_{46}H_{54}N_4O_4 \cdot Co$ | 70.30:6.93:7.13 | 70.48:7.05:6.95 | 388(s), 399, 420(s), 443(s), 522 |
| 62 | 761.8 | 761 | $C_{42}H_{46}N_4O_6 \cdot Co$ | 66.22:6.09:7.35 | 66.34:5.98:7.29 | 384, 395(s), 430, 457, ~525 |
| 63 | 701.7 | 701 | $C_{40}H_{42}N_4O_4 \cdot Co$ | 68.47:6.03:7.98 | 68.33:6.05:8.12 | 388(s), 399, 420(s), 443(s), 522 |
| 64 | 785.9 | 785 | $C_{46}H_{54}N_4O_4 \cdot Co$ | 70.30:6.93:7.13 | 70.25:7.07:7.01 | 388(s), 399, 420(s), 443(s), 522 |
| 65 | 761.8 | 761 | $C_{42}H_{46}N_4O_6 \cdot Co$ | 66.22:6.09:7.35 | 66.18:6.04:7.44 | 384, 395(s), 430, 457, ~525 |
| 66 | 641.7 | 641 | $C_{38}H_{38}N_4O_2 \cdot Co$ | 71.13:5.97:8.73 | 70.95:6.11:8.67 | 380(s), 397, 429(s), 522 |
| 67 | 701.7 | 701 | $C_{40}H_{42}N_4O_4 \cdot Co$ | 68.47:6.03:7.98 | 68.63:5.97:8.06 | 388(s), 399, 420(s), 443(s), 522 |
| 68 | 761.8 | 761 | $C_{42}H_{46}N_4O_6 \cdot Co$ | 66.22:6.09:7.35 | 66.34:5.96:7.43 | 384, 395(s), 430, 457, ~524 |
| 69 | 669.7 | 669 | $C_{40}H_{42}N_4O_2 \cdot Co$ | 71.74:6.32:8.37 | 71.83:6.30:8.34 | 380(s), 397, 429(s), 522 |
| 70 | 753.9 | 753 | $C_{46}H_{54}N_4O_2 \cdot Co$ | 73.29:7.22:7.43 | 73.36:7.19:7.37 | 380(s), 397, 429(s), 522 |
| 71 | 669.7 | 669 | $C_{40}H_{42}N_4O_2 \cdot Co$ | 71.74:6.32:8.37 | 71.85:6.29:8.31 | 388, 419, 437, 522 |
| 72 | 753.9 | 753 | $C_{46}H_{54}N_4O_2 \cdot Co$ | 73.29:7.22:7.43 | 73.35:7.16:7.45 | 389, 419, 437, 521 |
| 73 | 729.8 | 729 | $C_{42}H_{46}N_4O_4 \cdot Co$ | 69.12:6.35:7.68 | 69.05:6.32:7.71 | 399, 420(s), 442(s), 388(s), 522 |
| 74 | 813.9 | 813 | $C_{48}H_{58}N_4O_4 \cdot Co$ | 70.83:7.18:6.88 | 70.77:7.23:6.90 | 399, 420(s), 442(s), 388(s), 521 |
| 75 | 729.8 | 729 | $C_{42}H_{46}N_4O_4 \cdot Co$ | 69.12:6.35:7.68 | 69.21:6.40:7.58 | 388(s), 399, 420(s), 442(s), 523 |
| 76 | 813.9 | 813 | $C_{48}H_{58}N_4O_4 \cdot Co$ | 70.83:7.18:6.88 | 70.76:7.23:6.92 | 388(s), 399, 420(s), 441(s), 522 |
| 77 | 785.9 | 785 | $C_{46}H_{54}N_4O_4 \cdot Co$ | 70.30:6.93:7.13 | 70.41:6.85:7.09 | 399, 420(s), 443(s), 388(s), 522 |
| 78 | 870.1 | 869 | $C_{52}H_{66}N_4O_4 \cdot Co$ | 71.79:7.65:6.44 | 71.87:7.59:6.51 | 399, 420(s), 443(s), 388(s), 522 |
| 79 | 785.9 | 785 | $C_{46}H_{54}N_4O_4 \cdot Co$ | 70.30:6.93:7.13 | 70.42:6.85:7.08 | 388(s), 399, 420(s), 442(s), 522 |
| 80 | 870.1 | 869 | $C_{52}H_{66}N_4O_4 \cdot Co$ | 71.79:7.65:6.44 | 71.92:7.58:6.41 | 388(s), 399, 420(s), 442(s), 522 |
| 81 | 813.9 | 813 | $C_{48}H_{58}N_4O_4 \cdot Co$ | 70.83:7.18:6.88 | 70.92:7.07:6.93 | 388(s), 399, 420(s), 442(s), 522 |
| 82 | 898.1 | 897 | $C_{54}H_{70}N_4O_4 \cdot Co$ | 72.22:7.86:6.24 | 72.18:7.99:6.17 | 388(s), 399, 420(s), 442(s), 522 |
| 83 | 813.9 | 813 | $C_{48}H_{58}N_4O_4 \cdot Co$ | 70.83:7.18:6.88 | 70.94:7.09:6.93 | 388(s), 399, 420(s), 442(s), 521 |

TABLE 1-2-continued

| Example No. | Mass Spectrum | | Formula | Elementary Analysis C:H:N (%) | | Visible Spectrum [DMF] (nm) |
|---|---|---|---|---|---|---|
| | Calcd. | Found | | Calcd. | Found | |
| 84 | 898.1 | 897 | $C_{54}H_{70}N_4O_4 \cdot Co$ | 72.22:7.86:6.24 | 72.33:7.78:6.12 | 388(s), 399, 420(s), 442(s), 522 |
| 85 | 813.9 | 813 | $C_{48}H_{58}N_4O_4 \cdot Co$ | 70.83:7.18:6.88 | 70.95:7.06:6.93 | 388(s), 399, 420(s), 442(s), 522 |
| 86 | 898.1 | 897 | $C_{54}H_{70}N_4O_4 \cdot Co$ | 72.22:7.86:6.24 | 72.34:7.91:6.11 | 388(s), 399, 420(s), 441(s), 522 |
| 87 | 813.9 | 813 | $C_{48}H_{58}N_4O_4 \cdot Co$ | 70.83:7.18:6.88 | 70.72:7.23:6.94 | 388(s), 399, 420(s), 441(s), 521 |
| 88 | 898.1 | 897 | $C_{54}H_{70}N_4O_4 \cdot Co$ | 72.22:7.86:6.24 | 72.30:7.79:6.18 | 388(s), 399, 420(s), 442(s), 522 |
| 89 | 813.9 | 813 | $C_{48}H_{58}N_4O_4 \cdot Co$ | 70.83:7.18:6.88 | 70.95:7.07:6.93 | 389(s), 399, 421(s), 443(s), 523 |
| 90 | 898.1 | 897 | $C_{54}H_{70}N_4O_4 \cdot Co$ | 72.22:7.86:6.24 | 72.10:7.93:6.29 | 388(s), 399, 420(s), 442(s), 522 |
| 91 | 813.9 | 813 | $C_{48}H_{58}N_4O_4 \cdot Co$ | 70.83:7.18:6.88 | 70.91:7.11:6.82 | 388(s), 399, 420(s), 443(s), 522 |
| 92 | 898.1 | 897 | $C_{54}H_{70}N_4O_4 \cdot Co$ | 72.22:7.86:6.24 | 72.32:7.77:6.21 | 388(s), 399, 420(s), 442(s), 521 |
| 93 | 842.0 | 841 | $C_{50}H_{62}N_4O_4 \cdot Co$ | 71.32:7.42:6.65 | 71.44:7.36:6.58 | 388(s), 399, 420(s), 442(s), 522 |
| 94 | 898.1 | 897 | $C_{54}H_{70}N_4O_4 \cdot Co$ | 72.22:7.86:6.24 | 72.29:7.78:6.19 | 388(s), 399, 420(s), 442(s), 521 |
| 95 | 954.2 | 953 | $C_{58}H_{78}N_4O_4 \cdot Co$ | 73.01:8.24:5.87 | 73.14:8.15:5.78 | 388(s), 399, 420(s), 441(s), 521 |
| 96 | 1010.3 | 1009 | $C_{62}H_{86}N_4O_4 \cdot Co$ | 73.71:8.58:5.55 | 73.65:8.63:5.48 | 388(s), 399, 420(s), 441(s), 522 |
| 97 | 789.8 | 789 | $C_{44}H_{50}N_4O_6 \cdot Co$ | 66.91:6.38:7.09 | 67.04:6.31:7.03 | 383, 395(s), 430, 457, 525 |
| 98 | 817.9 | 817 | $C_{46}H_{54}N_4O_6 \cdot Co$ | 67.55:6.66:6.85 | 67.54:6.58:6.92 | 383, 394(s), 430, 457, 525 |
| 99 | 845.9 | 845 | $C_{48}H_{58}N_4O_6 \cdot Co$ | 68.15:6.91:6.62 | 68.32:6.82:6.57 | 383, 395(s), 429, 457, 526 |
| 100 | 874.0 | 873 | $C_{50}H_{62}N_4O_6 \cdot Co$ | 68.71:7.15:6.41 | 68.63:7.17:6.50 | 383, 396(s), 429, 457, 526 |
| 101 | 902.1 | 901 | $C_{52}H_{66}N_4O_6 \cdot Co$ | 69.24:7.38:6.21 | 69.40:7.36:6.18 | 384, 396(s), 429, 457, 525 |
| 102 | 958.2 | 957 | $C_{56}H_{74}N_4O_6 \cdot Co$ | 70.20:7.78:5.85 | 70.08:7.84:5.92 | 383, 396(s), 430, 457, 525 |
| 103 | 1014.3 | 1013 | $C_{60}H_{82}N_4O_6 \cdot Co$ | 71.05:8.15:5.52 | 71.21:8.08:5.44 | 384, 395(s), 429, 458, 525 |
| 104 | 1070.4 | 1069 | $C_{64}H_{90}N_4O_6 \cdot Co$ | 71.82:8.48:5.23 | 71.88:8.55:5.12 | 384, 396(s), 429, 459, 525 |
| 105 | 958.2 | 957 | $C_{56}H_{74}N_4O_6 \cdot Co$ | 70.20:7.78:5.85 | 70.19:7.67:5.95 | 383, 396(s), 428, 457, 524 |
| 106 | 1126.5 | 1125 | $C_{68}H_{98}N_4O_6 \cdot Co$ | 72.50:8.77:4.97 | 72.43:8.68:5.13 | 385, 396(s), 429, 459, 525 |
| 107 | 902.1 | 901 | $C_{52}H_{66}N_4O_6 \cdot Co$ | 69.24:7.38:6.21 | 69.33:7.51:6.08 | 384, 396(s), 430, 458, 525 |
| 108 | 986.2 | 985 | $C_{58}H_{78}N_4O_6 \cdot Co$ | 70.64:7.97:5.68 | 70.75:8.12:5.56 | 384, 396(s), 430, 457, 525 |
| 109 | 986.2 | 985 | $C_{58}H_{78}N_4O_6 \cdot Co$ | 70.64:7.97:5.68 | 70.73:8.03:5.72 | 384, 396(s), 429, 458, 525 |
| 110 | 1154.5 | 1153 | $C_{70}H_{102}N_4O_6 \cdot Co$ | 72.82:8.91:4.85 | 72.78:9.11:4.72 | 384, 396(s), 429, 459, 525 |
| 111 | 958.2 | 957 | $C_{56}H_{74}N_4O_6 \cdot Co$ | 70.20:7.78:5.85 | 70.12:7.93:5.77 | 385, 395(s), 429, 458, 525 |
| 112 | 1042.3 | 1041 | $C_{62}H_{86}N_4O_6 \cdot Co$ | 71.44:8.32:5.38 | 71.40:8.43:5.32 | 385, 396(s), 429, 459, 525 |
| 113 | 986.2 | 985 | $C_{58}H_{78}N_4O_6 \cdot Co$ | 70.64:7.97:5.68 | 70.59:7.82:5.73 | 384, 396(s), 429, 459, 525 |
| 114 | 1154.5 | 1153 | $C_{70}H_{102}N_4O_6 \cdot Co$ | 72.82:8.91:4.85 | 72.76:9.03:4.82 | 384, 395(s), 429, 458, 525 |
| 115 | 958.2 | 957 | $C_{56}H_{74}N_4O_6 \cdot Co$ | 70.20:7.78:5.85 | 70.25:7.82:5.74 | 385, 396(s), 429, 459, 525 |
| 116 | 1042.3 | 1041 | $C_{62}H_{86}N_4O_6 \cdot Co$ | 71.44:8.32:5.38 | 71.32:8.36:5.43 | 384, 395(s), 429, 458, 525 |
| 117 | 986.2 | 985 | $C_{58}H_{78}N_4O_6 \cdot Co$ | 70.64:7.97:5.68 | 70.70:7.86:5.72 | 383, 396(s), 428, 457, 524 |
| 118 | 1154.5 | 1153 | $C_{70}H_{102}N_4O_6 \cdot Co$ | 72.82:8.91:4.85 | 72.87:8.98:4.72 | 384, 396(s), 429, 459, 525 |
| 119 | 958.2 | 957 | $C_{56}H_{74}N_4O_6 \cdot Co$ | 70.20:7.78:5.85 | 70.17:7.74:5.81 | 384, 395(s), 430, 457, 525 |
| 120 | 1042.3 | 1041 | $C_{62}H_{86}N_4O_6 \cdot Co$ | 71.44:8.32:5.38 | 71.62:8.25:5.33 | 383, 394(s), 430, 457, 525 |
| 121 | 1014.3 | 1013 | $C_{60}H_{82}N_4O_6 \cdot Co$ | 71.05:8.15:5.52 | 70.97:8.22:5.57 | 384, 397(s), 429, 459, 525 |
| 122 | 1098.4 | 1097 | $C_{66}H_{94}N_4O_6 \cdot Co$ | 72.17:8.63:5.10 | 72.32:8.55:5.02 | 384, 396(s), 430, 458, 524 |

TABLE 1-2-continued

| Example No. | Mass Spectrum Calcd. | Found | Formula | Elementary Analysis C:H:N (%) Calcd. | Found | Visible Spectrum [DMF] (nm) |
|---|---|---|---|---|---|---|
| 123 | 1182.6 | 1181 | $C_{72}H_{106}N_4O_6 \cdot Co$ | 73.13:9.04:4.74 | 73.22:8.97:4.70 | 385, 396(s), 429, 459, 525 |
| 124 | 1266.8 | 1265 | $C_{78}H_{118}N_4O_6 \cdot Co$ | 73.96:9.39:4.42 | 74.11:9.27:4.46 | 385, 396(s), 429, 459, 525 |
| 125 | 553.6 | 553 | $C_{34}H_{30}N_4 \cdot Co$ | 73.77:5.46:10.12 | 73.91:5.39:10.07 | 388, 419, 436(s), 524 |
| 126 | 613.6 | 613 | $C_{36}H_{34}N_4O_2 \cdot Co$ | 70.47:5.59:9.13 | 70.52:5.53:9.06 | 386(s), 400, 423(s), 442(s), 527 |
| 127 | 641.7 | 641 | $C_{38}H_{38}N_4O_2 \cdot Co$ | 71.13:5.97:8.93 | 71.06:6.12:8.87 | 386(s), 400, 421(s), 442(s), 527 |
| 128 | 669.7 | 669 | $C_{40}H_{42}N_4O_2 \cdot Co$ | 71.74:6.32:8.37 | 71.69:6.25:8.52 | 386(s), 400, 423(s), 442(s), 527 |
| 129 | 669.7 | 669 | $C_{40}H_{42}N_4O_2 \cdot Co$ | 71.74:6.32:8.37 | 71.67:6.24:8.55 | 385(s), 400, 423(s), 442(s), 527 |
| 130 | 697.8 | 697 | $C_{42}H_{46}N_4O_2 \cdot Co$ | 72.29:6.64:8.03 | 72.13:6.72:8.15 | 384(s), 400, 422(s), 443(s), 526 |
| 131 | 697.8 | 697 | $C_{42}H_{46}N_4O_2 \cdot Co$ | 72.29:6.64:8.03 | 72.41:6.47:8.10 | 384(s), 400, 422(s), 443(s), 526 |
| 132 | 697.8 | 697 | $C_{42}H_{46}N_4O_2 \cdot Co$ | 72.29:6.64:8.03 | 72.36:6.74:7.88 | 385(s), 400, 422(s), 442(s), 526 |
| 133 | 697.8 | 697 | $C_{42}H_{46}N_4O_2 \cdot Co$ | 72.29:6.64:8.03 | 72.44:6.52:7.97 | 386(s), 400, 423(s), 442(s), 527 |
| 134 | 725.8 | 725 | $C_{44}H_{50}N_4O_2 \cdot Co$ | 72.81:6.94:7.72 | 72.72:7.13:7.64 | 384(s), 400, 422(s), 443(s), 526 |
| 135 | 753.9 | 753 | $C_{46}H_{54}N_4O_2 \cdot Co$ | 73.29:7.22:7.43 | 73.22:7.13:7.59 | 384(s), 400, 423(s), 442(s), 525 |
| 136 | 782.0 | 781 | $C_{48}H_{58}N_4O_2 \cdot Co$ | 73.73:7.48:7.17 | 73.88:7.38:7.13 | 384(s), 400, 423(s), 443(s), 525 |
| 137 | 810.0 | 809 | $C_{50}H_{62}N_4O_2 \cdot Co$ | 74.14:7.72:6.92 | 74.08:7.86:6.85 | 384(s), 400, 423(s), 443(s), 525 |
| 138 | 669.7 | 669 | $C_{40}H_{42}N_4O_2 \cdot Co$ | 71.74:6.32:8.37 | 71.70:6.19:8.55 | 386(s), 400, 423(s), 442(s), 527 |
| 139 | 725.8 | 725 | $C_{44}H_{50}N_4O_2 \cdot Co$ | 72.81:6.94:7.72 | 72.91:6.89:7.67 | 385(s), 400, 423(s), 442(s), 527 |
| 140 | 782.0 | 781 | $C_{48}H_{58}N_4O_2 \cdot Co$ | 73.73:7.48:7.17 | 73.66:7.59:7.12 | 386(s), 400, 422(s), 442(s), 526 |
| 141 | 838.1 | 837 | $C_{52}H_{66}N_4O_2 \cdot Co$ | 74.53:7.94:6.69 | 74.47:7.86:6.83 | 386(s), 400, 423(s), 442(s), 526 |
| 142 | 894.2 | 893 | $C_{56}H_{74}N_4O_2 \cdot Co$ | 75.22:8.34:6.27 | 75.09:8.42:6.35 | 385(s), 400, 422(s), 442(s), 525 |
| 143 | 950.3 | 949 | $C_{60}H_{82}N_4O_2 \cdot Co$ | 75.84:8.70:5.90 | 75.99:8.62:5.78 | 384(s), 400, 422(s), 442(s), 526 |
| 144 | 1006.4 | 1005 | $C_{64}H_{90}N_4O_2 \cdot Co$ | 76.38:9.01:5.57 | 76.51:8.87:5.60 | 384(s), 400, 422(s), 442(s), 526 |
| 145 | 697.8 | 697 | $C_{42}H_{46}N_4O_2 \cdot Co$ | 72.29:6.64:8.03 | 72.36:6.72:7.87 | 386(s), 400, 421(s), 443(s), 527 |
| 146 | 782.0 | 781 | $C_{48}H_{58}N_4O_2 \cdot Co$ | 73.73:7.48:7.17 | 73.92:7.37:7.10 | 385(s), 400, 422(s), 443(s), 526 |
| 147 | 860.1 | 859 | $C_{54}H_{64}N_4O_2 \cdot Co$ | 75.41:7.50:6.51 | 75.38:7.46:6.49 | 385(s), 400, 422(s), 442(s), 526 |
| 148 | 950.3 | 949 | $C_{60}H_{82}N_4O_2 \cdot Co$ | 75.84:8.70:5.90 | 75.77:8.87:5.79 | 385(s), 400, 423(s), 443(s), 526 |
| 149 | 1034.4 | 1033 | $C_{66}H_{94}N_4O_2 \cdot Co$ | 76.63:9.16:5.42 | 76.81:9.07:5.35 | 384(s), 400, 422(s), 442(s), 525 |
| 150 | 1118.6 | 1117 | $C_{72}H_{106}N_4O_2 \cdot Co$ | 77.31:9.55:5.01 | 77.45:9.61:4.84 | 384(s), 400, 423(s), 443(s), 526 |
| 151 | 1202.8 | 1201 | $C_{78}H_{118}N_4O_2 \cdot Co$ | 77.89:9.89:4.66 | 77.81:10.02:4.59 | 384(s), 400, 422(s), 443(s), 526 |
| 152 | 525.5 | 525 | $C_{32}H_{26}N_4 \cdot Co$ | 73.14:4.99:10.66 | 73.28:4.95:10.58 | 379(s), 389, 418, 430(s), 522 |
| 153 | 645.6 | 645 | $C_{36}H_{34}N_4O_4 \cdot Co$ | 66.97:5.31:8.68 | 67.07:5.27:8.63 | 383, 428, 454, 527 |
| 154 | 673.7 | 673 | $C_{38}H_{38}N_4O_4 \cdot Co$ | 67.75:5.69:8.32 | 67.68:5.82:8.19 | 383, 428, 454, 527 |
| 155 | 701.7 | 701 | $C_{40}H_{42}N_4O_4 \cdot Co$ | 68.46:6.03:7.98 | 68.41:5.98:8.13 | 383, 429, 456, 528 |
| 156 | 701.7 | 701 | $C_{40}H_{42}N_4O_4 \cdot Co$ | 68.46:6.03:7.98 | 68.33:6.10:8.04 | 383, 429, 455, 527 |
| 157 | 729.8 | 729 | $C_{42}H_{46}N_4O_4 \cdot Co$ | 69.12:6.35:7.68 | 69.18:6.19:7.73 | 384, 428, 454, 526 |
| 158 | 729.8 | 729 | $C_{42}H_{46}N_4O_4 \cdot Co$ | 69.12:6.35:7.68 | 69.20:6.41:7.56 | 383, 428, 455, 527 |
| 159 | 729.8 | 729 | $C_{42}H_{46}N_4O_4 \cdot Co$ | 69.12:6.35:7.68 | 69.28:6.28:7.59 | 383, 428, 455, 527 |
| 160 | 729.8 | 729 | $C_{42}H_{46}N_4O_4 \cdot Co$ | 69.12:6.35:7.68 | 69.05:6.52:7.60 | 383, 429, 454, 527 |
| 161 | 757.8 | 757 | $C_{44}H_{50}N_4O_4 \cdot Co$ | 69.74:6.65:7.39 | 69.67:6.62:7.53 | 383, 429, 456, 527 |

TABLE 1-2-continued

| Example No. | Mass Spectrum Calcd. | Mass Spectrum Found | Formula | Elementary Analysis C:H:N (%) Calcd. | Elementary Analysis C:H:N (%) Found | Visible Spectrum [DMF] (nm) |
|---|---|---|---|---|---|---|
| 162 | 785.9 | 785 | $C_{46}H_{54}N_4O_4 \cdot Co$ | 70.30:6.93:7.13 | 70.17:7.02:7.18 | 383, 428, 454, 526 |
| 163 | 813.9 | 813 | $C_{48}H_{58}N_4O_4 \cdot Co$ | 70.83:7.18:6.88 | 70.92:7.03:6.93 | 383, 428, 454, 526 |
| 164 | 842.0 | 841 | $C_{50}H_{62}N_4O_4 \cdot Co$ | 71.32:7.42:6.65 | 71.39:7.53:6.47 | 383, 428, 455, 527 |
| 165 | 701.7 | 701 | $C_{40}H_{42}N_4O_4 \cdot Co$ | 68.46:6.03:7.98 | 68.51:6.05:8.01 | 383, 428, 454, 527 |
| 166 | 757.8 | 757 | $C_{44}H_{50}N_4O_4 \cdot Co$ | 69.74:6.65:7.39 | 69.70:6.74:7.33 | 384, 428, 456, 528 |
| 167 | 757.8 | 757 | $C_{44}H_{50}N_4O_4 \cdot Co$ | 69.74:6.65:7.39 | 69.58:6.72:7.30 | 384, 428, 456, 528 |
| 168 | 813.9 | 813 | $C_{48}H_{58}N_4O_4 \cdot Co$ | 70.83:7.18:6.88 | 70.68:7.23:6.94 | 383, 429, 455, 527 |
| 169 | 813.9 | 813 | $C_{48}H_{58}N_4O_4 \cdot Co$ | 70.83:7.18:6.88 | 70.78:7.13:6.82 | 384, 429, 456, 528 |
| 170 | 813.9 | 813 | $C_{48}H_{58}N_4O_4 \cdot Co$ | 70.83:7.18:6.88 | 70.91:7.15:6.80 | 384, 428, 456, 527 |
| 171 | 813.9 | 813 | $C_{48}H_{58}N_4O_4 \cdot Co$ | 70.83:7.18:6.88 | 70.95:7.07:6.92 | 383, 428, 455, 527 |
| 172 | 870.1 | 869 | $C_{52}H_{66}N_4O_4 \cdot Co$ | 71.79:7.65:6.44 | 71.85:7.72:6.29 | 384, 429, 455, 526 |
| 173 | 926.2 | 925 | $C_{56}H_{74}N_4O_4 \cdot Co$ | 72.62:8.05:6.05 | 72.84:7.98:5.97 | 383, 428, 455, 527 |
| 174 | 982.3 | 981 | $C_{60}H_{82}N_4O_4 \cdot Co$ | 73.37:8.41:5.70 | 73.23:8.60:5.61 | 383, 428, 455, 527 |
| 175 | 1038.4 | 1037 | $C_{64}H_{90}N_4O_4 \cdot Co$ | 74.03:8.74:5.40 | 73.98:8.67:5.57 | 383, 428, 455, 527 |
| 176 | 729.8 | 729 | $C_{42}H_{46}N_4O_4 \cdot Co$ | 69.12:6.35:7.68 | 68.97:6.42:7.74 | 384, 428, 454, 526 |
| 177 | 813.9 | 813 | $C_{48}H_{58}N_4O_4 \cdot Co$ | 70.83:7.18:6.88 | 70.91:7.24:6.73 | 384, 428, 454, 527 |
| 178 | 898.1 | 897 | $C_{54}H_{70}N_4O_4 \cdot Co$ | 72.22:7.86:6.24 | 72.37:7.78:6.17 | 383, 429, 455, 527 |
| 179 | 982.3 | 981 | $C_{60}H_{82}N_4O_4 \cdot Co$ | 73.37:8.41:5.70 | 73.28:8.57:5.62 | 383, 428, 454, 526 |
| 180 | 1066.4 | 1065 | $C_{66}H_{94}N_4O_4 \cdot Co$ | 74.33:8.88:5.25 | 74.28:8.79:5.44 | 383, 428, 454, 526 |
| 181 | 1150.6 | 1149 | $C_{72}H_{106}N_4O_4 \cdot Co$ | 75.16:9.29:4.87 | 75.03:9.36:4.92 | 383, 427, 454, 526 |
| 182 | 1234.8 | 1233 | $C_{78}H_{118}N_4O_4 \cdot Co$ | 75.87:9.63:4.54 | 75.94:9.51:4.60 | 383, 428, 455, 526 |
| 183 | 553.6 | 553 | $C_{34}H_{30}N_4 \cdot Co$ | 73.76:5.46:10.12 | 73.81:5.53:9.98 | 380(s), 393, 428(s), 522 |
| 184 | 722.0 | 721 | $C_{46}H_{54}N_4 \cdot Co$ | 76.53:7.54:7.76 | 76.50:7.49:7.72 | 380(s), 393, 428(s), 522 |
| 185 | 609.7 | 609 | $C_{38}H_{38}N_4 \cdot Co$ | 74.86:6.28:9.19 | 74.81:6.33:9.21 | 384, 398, 422, 439(s), 525 |
| 186 | 637.7 | 637 | $C_{40}H_{42}N_4 \cdot Co$ | 75.34:6.64:8.79 | 75.36:6.64:8.75 | 385, 398, 422, 438(s), 525 |
| 187 | 637.7 | 637 | $C_{40}H_{42}N_4 \cdot Co$ | 75.34:6.64:8.79 | 75.40:6.61:8.82 | 384, 397, 421, 438(s), 525 |
| 188 | 665.8 | 665 | $C_{42}H_{46}N_4 \cdot Co$ | 75.77:6.96:8.42 | 75.69:6.99:8.43 | 385, 397, 421, 438(s), 524 |
| 189 | 665.8 | 665 | $C_{42}H_{46}N_4 \cdot Co$ | 75.77:6.96:8.42 | 75.78:6.92:8.43 | 385, 397, 421, 438(s), 525 |
| 190 | 665.8 | 665 | $C_{42}H_{46}N_4 \cdot Co$ | 75.77:6.96:8.42 | 75.82:6.91:8.41 | 385, 397, 421, 438(s), 525 |
| 191 | 665.8 | 665 | $C_{42}H_{46}N_4 \cdot Co$ | 75.77:6.96:8.42 | 75.83:6.93:8.45 | 384, 398, 422, 439(s), 525 |
| 192 | 693.8 | 693 | $C_{44}H_{50}N_4 \cdot Co$ | 76.17:7.26:8.08 | 76.24:7.19:8.10 | 385, 397, 421, 438(s), 525 |
| 193 | 721.9 | 721 | $C_{46}H_{54}N_4 \cdot Co$ | 76.54:7.54:7.76 | 76.48:7.57:7.81 | 385, 397, 421, 438(s), 525 |
| 194 | 750.0 | 749 | $C_{48}H_{58}N_4 \cdot Co$ | 76.88:7.80:7.47 | 76.94:7.72:7.48 | 385, 397, 421, 438(s), 525 |
| 195 | 778.0 | 777 | $C_{50}H_{62}N_4 \cdot Co$ | 77.19:8.03:7.20 | 77.27:7.93:7.26 | 386, 397, 421, 438(s), 525 |
| 196 | 637.7 | 637 | $C_{40}H_{42}N_4 \cdot Co$ | 75.34:6.64:8.79 | 75.41:6.58:8.83 | 384, 398, 422, 439(s), 524 |
| 197 | 693.8 | 693 | $C_{44}H_{50}N_4 \cdot Co$ | 76.17:7.26:8.08 | 76.07:7.33:8.14 | 385, 398, 422, 439(s), 525 |
| 198 | 750.0 | 749 | $C_{48}H_{58}N_4 \cdot Co$ | 76.88:7.80:7.47 | 76.92:7.71:7.50 | 384, 397, 422, 439(s), 525 |
| 199 | 806.1 | 805 | $C_{52}H_{66}N_4 \cdot Co$ | 77.48:8.25:6.95 | 77.39:8.15:7.04 | 385, 398, 421, 439(s), 524 |
| 200 | 862.2 | 861 | $C_{56}H_{74}N_4 \cdot Co$ | 78.01:8.65:6.50 | 77.93:8.63:6.58 | 385, 398, 421, 439(s), 525 |

TABLE 1-2-continued

| Example No. | Mass Spectrum Calcd. | Found | Formula | Elementary Analysis C:H:N (%) Calcd. | Found | Visible Spectrum [DMF] (nm) |
|---|---|---|---|---|---|---|
| 201 | 918.3 | 917 | $C_{60}H_{82}N_4 \cdot Co$ | 78.48:9.00:6.10 | 78.60:8.92:6.05 | 385, 397, 421, 439(s), 525 |
| 202 | 974.4 | 973 | $C_{64}H_{90}N_4 \cdot Co$ | 78.89:9.31:5.75 | 78.93:9.30:5.72 | 386, 397, 421, 439(s), 525 |
| 203 | 665.8 | 665 | $C_{42}H_{46}N_4 \cdot Co$ | 75.77:6.96:8.42 | 75.85:6.92:8.38 | 385, 397, 421, 438(s), 524 |
| 204 | 750.0 | 749 | $C_{48}H_{58}N_4 \cdot Co$ | 76.88:7.80:7.47 | 76.95:7.74:7.44 | 385, 397, 421, 438(s), 525 |
| 205 | 834.1 | 833 | $C_{54}H_{70}N_4 \cdot Co$ | 77.76:8.46:6.72 | 77.64:8.53:6.80 | 385, 397, 421, 439(s), 525 |
| 206 | 918.3 | 917 | $C_{60}H_{82}N_4 \cdot Co$ | 78.48:9.00:6.10 | 78.53:8.94:6.07 | 385, 397, 421, 439(s), 525 |
| 207 | 1002.4 | 1001 | $C_{66}H_{94}N_4 \cdot Co$ | 79.08:9.45:5.59 | 79.03:9.51:5.57 | 385, 397, 421, 439(s), 525 |
| 208 | 1086.6 | 1085 | $C_{72}H_{106}N_4 \cdot Co$ | 79.59:9.83:5.16 | 79.66:9.80:5.11 | 385, 397, 421, 439(s), 525 |
| 209 | 1170.8 | 1169 | $C_{78}H_{118}N_4 \cdot Co$ | 80.02:10.16:4.79 | 79.96:10.20:4.83 | 386, 397, 421, 438(s), 525 |

*(1): (s) means a shoulder of a peak.
*(2): ~ means a center wave length of a plateau peak.

EXAMPLE 210

The oxygen reduction catalyst activities of Co-TAA as obtained in Examples 1, 3, 8, 19, 93, 96, 126, 140, 154, 168, 188 and 198 were measured. The measurement was carried out in accordance with the cyclic voltammetry method by using a potentiostat.

In 1 l of chloroform of 1 l of N,N-dimethylformamide was dissolved 800 mg of Co-TAA, and in the solution was dipped a Glassy Carbon (trade name; product of Tokai Denkyoku Seizo K.K.) whose surface was mirror-plane finished for 30 minutes. The Glassy Carbon was taken out from the solution and left to stand to dryness. The treated glassy carbon was employed as a cathode electrode. A platinum coil was employed as an anode electrode and a calomel electrode was employed as a reference electrode. An electrolytic solution was 1N sulfuric acid and the measurement temperature was 25° C.

The measurement was carried out by introducing a high-purity oxygen gas into the electrolytic solution and recording the electric current generated by varying the voltage from +800 mV to −600 mV at a velocity of 25 mV/sec.

The catalyst activity was evaluated by the generated electric current value at +375 mV. The measurement was repeated 10 times and the catalyst life was evaluated by the tenth measurement result, that is, the tenth catalyst activity. The measurement results are shown in Table 2.

TABLE 2

| Catalyst obtained in Example No. | Catalyst Activity ($\mu A/cm^2$) | Catalyst Life ($\mu A/cm^2$) |
|---|---|---|
| 1 | 125 | 125 |
| 3 | 165 | 165 |
| 8 | 138 | 138 |
| 19 | 167 | 167 |
| 93 | 158 | 158 |
| 96 | 157 | 157 |
| 126 | 145 | 145 |
| 140 | 152 | 152 |
| 154 | 150 | 149 |
| 168 | 144 | 144 |
| 188 | 144 | 144 |
| 198 | 147 | 147 |

COMPARATIVE EXAMPLE

The catalyst activity and the catalyst life of Co-TAA having the formula (VII) were measured by the same methods as those of this invention. The Co-TAA has a catalyst activity of 145 $\mu A/cm^2$ and a catalyst life of 30 $\mu A/cm^2$.

EXAMPLE 211

Step 1

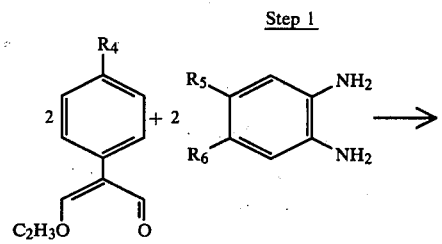

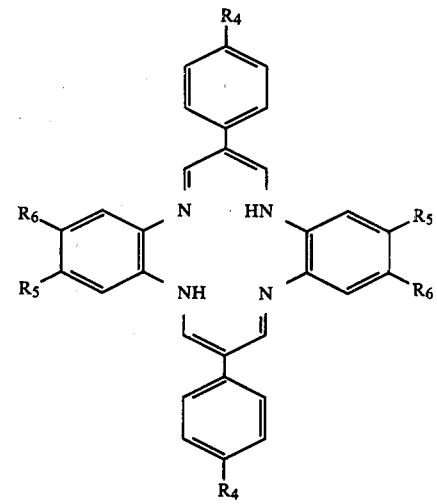

In 25 ml of N,N-dimethylformamide were dissolved 0.02 mol of a β-ethoxy-α-arylacrolein and 0.02 mol of an o-phenylenediamine derivative as set forth in Table 3. The solution was refluxed under heating for 5 hours. The reaction solution was cooled to 25° C. to give a compound. The compound obtained was separated by filtration, washed with methanol and dried. The yield is shown in Table 3. All the compounds were confirmed as tetraazaannulene derivatives.

TABLE 3

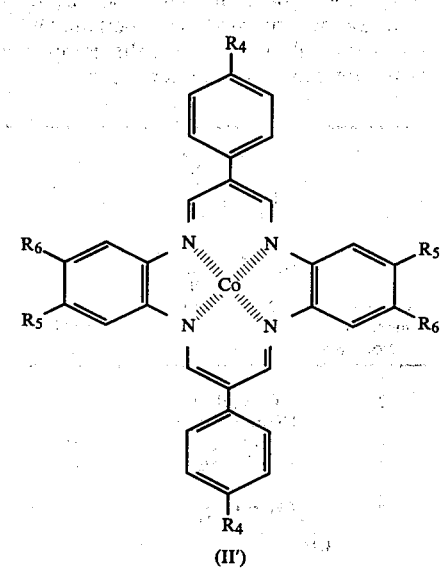

| Experimental No. | $C_2H_5O$ $R_4$ | $R_5$ | $R_6$ | Yield (%) |
|---|---|---|---|---|
| 1 | H— | H— | H— | 34 |
| 2 | $O_2N$— | H— | H— | 26 |
| 3 | $CH_3O$— | H— | H— | 27 |
| 4 | $CH_3$— | H— | H— | 31 |
| 5 | NC— | H— | H— | 30 |
| 6 | HOOC— | H— | H— | 30 |
| 7 | Cl— | H— | H— | 27 |
| 8 | Br— | H— | H— | 28 |
| 9 | H— | $CH_3$— | $CH_3$— | 18 |
| 10 | H— | $CH_3$— | $CH_3$— | 29 |
| 11 | H— | Cl— | H— | 16 |
| 12 | H— | Cl— | Cl— | 33 |
| 13 | H— | $CH_3O$— | H— | 3 |
| 14 | H— | COOH— | $CH_3$— | 3 |
| 15 | H— | $O_2N$— | H— | 5 |

Step 2

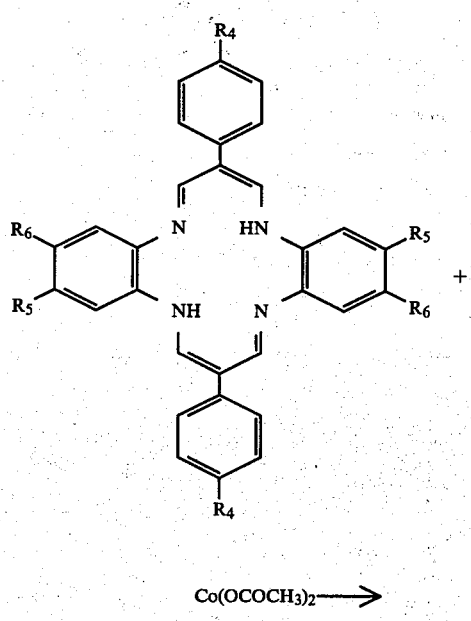

Co(OCOCH₃)₂ ⟶

-continued

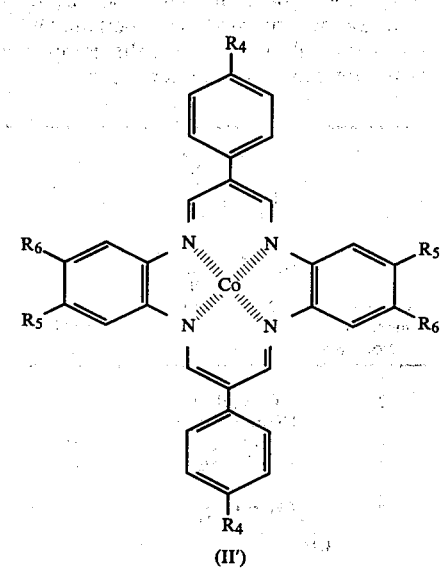

(II')

In 10 ml of N,N-dimethylformamide were dissolved 5 millimol of each of the tetraazaannulene derivatives obtained in Step 1 and 5 millimol of cobalt (II) acetate tetrahydrate, and the solution was refluxed under heating for 5 hours. The reaction solution was cooled to 25° C. to give a compound. The compound was filtered, washed with methanol and dried. All the compounds were obtained at a yield of 90~95%, and identified as Co-TAA having the formula (II') by elementary analysis, the mass spectra and visible spectra thereof.

EXAMPLE 212

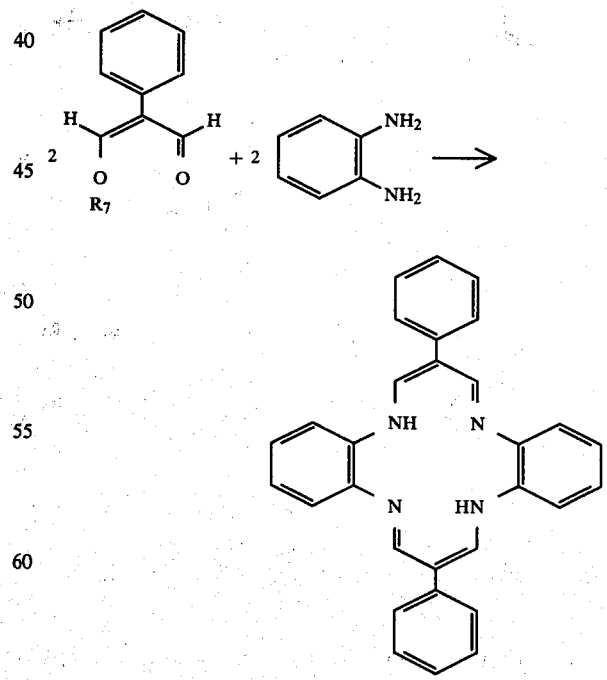

In 25 ml of N,N-dimethylformamide were dissolved 0.02 mol of a β-alkoxy-α-phenylacrolein as set forth in Table 4 and 2.16 g (0.02 mol) of o-phenylenediamine, and the solution was refluxed under heating for 5 hours. The reaction solution was cooled to 25° C. to give a compound. The compound obtained was separated by filtration, washed with methanol and dried. The yield is shown in Table 4. All the compounds were confirmed as the tetraazaannulene derivative.

TABLE 4

[Structure: phenyl group attached to C=C with two CHO groups, R7 substituents shown as H—C(OR7)=C—C(=O)H style malonaldehyde derivative]

| Experimental No. | R7 | Yield (%) | Visible Spectrum [in DMF] (nm) |
|---|---|---|---|
| 1 | $CH_3-$ | 33 | 390, 427, 446 |
| 2 | $CH_3CH_2-$ | 34 | 390, 427, 446 |
| 3 | $CH_3CH_2CH_2-$ | 32 | 390, 427, 446 |
| 4 | $CH_3(CH_2)_3-$ | 33 | 390, 427, 446 |
| 5 | $CH_3(CH_2)_5-$ | 34 | 390, 427, 446 |
| 6 | cyclohexyl | 30 | 390, 427, 446 |
| 7 | $(CH_3)_2CH-$ | 32 | 390, 427, 446 |

EXAMPLE 213

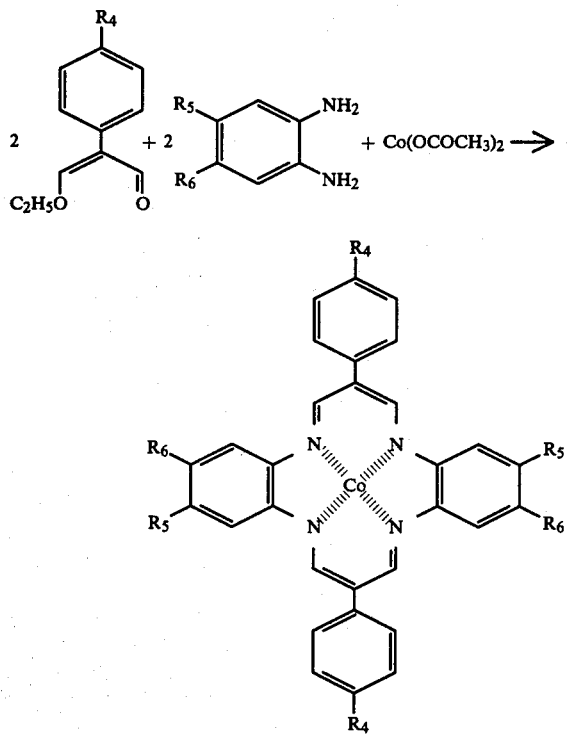

In 20 ml of N,N-dimethylformamide were dissolved 5 millimol of an o-phenylenediamine derivative as set forth in Table 5 and 623 mg (2.5 millimol) of cobalt (II) acetate tetrahydrate, and the solution was heated at 120° C. The solution was added with 5 millimol of a β-ethoxy-α-arylacrolein as set forth in Table 5 and refluxed under heating for 5 hours. The reaction solution was cooled, filtered, washed with methanol and dried to give a compound at a yield as shown in Table 5. All the compounds were confirmed as Co-TAA.

TABLE 5

[Structure showing β-ethoxy-α-arylacrolein with R4 on phenyl and o-phenylenediamine with R5, R6]

| Experimental No. | R4 | R5 | R6 | Yield (%) |
|---|---|---|---|---|
| 1 | H— | H— | H— | 52 |
| 2 | $O_2N-$ | H— | H— | 38 |
| 3 | $CH_3O-$ | H— | H— | 37 |
| 4 | $CH_3-$ | H— | H— | 37 |
| 5 | NC— | H— | H— | 40 |
| 6 | H— | $CH_3-$ | H— | 31 |
| 7 | H— | $CH_3-$ | $CH_3-$ | 35 |
| 8 | H— | Cl— | H— | 22 |
| 9 | H— | Cl— | Cl— | 40 |
| 10 | H— | $CH_3O-$ | H— | 8 |
| 11 | $CH_3O-$ | Cl— | H— | 47 |
| 12 | $O_2N-$ | $CH_3-$ | H— | 36 |
| 13 | $CH_3-$ | $CH_3-$ | $CH_3-$ | 66 |

EXAMPLE 214 *

The same procedures as described in Experimental No. 1 of Example 213 were repeated except that a β-ethoxy-α-arylacrolein as set forth in Table 6 was employed instead of the β-ethoxy-α-phenylacrolein. All the compounds obtained were confirmed as Co-TAA. The yield of Co-TAA is shown in Table 6.

TABLE 6

[Structure of β-ethoxy-α-arylacrolein with R4 substituent]

| Experimental No. | R4 | Position of R4 | Yield (%) |
|---|---|---|---|
| 1 | $CH_3-$ | ortho | 31 |
| 2 | $CH_3O-$ | ortho | 25 |
| 3 | $CH_3-$ | meta | 43 |
| 4 | $CH_3O$ | meta | 37 |
| 5 | Cl— | ortho | 28 |
| 6 | Cl— | meta | 34 |

EXAMPLE 215

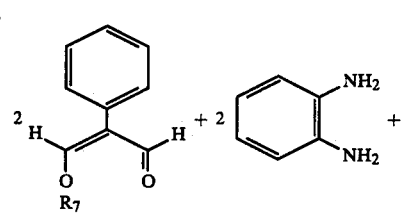

-continued

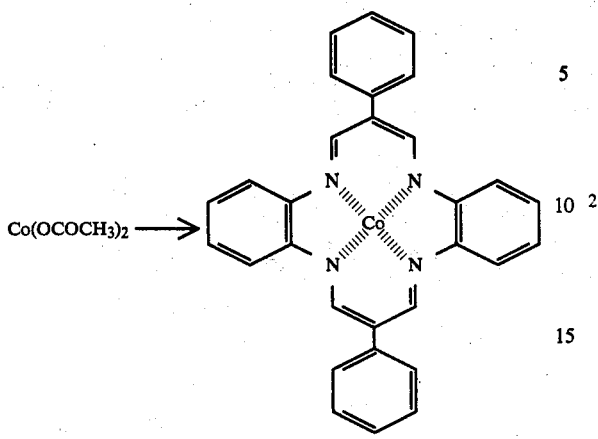

Co(OCOCH₃)₂ →

In 20 ml of N,N-dimethylformamide were dissolved 5 millimol (540 mg) of o-phenylenediamine and 2.5 millimol (623 mg) of cobalt (II) acetate tetrahydrate, and the solution was heated to 120° C. Then, the solution was added with 5 millimol of a β-alkoxy-α-phenylacrolein as set forth in Table 7, and refluxed under heating for 5 hours. The reaction solution was cooled, filtered, washed with methanol and dried to give a compound at a yield as shown in Table 7. All the compounds were confirmed as Co-TAA.

TABLE 7

| Experimental No. | $R_7$ | Yield (%) | Visible Spectrum [in DMF] (nm) |
|---|---|---|---|
| 1 | CH₃ | 52 | 377(s)*, 388, 425(s), 522 |
| 2 | CH₃CH₂— | 54 | 377(s), 388, 425(s), 522 |
| 3 | CH₃CH₂CH₂— | 50 | 377(s), 388, 425(s), 522 |
| 4 | CH₃(CH₂)₃— | 51 | 377(s), 388, 425(s), 522 |
| 5 | CH₃(CH₂)₅— | 50 | 377(s), 388, 425(s), 522 |
| 6 | cyclohexyl— | 49 | 377(s), 388, 425(s), 522 |
| 7 | (CH₃)₂CH— | 53 | 377(s), 388, 425(s), 522 |

*(s) means a shoulder of a peak

EXAMPLE 216

Step 1

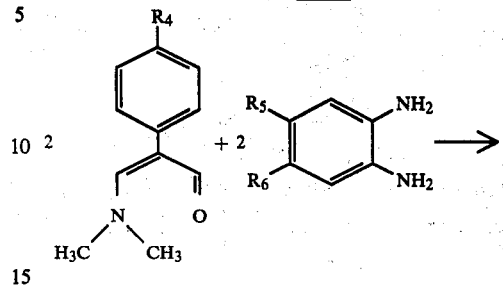

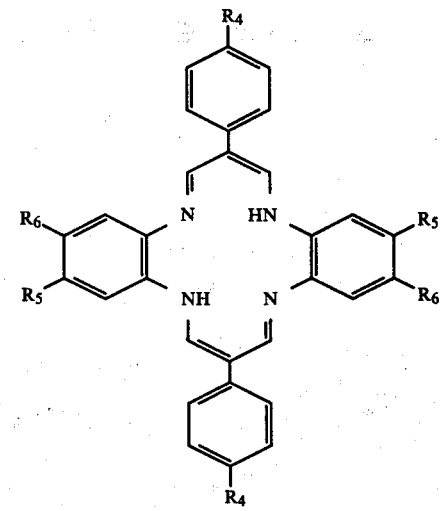

In 30 ml of N,N-dimethylformamide were dissolved 0.02 mol of a β-dimethylamino-α-arylacrolein and 0.02 mol of an o-phenylenediamine derivative as set forth in Table 8, and the solution was refluxed under heating for 5 hours. The reaction solution was cooled to 25° C. to separate a compound. The compound obtained was separated by filtration, washed with methanol and dried under reduced pressure. The yield is shown in Table 8. All the compounds were confirmed as tetraazaannulene derivatives.

TABLE 8

| Experimental No. | $R_4$ | $R_5$ | $R_6$ | Yield (%) |
|---|---|---|---|---|
| 1 | H— | H— | H— | 54 |
| 2 | O₂N— | H— | H— | 39 |
| 3 | CH₃O— | H— | H— | 39 |
| 4 | CH₃— | H— | H— | 49 |
| 5 | H— | CH₃— | H— | 25 |
| 6 | H— | CH₃— | CH₃— | 52 |
| 7 | H— | CH₃O— | H— | 5 |
| 8 | CH₃— | CH₃O— | H— | 4 |
| 9 | CH₃— | CH₃O— | CH₃O— | 7 |
| 10 | O₂N— | CH₃— | CH₃— | 59 |
| 11 | CH₃O— | CH₃O— | H— | 8 |

TABLE 8-continued

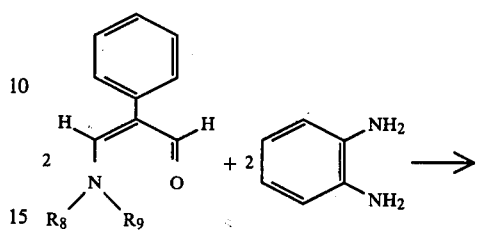

| Experimental No. | R4 | R5 | R6 | Yield (%) |
|---|---|---|---|---|
| 12 | C₂H₅OC(=O)— | CH₃O— | H— | 6 |
| 13 | CH₃O— | CH₃O— | CH₃O— | 10 |

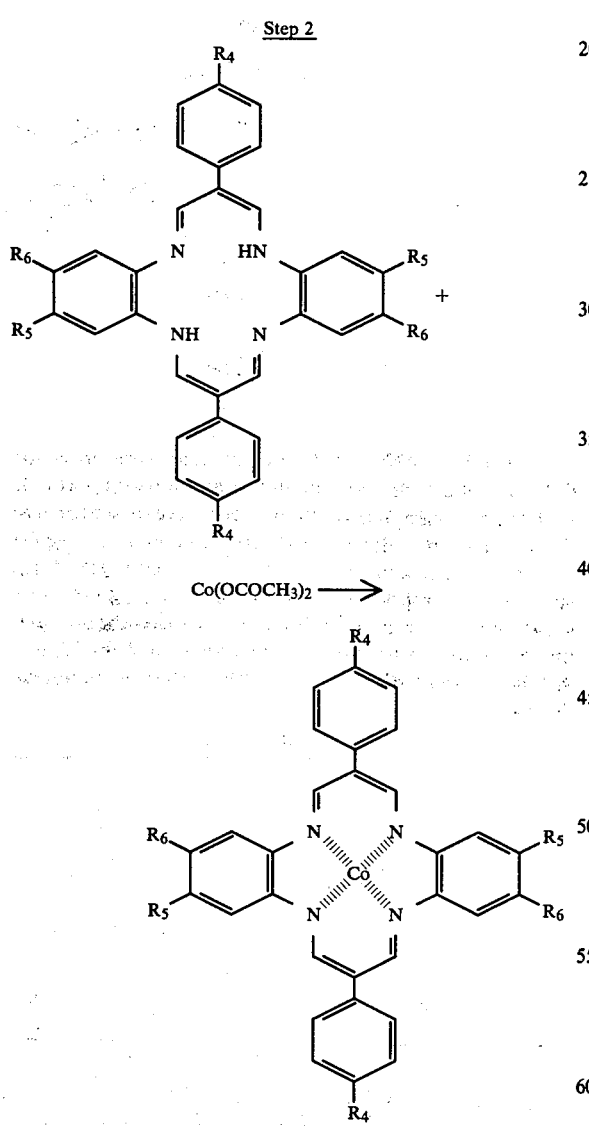

Step 2

Co(OCOCH₃)₂ →

In 10 ml of N,N-dimethylformamide were dissolved 5 millimol of each of the tetraazaannulene derivatives obtained and 5 ml of cobalt (II) acetate tetrahydrate, and the solution was refluxed under heating for 5 hours. The reaction solution was cooled to 25° C. to give a compound. The compound obtained was separated by filtration, washed with methanol and dried. All the compounds were obtained at a yield of 90–95%, and confirmed as Co-TAA.

EXAMPLE 217

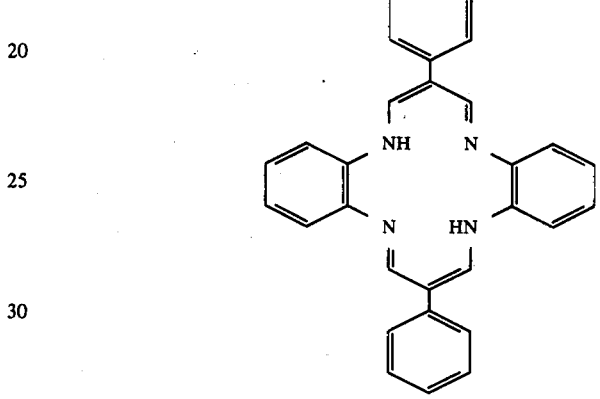

In 30 ml of N,N-dimethylformamide were dissolved 0.02 mol of a β-dialkylamino-α-phenylacrolein as set forth in Table 9 and 2.16 g (0.02 mol) of o-phenylenediamine, and the solution was refluxed under heating for 5 hours. The reaction solution was cooled to 25° C. to give a compound. The compound obtained was separated by filtration, washed with methanol and dried under reduced pressure. The yield is shown in Table 9. All the compounds were confirmed as the tetraazaannulene derivative.

TABLE 9

| Experimental No. | R8 | R9 | Yield (%) | Visible Spectrum [in DMF] (nm) |
|---|---|---|---|---|
| 1 | CH₃— | CH₃— | 54 | 390, 427, 446 |
| 2 | CH₃CH₂— | CH₃CH₂— | 51 | 390, 427, 446 |
| 3 | CH₃— | CH₃CH₂— | 53 | 390, 427, 446 |
| 4 | CH₃— | CH₃(CH₂)₃— | 50 | 390, 427, 446 |
| 5 | CH₃(CH₂)₃— | CH₃(CH₂)₃— | 52 | 390, 427, 446 |

In N,N-dimethylformamide were dissolved the tetraazaannulene obtained and the equimolar amount of cobalt (II) acetate tetrahydrate, and the solution was refluxed under heating for 5 hours. The reaction solution was cooled to 25° C. to give a compound. The compound obtained was separated by filtration, washed with methanol and dried. All the compounds were obtained in a yield of 90–95%, and confirmed as Co-TAA.

EXAMPLE 218

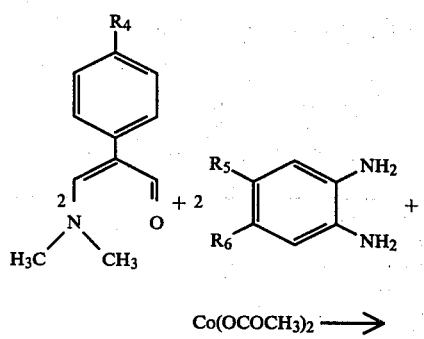

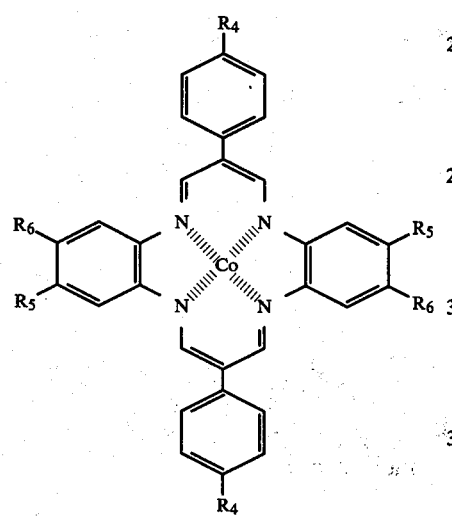

In 20 ml of N,N-dimethylformamide were dissolved 5 millimol of an o-phenylenediamine derivative as set forth in Table 10 and 623 mg (2.5 millimol) of cobalt (II) acetate tetrahydrate, and the solution was heated at 120° C. for 30 minutes. The solution was added with 5 millimol of a β-dimethylamino-α-arylacrolein as set forth in Table 10, and refluxed under heating for 5 hours. The reaction solution was cooled, filtered, washed with methanol and dried to give a compound. The yield is shown in Table 10. All the compounds were confirmed as Co-TAA.

TABLE 10

| Experimental No. | $R_4$ | $R_5$ | $R_6$ | Yield (%) |
|---|---|---|---|---|
| 1 | CH$_3$— | H— | H— | 58 |
| 2 | O$_2$N— | H— | H— | 63 |
| 3 | CH$_3$O— | H— | H— | 60 |
| 4 | Cl— | H— | H— | 67 |
| 5 | H— | CH$_3$— | H— | 45 |
| 6 | H— | CH$_3$— | CH$_3$— | 72 |

TABLE 10-continued

| Experimental No. | $R_4$ | $R_5$ | $R_6$ | Yield (%) |
|---|---|---|---|---|
| 7 | H— | Cl— | Cl— | 54 |
| 8 | CH$_3$— | CH$_3$O— | H— | 9 |
| 9 | CH$_3$— | CH$_3$O— | CH$_3$O— | 14 |
| 10 | NC— | Cl— | Cl— | 67 |
| 11 | C$_2$H$_5$OC(O)— | CH$_3$O— | H— | 10 |
| 12 | O$_2$N— | CH$_3$— | CH$_3$— | 73 |
| 13 | CH$_3$O— | CH$_3$O— | H— | 15 |
| 14 | CH$_3$O— | CH$_3$O— | CH$_3$O— | 17 |

EXAMPLE 219

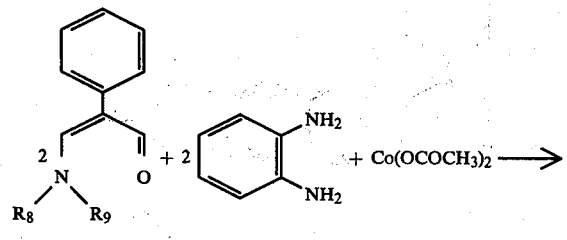

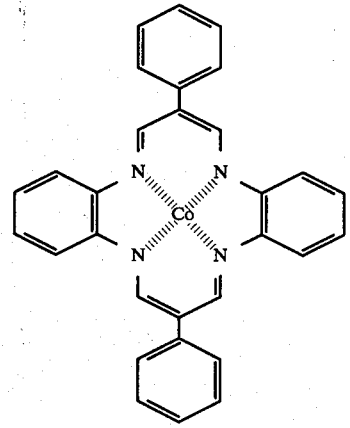

In 20 ml of N,N-dimethylformamide were dissolved 5 millimol (540 mg) of o-phenylenediamine and 2.5 millimol (623 mg) of cobalt (II) acetate tetrahydrate, and the solution was heated at 120° C. for 30 minutes. The solution was added with 5 millimol of a β-dialkylamino-α-phenylacrolein as set forth in Table 11, and refluxed under heating for 3 hours. The reaction solution was cooled, filtered, washed with methanol and dried to give a compound at a yield as shown in Table 11. All the compound obtained were confirmed as Co-TAA.

TABLE 11

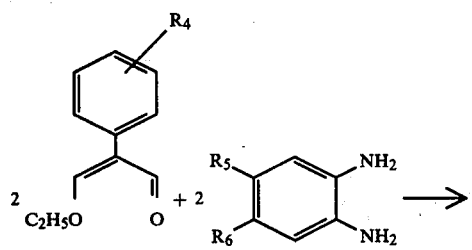

| Experimental No. | $R_8$ | $R_9$ | Yield (%) | Visible Spectrum [in DMF] (nm) |
|---|---|---|---|---|
| 1 | $CH_3-$ | $CH_3-$ | 72 | 377(s)*, 388 425(s), 522 |
| 2 | $CH_3CH_2-$ | $CH_3CH_2-$ | 63 | 377(s), 388 425(s), 522 |
| 3 | $CH_3-$ | $CH_3CH_2-$ | 68 | 377(s), 388 425(s), 522 |
| 4 | $CH_3-$ | $CH_3(CH_2)_3-$ | 64 | 377(s), 388 425(s), 522 |
| 5 | $CH_3(CH_2)_3-$ | $CH_3(CH_2)_3-$ | 65 | 377(s), 388 425(s), 522 |

TABLE 12

| Experimental No. | $C_2H_5O$ $R_4$ | O Position of $R_4$ | $R_5$ | $R_6$ | Yield (%) |
|---|---|---|---|---|---|
| 1 | $CH_3-$ | ortho | $H-$ | $H-$ | 13 |
| 2 | $CH_3-$ | meta | $H-$ | $H-$ | 18 |
| 3 | $CH_3O-$ | ortho | $H-$ | $H-$ | 15 |
| 4 | $CH_3O-$ | meta | $H-$ | $H-$ | 17 |
| 5 | $Cl-$ | ortho | $H-$ | $H-$ | 14 |
| 6 | $Cl-$ | meta | $H-$ | $H-$ | 19 |
| 7 | $O_2N-$ | ortho | $H-$ | $H-$ | 17 |
| 8 | $O_2N-$ | meta | $H-$ | $H-$ | 21 |
| 9 | $CH_3O-$ | ortho | $Cl-$ | $Cl-$ | 16 |
| 10 | $CH_3O-$ | meta | $Cl-$ | $Cl-$ | 20 |

EXAMPLE 220

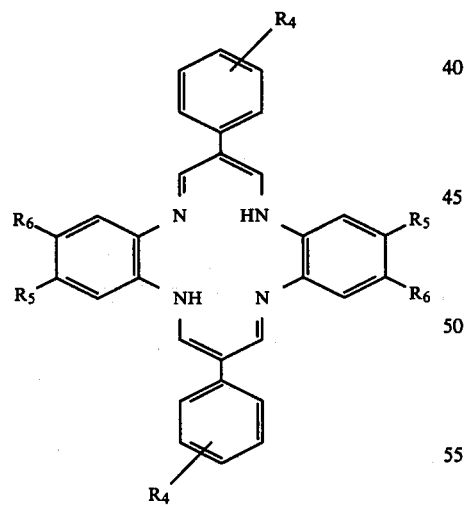

In 25 ml of N,N-dimethylformamide were dissolved 0.02 mol of a β-ethoxy-α-arylacrolein and 0.02 mol of an o-phenylenediamine derivative as set forth in Table 12, and the solution was refluxed under heating for 5 hours. The reaction solution was cooled to 25° C. to give a compound. The compound obtained was separated by filtration, washed with methanol and dried. The yield is shown in Table 12. All the compounds were confirmed as tetraazaannulene derivatives.

EXAMPLE 221

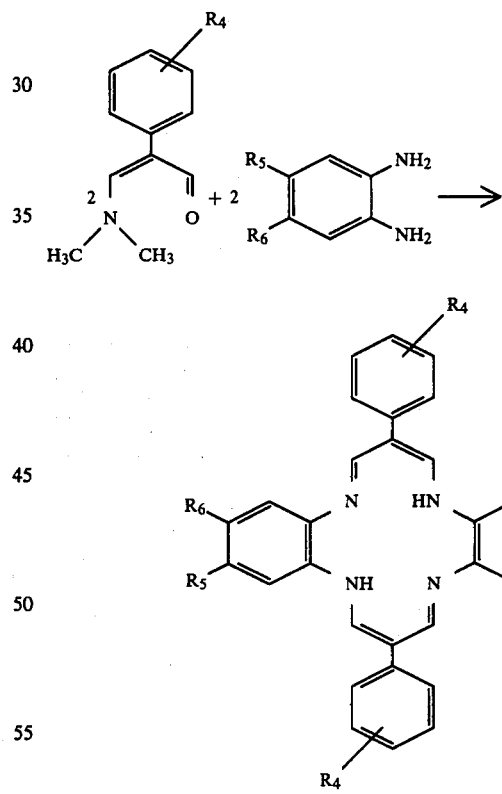

In 25 ml of N,N-dimethylformamide were dissolved 0.02 mol of a β-dimethylamino-α-arylacrolein and 0.02 mol of an o-phenylenediamine derivative as set forth in Table 13, and the solution was refluxed under heating for 5 hours. The reaction solution was cooled to 25° C. to give a compound. The compound obtained was separated by filtration, washed with methanol and dried. The yield is shown in Table 13. All the compounds were confirmed as tetraazaannulele derivatives.

TABLE 13

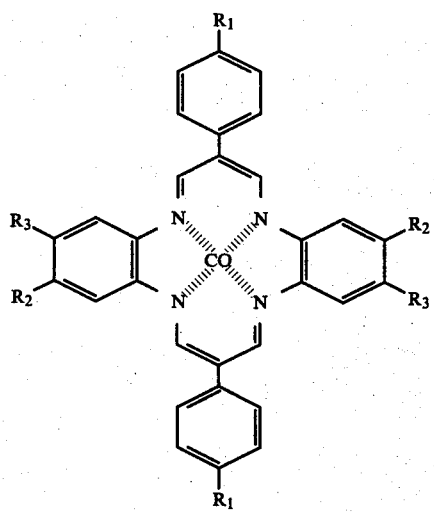

| Experimental No. | $R_4$ | Position of $R_4$ | $R_5$ | $R_6$ | Yield (%) |
|---|---|---|---|---|---|
| 1 | $CH_3-$ | ortho | H— | H— | 15 |
| 2 | $CH_3-$ | meta | H— | H— | 22 |
| 3 | $CH_3O-$ | ortho | H— | H— | 20 |
| 4 | $CH_3O-$ | meta | H— | H— | 23 |
| 5 | Cl— | ortho | H— | H— | 21 |
| 6 | Cl— | meta | H— | H— | 25 |
| 7 | $O_2N-$ | ortho | H— | H— | 24 |
| 8 | $O_2N-$ | meta | H— | H— | 27 |
| 9 | $CH_3O-$ | ortho | Cl— | Cl— | 23 |
| 10 | $CH_3O-$ | meta | Cl— | Cl— | 28 |

What is claimed is:

1. A tetraazaannulene cobalt complex compound having the general formula (I);

(I)

wherein $R_1$, $R_2$ and $R_3$ each independently is a hydrogen atom, a $C_{1-8}$ alkoxy group or a $C_{1-8}$ alkyl group but in case of one of $R_1$, $R_2$ and $R_3$ being a hydrogen atom the other two groups are not hydrogen atoms at the same time, and when $R_1$ is a methyl group $R_2$ and $R_3$ are not hydrogen atoms at the same time.

2. The compound of claim 1, wherein $R_1$ is a $C_{1-8}$ alkoxy group.

3. The compound of claim 2, wherein $R_2$ and $R_3$ each independently is a $C_{1-8}$ alkoxy group.

4. The compound of claim 2, wherein one of $R_2$ and $R_3$ is a $C_{1-8}$ alkoxy group and the other group is a hydrogen atom.

5. The compound of claim 2, wherein $R_2$ and $R_3$ each independently is a hydrogen atom or a $C_{1-8}$ alkyl group.

6. The compound of claim 1, wherein $R_1$ is a $C_{1-8}$ alkyl group.

7. The compound of claim 6, wherein $R_2$ and $R_3$ each independently is a $C_{1-8}$ alkoxy group.

8. The compound of claim 6, wherein $R_2$ and $R_3$ each independently is a $C_{1-8}$ alkyl group or a hydrogen atom.

9. A method for preparing a tetraazaannulene cobalt complex compound having the general formula (II);

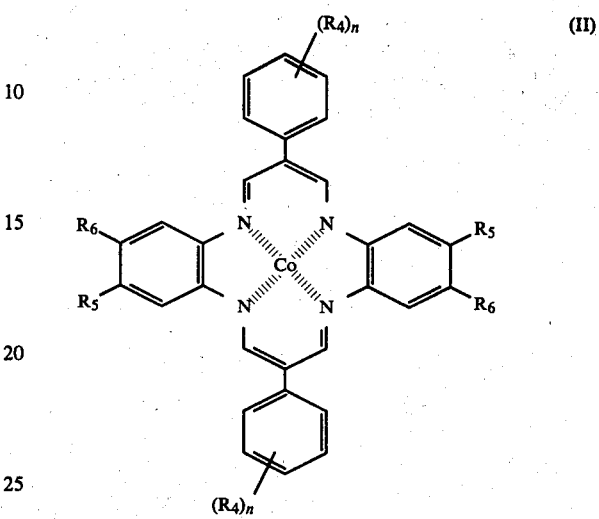

(II)

wherein $R_4$ is a hydrogen atom, a $C_{1-8}$ alkoxy group, a $C_{1-8}$ alkyl group, a halogen atom, a nitro group, a cyano group, a $C_{1-8}$ alkylcarboxyl group, a hydroxyl group, a carboxyl group, a $C_{1-8}$ alkoxycarbonyl group, a carbamoyl group, a N,N-di $C_{1-6}$ alkylamino group, a $C_{1-8}$ alkylamido group, an amino group, a $C_{1-8}$ alkoxycarbonyl $C_{1-3}$ alkyl group or a N,N-di $C_{1-6}$ alkylamino $C_{1-3}$ alkyl group;

n is integer of 1 to 5; and $R_5$ and $R_6$ each independently is a hydrogen atom, a $C_{1-8}$ alkoxy group, a $C_{1-8}$ alkyl group, a halogen atom, a nitro group, a cyano group, a $C_{1-8}$ alkylcarboxyl group, a hydroxyl group, a carboxyl group, a $C_{1-8}$ alkoxycarbonyl group, a carbamoyl group, a N,N-di $C_{1-6}$ alkylamino group, a $C_{1-8}$ alkylamido group, or a $C_{1-8}$ alkoxycarbonyl $C_{1-3}$ alkyl group;

which comprises reacting a β-alkoxy-α-arylacrolein of the general formula (III);

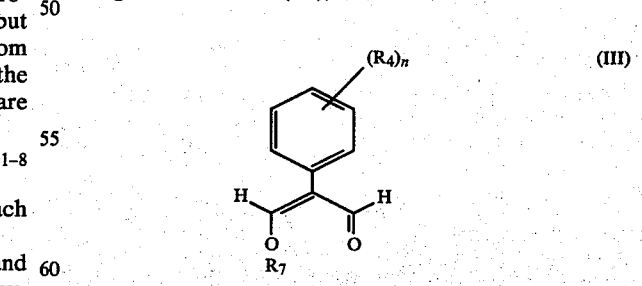

(III)

wherein $R_4$ and n are the same as defined in the formula (II); and $R_7$ is a $C_{1-6}$ alkyl group;

with an o-phenylenediamine derivative of the general formula (IV);

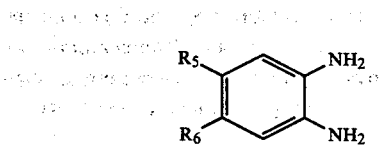

wherein R₅ and R₆ are the same as defined in the formula (II); to prepare a tetraazaannulene derivative of the formula (V);

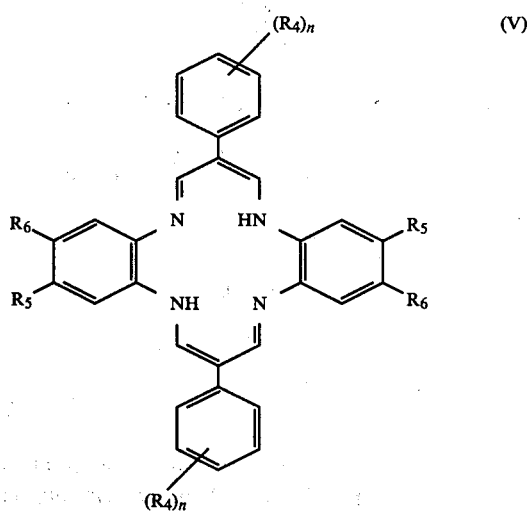

wherein R₄, R₅, R₆ and n are the same as defined in the formula (II); and reacting the tetraazaannulene derivative of the formula (V) with a cobalt compound.

10. The method of claim 9, wherein the reaction between the β-alkoxy-α-arylacrolein of the general formula (III) and the o-phenylenediamine derivative of the general formula (IV) is carried out at 50°–250° C.

11. The method of claim 9, wherein the reaction between the tetraazaannulene derivative of the formula (V) and the cobalt compound is carried out at 50°–250° C.

12. A method for preparing a tetraazaannulene cobalt complex compound having the general formula (II) as defined in claim 9 which comprises reacting a -alkoxy-arylacrolein of the general formula (III) as defined in claim 9 and an o-phenylenediamine derivative of the general formula (IV) as defined in claim 9 in the presence of a cobalt compound.

13. The method of claim 12, wherein the reaction is carried out at 50°–250° C.

14. A method for preparing a tetraazaannulene cobalt complex compound having the general formula (II) as defined in claim 9 which comprises reacting a β-dialkylamino-α-arylacrolein of the general formula (VI):

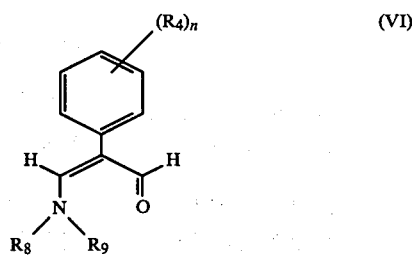

wherein
R₄ and n are the same as defined in the formula (II); and
R₈ and R₉ each independently is a C₁₋₆ alkyl group; with an o-phenylenediamine derivative of the general formula (IV) as defined in claim 9 to prepare a tetraazaannulene derivative of the formula (V) as defined in claim 9, and reacting the tetraazaannulene derivative with a cobalt compound.

15. The method of claim 14, wherein the reaction between the β-dialkylamino-α-arylacrolein of the general formula (VI) and the o-phenylenediamine derivative of the general formula (IV) is carried out at 50°–250° C.

16. The method of claim 14, wherein the reaction between the tetraazaannulene derivative of the formula (V) and the cobalt compound is carried out at 50°–250° C.

17. A method for preparing a tetraazaannulene cobalt complex compound having the general formula (II) as defined in claim 9 which comprises reacting a β-dialkylamino-α-arylacrolein of the general formula (VI) as defined in claim 9 with an o-phenylenediamine derivative of the general formula (IV) as defined in claim 9 in the presence of a cobalt compound.

18. The method of claim 17, wherein the reaction is carried out at 50°–250° C.

19. A method for preparing a tetraazaannulene derivative of the formula (V):

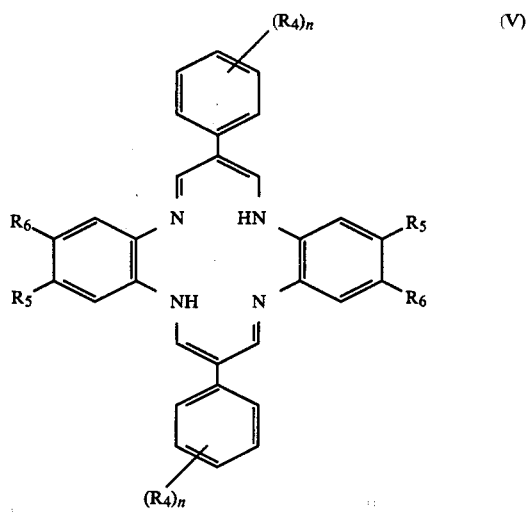

wherein
R₄ is a hydrogen atom, a C₁₋₈ alkoxy group, a C₁₋₈ alkyl group, a halogen atom, a nitro group, a cyano group, a C₁₋₈ alkylcarboxyl group, a hydroxyl group, a carboxyl group, a C₁₋₈ alkoxycarbonyl group, a carbamoyl group, a N,N-di C₁₋₆ alkylamino group, a C₁₋₈ alkylamido group, an amino group, a C₁₋₈ alkoxycarbonyl C₁₋₃ alkyl group or a N,N-di C₁₋₆ alkylamino C₁₋₃ alkyl group;
n is integer of 1 to 5; and
R₅ and R₆ each independently is a hydrogen atom, a C₁₋₈ alkoxy group, a C₁₋₈ alkyl group, a halogen atom, a nitro group, a cyano group, a C₁₋₈ alkylcarboxyl group, a hydroxyl group, a carboxyl group, a C₁₋₈ alkoxycarbonyl group, a carbamoyl group, a N,N-di C₁₋₆ alkylamino group, a C₁₋₈ alkylamido group, or a C₁₋₈ alkoxycarbonyl C₁₋₃ alkyl group;

which comprises reacting a β-alkoxy-α-arylacrolein of the general formula (III):

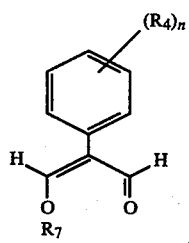

wherein $R_4$ and n are the same as defined in the formula (V);

and $R_7$ is a $C_{1-6}$ alkyl group; with an o-phenylene-diamine derivative of the general formula (IV):

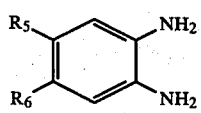

wherein $R_5$ and $R_6$ are the same as defined in the formula (V).

20. The method of claim 19, wherein the reaction is carried out at 50°–250° C.

21. A method for preparing a tetraazaannulene derivative of the formula (V):

![Formula V structure]

wherein
$R_4$ is a hydrogen atom, a $C_{1-8}$ alkoxy group, a $C_{1-8}$ alkyl group, a halogen atom, a nitro group, a cyano group, a $C_{1-8}$ alkylcarboxyl group, a hydroxyl group, a carboxyl group, a $C_{1-8}$ alkoxycarbonyl group, a carbamoyl group, a N,N-di $C_{1-6}$ alkylamino group, a $C_{1-8}$ alkylamino group, an amino group, a $C_{1-8}$ alkoxycarbonyl $C_{1-3}$ alkyl group or a N,N-di $C_{1-6}$ alkylamino $C_{1-3}$ alkyl group;
n is integer of 1 to 5; and
$R_5$ and $R_6$ each independently is a hydrogen atom, a $C_{1-8}$ alkoxy group, a $C_{1-8}$ alkyl group, a halogen atom, a nitro group, a cyano group, a $C_{1-8}$ alkylcarboxyl group, a hydroxyl group, a carboxyl group, a $C_{1-8}$ alkoxycarbonyl group, a carbamoyl group, a N,N-di $C_{1-6}$ alkylamino group, a $C_{1-8}$ alkylamido group, or a $C_{1-8}$ alkoxycarbonyl $C_{1-3}$ alkyl group;
which comprises reacting a β-dialkylamino-α-arylacrolein of the general formula (VI):

![Formula VI structure]

wherein
$R_4$ and n are the same as defined in the formula (V); and
$R_8$ and $R_9$ each independently is a $C_{1-6}$ alkyl group; with an o-phenylene-diamine derivative of the general formula (IV):

![Formula IV structure]

wherein $R_5$ and $R_6$ are the same as defined in the formula (V).

22. The method of claim 21, wherein the reaction is carried out at 50°–250° C.

* * * * *